United States Patent
Diamond

(10) Patent No.: US 11,602,554 B2
(45) Date of Patent: Mar. 14, 2023

(54) P53-TARGETING VACCINES AND PD-1 PATHWAY INHIBITORS AND METHODS OF USE THEREOF

(71) Applicant: CITY OF HOPE, Duarte, CA (US)

(72) Inventor: Don J. Diamond, Glendora, CA (US)

(73) Assignee: CITY OF HOPE, Duarte, CA (US)

( * ) Notice: Subject to any disclaimer, the term of this patent is extended or adjusted under 35 U.S.C. 154(b) by 797 days.

(21) Appl. No.: 16/467,359

(22) PCT Filed: Dec. 8, 2017

(86) PCT No.: PCT/US2017/065281
§ 371 (c)(1),
(2) Date: Jun. 6, 2019

(87) PCT Pub. No.: WO2018/107011
PCT Pub. Date: Jun. 14, 2018

(65) Prior Publication Data
US 2020/0046785 A1     Feb. 13, 2020

Related U.S. Application Data

(60) Provisional application No. 62/492,722, filed on May 1, 2017, provisional application No. 62/431,561, filed on Dec. 8, 2016.

(51) Int. Cl.
*A61K 35/768*     (2015.01)
*A61P 35/04*      (2006.01)
*A61K 39/00*      (2006.01)
*A61K 39/395*     (2006.01)
*C12N 7/00*       (2006.01)

(52) U.S. Cl.
CPC .... *A61K 35/768* (2013.01); *A61K 39/001151* (2018.08); *A61K 39/39558* (2013.01); *A61P 35/04* (2018.01); *C12N 7/00* (2013.01); *A61K 2039/5254* (2013.01); *A61K 2039/5256* (2013.01); *A61K 2039/812* (2018.08); *C12N 2710/24134* (2013.01); *C12N 2710/24143* (2013.01)

(58) Field of Classification Search
CPC .............................. A61K 35/768; A61P 35/04
See application file for complete search history.

(56) References Cited

U.S. PATENT DOCUMENTS 7,256,037 B2     8/2007  Ellenhorn et al.
7,563,448 B2 *   7/2009  Ellenhorn .......... C07K 14/4746
                                              424/277.1
2004/0253606 A1  12/2004 Aziz et al.
2006/0019268 A1   1/2006 Cheng et al.
2007/0224215 A1   9/2007 Ellenhorn et al.
2014/0364460 A1  12/2014 Freed-Pastor et al.
2016/0271239 A1   9/2016 Foy et al.

FOREIGN PATENT DOCUMENTS

JP      2003111595 A  *  4/2003
WO   WO-2016/056995 A1    4/2016
WO   WO-2016/100975 A1    6/2016
WO   WO-2016/100975 A8    6/2016
WO   WO-2016100882 A1 *   6/2016  ............. A61K 31/00
WO   WO-2016/120495 A1    8/2016
WO   WO-2016185481 A2 *  11/2016  ............. A61K 45/06
WO   WO-2016/191751 A1   12/2016

OTHER PUBLICATIONS

Written Opinion dated Feb. 16, 2018, for PCT Application No. PCT/U82017/065281, 8 pages.
Espenschied et al, CTLA-4 Blockade Enhances the Therapeutic Effect of an Attenuated Poxvirus Vaccine Targeting p53 in an Established Murine Tumor Model, The Journal of Immunology, vol. 170, pp. 3401-3407 (2003).
Hardwick et al., p53MVA Therapy in Patients with Refractory Gastrointestinal Malignancies Elevates 53-Specific CD8+ T-cell Responses, Clin Cancer Res, vol. 20, No. 17, pp. 4459-4470 (2014).
Hardwick et al., Overcoming immunosuppression to enhance a p53MVA Vaccine, OncoImmunology, vol. 3, Issue 10, pp. e958949-1 to e958949-3 (Nov. 1, 2014).
Harrop et al., Vaccination of Colorectal Cancer Patients with Modified Vaccinia Ankara Encoding the Tumor Antigen 5T4 (TroVax) Given Alongside Chemotherapy Induces Potent Immune Responses, Clin Cancer Res, vol. 13, No. 15, pp. 4487-4494 (2007).
Nanda et al., Pembrolizumab in Patients with Advanced Triple-Negative Breast Cancer: Phase lb KEYNOTE-012 Study, Journal of Clinical Oncology, vol. 34 No. 21, pp. 2460-2467 (Jul. 20, 2016).
Song et al., Diversity of Immune Response Following Stimulation With an MVA Vaccine Expressing Human p53, J. Immunother, vol. 29, No. 6, pp. 661 (2006).
Song et al., An MVA vaccine overcomes tolerance to human p53 in mice and humans, Cancer Immunol Immunother, vol. 56, pp. 1193-1205 (2007).
Yuan et al, Complete regression of cutaneous metastases with systemic immune response in a patient with triple negative breast cancer receiving p53MVA vaccine with pembrolizumab, OncoImmunology, vol. 6, No. 12, p. e1363138 to e1363138-7 (2017).

* cited by examiner

*Primary Examiner* — Mark Halvorson
*Assistant Examiner* — Dennis J Sullivan
(74) *Attorney, Agent, or Firm* — Mintz, Levin, Cohn, Ferris, Glovsky and Popeo, P.C.

(57) ABSTRACT

The disclosure provides, inter alia, methods and materials involved in treating cancer using a p53 vaccine in combination with a PD-1 pathway inhibitor.

13 Claims, 21 Drawing Sheets
Specification includes a Sequence Listing.

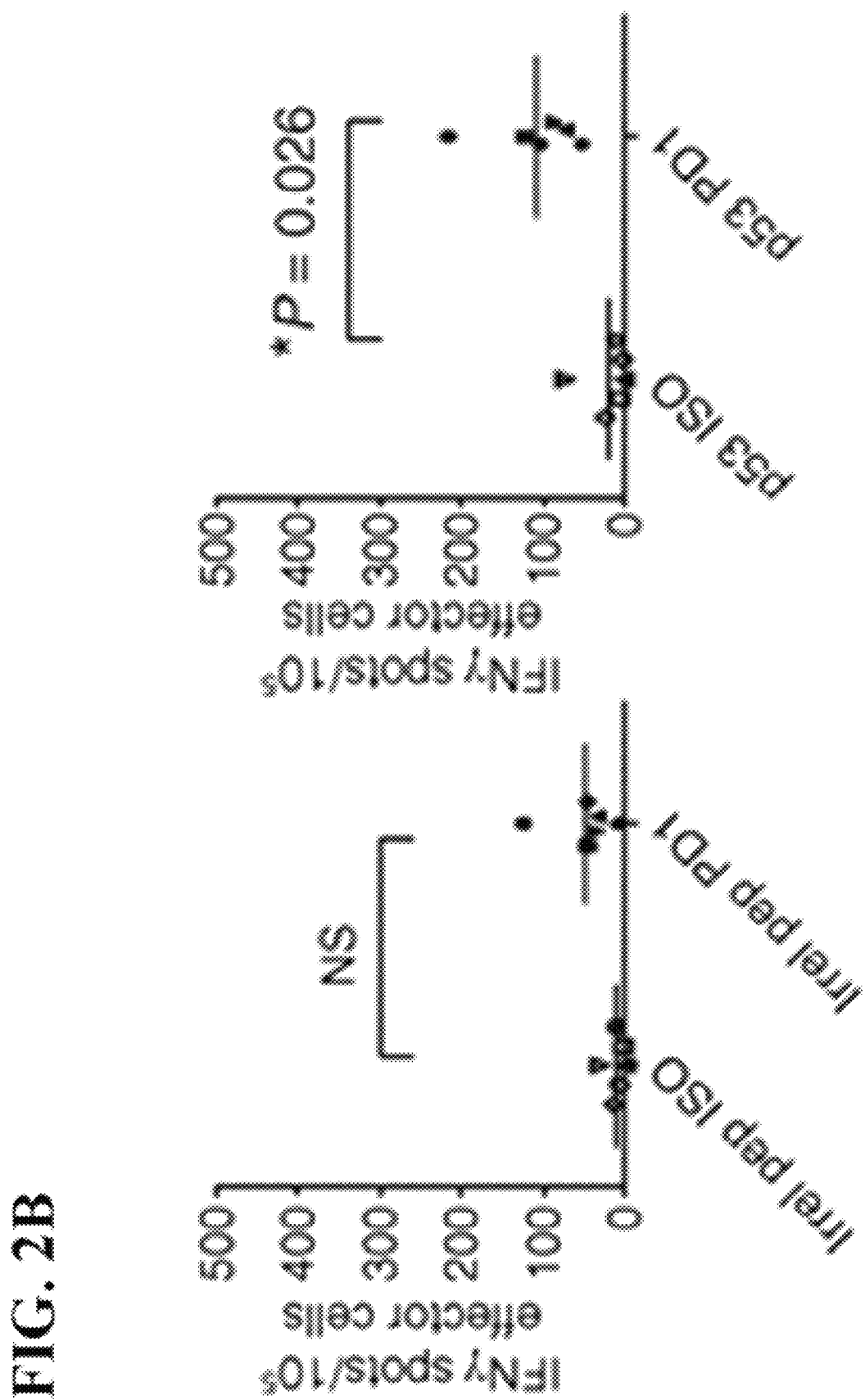

FIG. 4C

| Time | CD3⁺CD4⁺ | CD3⁺CD8⁺ | CD4/CD8 Ratio |
|---|---|---|---|
| Pre | 62.0 | 32.9 | 1.9 |
| Wk+3 | 58.7 | 34.8 | 1.7 |
| Wk+6 | 56.3 | 33.3 | 1.7 |
| Wk+9 | 56.3 | 36.0 | 1.6 |

FIG. 4D

| UPN003 | Stimulation | CD3⁺CD8⁺ CD137⁺ | CD3⁺CD4⁺ CD137⁺ |
|---|---|---|---|
| Pre | NIL | 0.03 | 0.03 |
| | $p53_{25}$ | 0.09 | 0.13 |
| | $pp65_{131}$ | 0.08 | 0.01 |
| | $VV_{86}$ | 0.13 | 0.09 |
| | MVA | 0.08 | 0.13 |
| | p53MVA | 0.06 | 0.15 |
| Wk+3 | NIL | 0.10 | 0.02 |
| | $p53_{25}$ | 0.12 | 0.02 |
| | $pp65_{131}$ | 0.03 | 0.05 |
| | $VV_{86}$ | 0.10 | 0.06 |
| | MVA | 0.08 | 0.06 |
| | p53MVA | 0.12 | 0.12 |
| Wk+6 | NIL | 0.14 | 0.02 |
| | $p53_{25}$ | 0.09 | 0.08 |
| | $pp65_{131}$ | 0.05 | 0.00 |
| | $VV_{86}$ | 0.27 | 0.02 |
| | MVA | 0.42 | 0.15 |
| | p53MVA | 0.79 | 0.20 |
| Wk+9 | NIL | 0.09 | 0.02 |
| | $p53_{25}$ | 0.20 | 0.03 |
| | $pp65_{131}$ | 0.06 | 0.03 |
| | $VV_{86}$ | 0.67 | 0.03 |
| | MVA | 0.31 | 0.03 |
| | p53MVA | 1.52 | 0.11 |

| Sample ID | Visual inspection | Bioanalyzer (ng/μl) | RIN |
|---|---|---|---|
| 1: Pre | two distinct peaks | 141 | 10 |
| 2: Wk+3 | two distinct peaks | 143 | 10 |
| 3: Wk+6 | two distinct peaks | 211 | 10 |
| 4: Wk+9 | two distinct peaks | 171 | 9.9 |
| 5: Wk+24 | two distinct peaks | 138 | 10 |

P53-TARGETING VACCINES AND PD-1 PATHWAY INHIBITORS AND METHODS OF USE THEREOF

CROSS-REFERENCE TO RELATED APPLICATIONS

This application is a Section 371 US national phase of International Application No. PCT/US2017/65281 filed Dec. 8, 2017, which claims priority to U.S. Application No. 62/492,722 filed May 1, 2017, and to U.S. Application No. 62/431,561 filed Dec. 8, 2016, the disclosures of which are incorporated by reference herein in their entirety.

REFERENCE TO A "SEQUENCE LISTING," A TABLE, OR A COMPUTER PROGRAM LISTING APPENDIX SUBMITTED AS AN ASCII FILE

The Sequence Listing written in file 048440-641001WO Sequence Listing_ST25, created on Dec. 6, 2017, 2177 bytes, machine format IBM-PC, MS Windows operating system, is incorporated herein by reference.

BACKGROUND

Over the last decade much progress has been made improving survival with systemic chemotherapy, but unfortunately most patients still succumb to their metastatic disease. Cytotoxic chemotherapy kills rapidly dividing cells and limits disease progression for a limited amount of time before the tumor develops resistance.

About 40-60% of solid tumors have p53 mutations, which results in the accumulation of oncogenic p53 protein within tumor cells. In contrast, the concentration of normal p53 in healthy cells is low, making p53 an attractive target for immunotherapy. Vaccines, including the genetically engineered virus MVA (modified vaccinia Ankara) have been used to immunize patients with the wild type p53 antigen. While p53 MVA has been shown to be well tolerated, other cancer vaccine compositions targeting self-molecules have been associated with adverse events and have been shown to initiate autoimmune reactions.

Therefore, there remains a need in the art to develop effective cancer vaccine treatments that are less likely to have serious adverse events, such as severe autoimmune reaction. The methods provided herein address these and other needs in the art.

SUMMARY

The disclosure provides methods for treating cancer in a subject in need thereof by administering to the subject an effective amount of a p53-targeting vaccine and an effective amount of a PD-1 pathway inhibitor. In embodiments, the effective amount of the p53-targeting vaccine is a low dose amount of the p53-targeting vaccine when compared to a standard dose, such as a standard dose reduced by 5% to 90%. In embodiments, the p53-targeting vaccine is a modified vaccinia Ankara. In some embodiments, the PD-1 pathway inhibitor is pembrolizumab, nivolumab, pidilizumab, avelumab, atezolizumab, durvalumab, BMS-936559, a biosimilar thereof, or a combination of two or more thereof. In embodiments, the cancer is breast cancer, for example, metastatic breast cancer, triple negative breast cancer, metastatic triple negative breast cancer, HER2/neu negative breast cancer, metastatic HER2/neu negative breast cancer, progesterone receptor negative breast cancer, metastatic progesterone receptor negative breast cancer. In embodiments, the cancer is head and neck squamous cell carcinoma, for example, oral cancer, pharyngeal cancer, or metastatic head and neck squamous cell carcinoma. In embodiments, the cancer is non-small cell lung cancer, for example, adenocarcinoma or metastatic adenocarcinoma. In embodiments, the cancer is soft tissue sarcoma, for example, liposarcoma, or metastatic soft tissue sarcoma. In embodiments, the cancer is hepatocellular carcinoma, such as metastatic hepatocellular carcinoma. In embodiments, the cancer is renal cell carcinoma, such as metastatic renal cell carcinoma. In embodiments, the cancer is melanoma, such as metastatic melanoma. In embodiments, the cancer is bladder cancer, such as metastatic bladder cancer. In embodiments, the cancer is colorectal carcinoma, such as metastatic colorectal carcinoma. In embodiments, the cancer is pancreatic cancer, such as metastatic pancreatic cancer. In embodiments, the p53-targeting vaccine and PD-1 are administered sequentially or concurrently.

The disclosure provides methods of treating a cutaneous metastasis in a subject in need thereof by administering a p53-targeting vaccine and a PD-1 pathway inhibitor. In embodiments, the subject is a p53-mutant cancer patient; an estrogen receptor-expressing cancer patient; a human epidermal growth factor receptor 2-expressing cancer patient; a breast cancer patient, or a combination thereof. In embodiments, the effective amount of the p53-targeting vaccine is a low dose amount of the p53-targeting vaccine when compared to a standard dose, such as a standard dose reduced by 5% to 90%. In embodiments, the p53-targeting vaccine is a modified vaccinia Ankara. In some embodiments, the PD-1 pathway inhibitor is pembrolizumab, nivolumab, pidilizumab, avelumab, atezolizumab, durvalumab, BMS-936559, a biosimilar thereof, or a combination of two or more thereof. In embodiments, the p53-targeting vaccine and PD-1 are administered sequentially or concurrently.

The disclosure provides methods of treating a visceral metastasis in a subject in need thereof by administering a p53-targeting vaccine and a PD-1 pathway inhibitor. In embodiments, the subject is a p53-mutant cancer patient. In embodiments, the subject is a liver cancer subject. In embodiments, the visceral metastasis is a metastasis to the liver. In embodiments, the visceral metastasis is a metastasis to the liver, the lungs, the heart, the pancreas, the intestines, the pleura, the peritoneum, or a combination thereof. In embodiments, the effective amount of the p53-targeting vaccine is a low dose amount of the p53-targeting vaccine when compared to a standard dose, such as a standard dose reduced by 5% to 90%. In embodiments, the p53-targeting vaccine is a modified vaccinia Ankara. In some embodiments, the PD-1 pathway inhibitor is pembrolizumab, nivolumab, pidilizumab, avelumab, atezolizumab, durvalumab, BMS-936559, a biosimilar thereof, or a combination of two or more thereof. In embodiments, the p53-targeting vaccine and PD-1 are administered sequentially or concurrently.

The disclosure provides methods for treating cancer in a subject in need thereof by administering to the subject an effective amount of a p53-targeting vaccine and an effective amount of a PD-1 pathway inhibitor. In embodiments, the PD-1 pathway inhibitor is a PD-1 antagonist. In embodiments, the PD-1 pathway inhibitor is a PD-L1 antagonist. In embodiments, the effective amount of the p53-targeting vaccine and the effective amount of the PD-1 pathway inhibitor are a combined effective amount.

The disclosure provides methods for treating cancer in a subject in need thereof by administering to the subject an effective amount of a p53-targeting vaccine, an effective amount of a first PD-1 pathway inhibitor, and an effective amount of a second PD-1 pathway inhibitor. In embodiments, the first and second PD-1 pathway inhibitors are PD-1 antagonists. In embodiments, the first and second PD-1 pathway inhibitors are PD-L1 antagonists. In embodiments, the first PD-1 pathway inhibitor is a PD-1 antagonist, and the second PD-1 pathway inhibitor is a PD-L1 antagonist. In embodiments, the effective amount of the p53-targeting vaccine, the effective amount of the first PD-1 pathway inhibitor, and the effective amount of the second PD-1 pathway inhibitor are a combined effective amount.

BRIEF DESCRIPTION OF THE DRAWINGS

FIGS. 2A-2B. FIG. 2A shows a significant inverse correlation relationship between the frequency of PD1$^+$ T cells and anti-p53 CD8$^+$ T cell response in the trial subjects administered treatment with p53-targeting vaccine alone. FIG. 2B shows antibody blockade of PD-1 in vitro increased the p53 immune responses detected after the second or third immunizations.

FIGS. 4A-4D show specificity of the response of T cells from peripheral blood mononuclear cells (PBMC) collected pre- and post-treatment with p53MVA and pembrolizumab. PBMC samples from patient's blood before (Pre) and 3 (Wk+3), 6 (Wk+6), and 9 (Wk+9) weeks after treatment were stimulated in vitro with recall antigens for 24 h and analyzed for the expression of CD137 on the surface of CD8$^+$ T cells (FIG. 4A) and CD4$^+$ T cells (FIG. 4B). The results in FIG. 4C show the percentages of CD3$^+$CD4$^+$ T cells, CD3$^+$CD8$^+$ T cells, and their ratio. The results in FIG. 4D show the amounts of CD3$^+$CD4$^+$CD137$^+$ cells, CD3$^+$CD8$^+$CD137$^+$ cells. NIL, medium alone; pp65(138), pool of 138 peptides derived from pp65 sequences from CMV; VV(86), pool of 86 peptides derived from several protein sequences from MVA; p53(96), pool of 96 peptides derived from p53 protein sequences; MVA, "wild type" MVA virus; p53MVA, p53-expressing recombinant MVA virus.

(FIG. 7A) The treatment schema: p53MVA vaccine and pembrolizumab were given concurrently every three weeks for three cycles. Pembolizumab alone was then administered every three weeks for an additional four doses. (FIG. 7B) Patient's skin pre- and 9 weeks post-treatment: prior to treatment (left) diffuse skin metastases covering 50% of the body area were visible. After two cycles of combined therapy (right) significant improvement was noted. (FIG. 7C) Pre- and post-treatment histopathology: pre-treatment skin punch biopsy (left) shows tumor nests composed of pleomorphic cells present predominantly within lymphovascular spaces. Post-treatment biopsy (right) demonstrates mild fibrosis and superficial perivascular lymphocytic infiltrate with no residual malignant cells present. FIG. 7B is also shown in FIG. 5.

FIG. 7C is also shown in FIGS. 6B and 6D.

(FIG. 9A) shows hierarchic clustering of 5 PBMC samples for 730 immune profiling genes and (FIG. 9B) shows clustering for 71 selected genes to assess T cell functions. The heat map in (FIG. 9B) shows complete segregation of the PBMC samples at weeks 9 and 24 after initiation of treatment from the remaining samples at weeks 6, 3, and Pre-treatment. Heat maps present normalized data scaled to give all genes equal variance (FIG. 11). Light gray indicates high expression; black indicates low expression. (FIG. 9C) depicts immune function pathway scores plotted to show how they vary across time during treatment. Lines show each pathway's average score of their transcriptomes. The T cell functions and associated immune response categories peak at week 9. The list of genes that define pathways is included in Table 5. (FIG. 9D) shows the expression of genes encoding selected stimulatory and inhibitory molecules that play a major role in pathways determining the balance between activation/duration and inhibition/exhaustion of T cell immune responses.

DETAILED DESCRIPTION

Definitions

Figure 1:
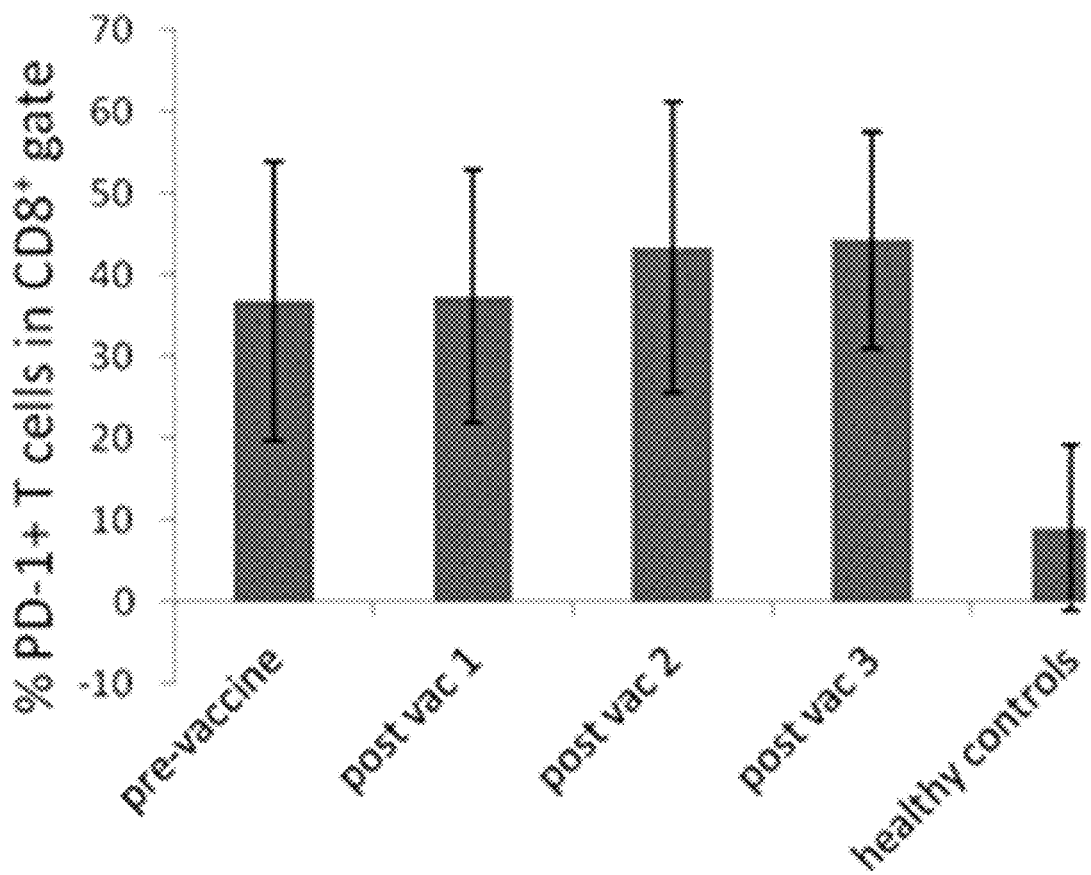
FIG. 1 shows percent change in PD-1 expressing (PD-1$^+$) T cells in CD8$^+$ gate before and during treatment with p53-targeting vaccine as compared to healthy controls.

The abbreviations used herein have their conventional meaning within the chemical and biological arts. The practice of the present disclosure will employ, unless otherwise indicated, conventional techniques of tissue culture, immunology, molecular biology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (2002) Cold Spring Harbor Laboratory Press; Sohail (2004) Gene Silencing by RNA Interference: Technology and Application (CRC Press).

The singular forms "a," "an," and "the" include plural references unless the context clearly dictates otherwise. For example, reference to "a cancer cell" includes a plurality of cancer cells.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

A "ligand" refers to an agent, e.g., a polypeptide or other molecule, capable of binding to a receptor.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

The term "culture" or "cell culture" means the maintenance of cells, for example cancer cells, in an artificial, in vitro environment. A "cell culture system" is used herein to refer to culture conditions in which a population of cells may be grown as monolayers or in suspension. "Culture medium" is used herein to refer to a nutrient solution for the culturing, growth, or proliferation of cells.

As used herein the term "biosimilar" in reference to an antibody or a vaccine is an antibody or vaccine that is highly similar to a reference product, i.e., a reference antibody (such as a PD-1 pathway inhibitor) or a reference vaccine (such as a p53-targeting vaccine). A biosimilar has no meaningful clinical, biological, or chemical difference from the reference product in terms of, for example, safety, purity, potency, stability, and the like. For example, a biosimilar form of pembrolizumab is an antibody which a regulatory authority deems to be "highly similar" to the reference product KEYTRUDA® on the basis of an abbreviated regulatory submission.

The term "antibody" is used according to its commonly known meaning in the art. As used herein, "antibody" may also refer to the antigen binding fragment thereof. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al, Nature, 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al, Nature 348: 552-554 (1990); Marks et al, Biotechnology 10:779-783 (1992)).

The epitope of a mAb is the region of its antigen to which the mAb binds. Two antibodies bind to the same or overlapping epitope if each competitively inhibits (blocks) binding of the other to the antigen. That is a 1×, 5×, 10×, 20× or 100× excess of one antibody inhibits binding of the other by at least 30% but preferably 50%, 75%, 90% or even 99% as measured in a competitive binding assay (Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

As defined herein, the term "inhibition", "inhibit", "inhibiting" and the like in reference to a protein-inhibitor (e.g., a PD-1 pathway inhibitor) interaction means negatively affecting (e.g., decreasing) the activity or function of the protein (e.g., decreasing the activity of a PD-1 protein) relative to the activity or function of the protein in the absence of the inhibitor (e.g., a PD-1 pathway inhibitor). In some embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., a PD-1 protein). Similarly an "inhibitor" is a compound or protein (e.g., monoclonal antibody) that inhibits a PD-1 protein, e.g., by binding, partially or totally blocking, decreasing, preventing, delaying, inactivating, desensitizing, or down-regulating activity (e.g., PD-1 protein activity).

A "p53 protein" or "p53" as referred to herein includes any of the recombinant or naturally-occurring forms of cellular tumor antigen p53 (p53) or variants or homologs thereof that maintain p53 activity (e.g. within at least 50%, 80%, 90%, 95%, 96%, 97%, 98%, 99% or 100% activity compared to p53). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring p53. In embodiments, p53 is substantially identical to the protein identified by the UniProt reference number P04637 or a variant or homolog having substantial identity thereto. In embodiments, p53 is a p53 mutant protein.

The term "mutant protein" as used herein refers to a protein having aberrant biological activity compared to a non-mutant protein (e.g., a non-mutant p53 protein may be a protein identified by UniProt reference number P04637). A mutant protein may have increased or decreased biological activity or the mutant protein may have no detectable biological activity compared to the corresponding non-mutant protein (e.g. a non-mutant p53 protein identified by UniProt reference number P04637). A mutant protein may have biological activity distinct from the non-mutant protein (e.g. a non-mutant p53 protein identified by UniProt reference number P04637). Mutant proteins are encoded by DNA sequences (e.g., genes) including base pair insertions, deletions, or substitutions that are absent in the corresponding non-mutant protein and that result in the modulation (e.g., increased, decreased, loss of function, gain of function) of biological activity compared to the non-mutant protein.

The term "p53 mutant" or "p53 mutant protein" refers to a p53 protein with aberrant biological activity compared to a non-mutant (wildtype) p53 protein (e.g., the p53 protein identified by UniProt reference number P04637). The mutant p53 protein as referred to herein fails to act as a suppressor of cell division and may exist at elevated intracellular levels compared to a non-mutant p53 protein. Mutations in the p53 gene (e.g., the human p53 gene identified by Ensebl reference number ENSG00000141510) have been found to correlate with aggressive disease characteristics and metastasis.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

A "$CD4^+$ T lymphocyte" or "CD4 T cell" as referred to herein is lymphocyte that expresses the CD4 glycoprotein on its surface. CD4 T cells include helper T cells, which are T cells that help orchestrate the immune response, including antibody responses and killer T cell responses. CD4 T cell precursors differentiate into one of several subtypes, including TH1 (type 1 helper T cell), TH2 (type 2 helper T cell), TH3 (T helper 3 cells), TH17 (T helper 17 cells) or TFH (Follicular B helper T cells). These subtypes of helper T cells are characterized by their secretion of different cytokines to facilitate different types of immune responses. In embodiments, a CD4 T cell is an effector T cell. An "effector T cell" as referred to herein is a T cell that has been activated by its cognate antigen, and is actively involved in eliminating a pathogen. Thus, an effector T cell actively responds to a stimulus (a pathogen or a costimulation) and carries out a cell-mediated immune response. Non-limiting examples of effector T cells as referred to herein include helper T cells, killer T cells (cytotoxic T cells) and regulatory T cells.

A "$CD8^+$ T lymphocyte" or "CD8 T cell" as referred to herein is a lymphocyte that expresses the CD8 glycoprotein on its surface. Examples of CD8 T cells include cytotoxic T cells and natural killer cells.

The term "patient" or "subject" refer to a living organism suffering from or prone to a disease or condition (e.g., cancer) that can be treated by administration of a compound or composition as provided herein. Non-limiting examples include humans, other mammals, bovines, rats, mice, dogs, monkeys, goat, sheep, cows, deer, and other non-mammalian animals. In embodiments, a patient is human. In some embodiments, a patient is a dog or a cat. In embodiments, the subject is a cancer patient. In embodiments, the subject is a p53-mutant cancer patient. In embodiments, the subject is an estrogen receptor-expressing cancer patient. In embodiments, the subject is a human epidermal growth factor receptor 2-expressing cancer patient. In embodiments, the subject is a breast cancer patient. In embodiments, the subject is a metastatic breast cancer patient. In embodiments, the subject is a triple negative breast cancer patient. In embodiments, the subject is an indolent cancer patient.

A "p53-mutant cancer patient" as used herein refers to a cancer patient having cancer cells that express p53 mutant proteins. In embodiments, the p53-mutant cancer patient does not detectably express a mutated oncogenic protein in addition to a p53 mutant protein.

An "estrogen receptor-expressing cancer patient" as used herein refers to a cancer patient having cancerous cells that express estrogen receptors.

The term "estrogen receptor" or "ER" as referred to herein includes any of the recombinant or naturally-occurring forms of human estrogen receptor or variants or homologs thereof that maintain human estrogen receptor activity (e.g. within at least 50%, 80%, 90%, 95%, 96%, 97%, 98%, 99% or 100% activity compared to human estrogen receptor). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring human estrogen receptor. In embodiments, human estrogen receptor is substantially identical to the protein identified by the UniProt reference number P03372 or a variant or homolog having substantial identity thereto.

A "human epidermal growth factor receptor 2-expressing cancer patient" as used herein refers to a cancer patient having cancerous cells that express human epidermal growth factor receptor 2.

The term "human epidermal growth factor receptor 2", also known as "receptor tyrosine-protein kinase erbB-2", as referred to herein includes any of the recombinant or naturally-occurring forms of human epidermal growth factor receptor 2 or variants or homologs thereof that maintain human epidermal growth factor receptor 2 activity (e.g. within at least 50%, 80%, 90%, 95%, 96%, 97%, 98%, 99% or 100% activity compared to human epidermal growth factor receptor 2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring human epidermal growth factor receptor 2. In embodiments, human epidermal growth factor receptor 2 is substantially identical to the protein identified by the UniProt reference number P04626 or a variant or homolog having substantial identity thereto.

As used herein, a "triple negative breast cancer patient" is a breast cancer patient having tumors that do not express estrogen receptors, progesterone receptors, or human epidermal growth factor receptor 2.

The term "progesterone receptor" or "PR" as referred to herein includes any of the recombinant or naturally-occurring forms of human progesterone receptor or variants or homologs thereof that maintain human progesterone receptor activity (e.g. within at least 50%, 80%, 90%, 95%, 96%, 97%, 98%, 99% or 100% activity compared to human progesterone receptor). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring human progesterone receptor. In embodiments, human progesterone receptor is substantially identical to the protein identified by the UniProt reference number P06401 or a variant or homolog having substantial identity thereto.

As used herein, an "indolent cancer patient" is a cancer patient wherein the cancer grows at a slow rate. In embodiments, the subject does not have a detectable breast cancer tumor. In embodiments, the subject does not have a detectable cancer tumor.

As used herein, "effective amount" or "combined effective amount" refers to a treatment regimen that utilizes a p53 vaccine (e.g., p53-targeting vaccine) and at least one PD-1 pathway inhibitor in an amount that is sufficient to reduce, shrink, and/or kill cancer cells. The patient is treated with a combined effective amount of a p53 vaccine (e.g., p53-targeting vaccine) and at least one PD-1 pathway inhibitor to reduce, shrink, and/or kill cancer cells. When used herein in reference to administration to a subject in need thereof, the terms "combined effective amount" or "effective amount" mean an amount of a p53 vaccine (e.g., p53-targeting vaccine) and a PD-1 pathway inhibitor that are used in a treatment regimen to treat a cancer. An effective amount can be administered in one or more administrations, applications or dosages. Such delivery is dependent on a number of variables including the time period which the individual dosage unit is to be used, the bioavailability of the composition, the route of administration, etc. It is understood, however, that specific amounts of the compositions (e.g., p53-targeting vaccine, PD-1 pathway inhibitors) for any particular subject depends upon a variety of factors including the activity of the specific agent employed, the age, body weight, general health, sex, and diet of the subject, the time of administration, the rate of excretion, the composition combination, severity of the particular cancer being treated and form of administration. In embodiments, when a p53 vaccine and a PD-1 pathway inhibitor are used in a combinated effective amount, the amount of the p53 vaccine is a lower dose than a standard dose of a p53 vaccine that is used in a treatment regimen without a PD-1 pathway inhibitor. In embodiments, when a p53 vaccine and a PD-1 pathway inhibitor are used in a combined effective amount, the amount of the PD-1 pathway inhibitor is a lower dose than a standard dose of a PD-1 pathway inhibitor that is used in a treatment regimen without a p53 vaccine. In embodiments, when a p53 vaccine and a PD-1 pathway inhibitor are used in a combined effective amount, the amount of the p53 vaccine and the amount of the PD-1 pathway inhibitor are both a lower dose than a standard dose of a p53 vaccine or a PD-1 pathway inhibitor that are used in a treatment regimen without the other.

As defined above, a "standard dose" as used herein refers to a dose or effective amount of drug that produces a desired effect or response in a fraction of patients. For the PD-1 pathway inhibitor pembrolizumab, a standard dose may be 2 mg/kg. For the PD-1 pathway inhibitor BMS-936559, a standard dose may be 10 mg/kg, 3 mg/kg, 1 mg/kg, 0.3 mg/kg, or 0.1 mg/kg. For the PD-1 pathway inhibitor durvalumab, a standard dose may be 10 mg/kg, 750 mg, or 1500 mg. For the PD-1 pathway inhibitor avelumab, a standard dose may be 10 mg/kg. For the PD-1 pathway inhibitor atezolizumab, a standard dose may be 1200 mg.

The term "kill" with respect to a cancer treatment is directed to include any type of manipulation that will lead to the death of that cancer cell or at least of portion of a population of cancer cells.

The term "progression-free survival" refers to duration of time from start of treatment to time of progression or death, whichever occurs first.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a subject in need thereof, and includes treatment of a cancer, for example, breast cancer. "Treating" or "treatment of" a condition or subject in need thereof refers to (1) taking steps to obtain beneficial or desired results, including clinical results such as the reduction of symptoms; (2) preventing the disease, for example, causing the clinical symptoms of the disease not to develop in a patient that may be predisposed to the disease but does not yet experience or display symptoms of the disease; (3) inhibiting the disease, for example, arresting or reducing the development of the disease or its clinical symptoms; (4) relieving the disease, for example, causing regression of the disease or its clinical symptoms; or (5) delaying the disease. Beneficial or desired clinical results include, but are not limited to, reduction and/or elimination of cancer cells.

A "control" sample or value refers to a sample that serves as a reference, usually a known reference, for comparison to a test sample. For example, a test sample can be taken from a patient suspected of having a given disease (e.g., cancer) and compared to samples from a known cancer patient, or a known normal (e.g., non-disease) individual. The term "control reference" refers to a control sample or value taken from a healthy subject, a cancer subject, or any population thereof. A control reference may be used to determine the effects of treatment in an individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. The term "baseline reference" refers to a control sample or value taken from an individual prior to administering treatment. For example, a baseline reference may be obtained from a subject prior to administration of the p53-targetting vaccine, PD-1 pathway inhibitor, or both. The baseline reference may be used to determine the effects of treatment in the individual. One of skill will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "disease" or "condition" refer to a state of being or health status of a patient or subject capable of being treated with a compound, pharmaceutical composition, or method provided herein. In embodiments, the disease is cancer (e.g. breast cancer, ovarian cancer, sarcoma, osteosarcoma, lung cancer, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, HER2/neu negative, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the interal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. Examplary anti-cancer agents include antibodies, small molecules, large molecules, and combinations thereof. In embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechlorethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'- deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metallo-proteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL$_2$), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

p53-Targeting Vaccines

A promising approach to cancer immunotherapy involves the use of vaccines which target defined tumor associated antigens. An ideal and widely expressed target for the cellular immune response is the p53 gene product. Approximately 40-60% of solid tumors have p53 mutations. Hainaut et al, Adv Cancer Res, 77:81-137 (2000). Mutations of p53, which abrogate its function as a suppresser of cell division, are associated with high intracellular concentration of the p53 protein. This makes p53 an attractive target for immunotherapy, since the intracellular concentration of wild type p53 in healthy tissue is low. Cells expressing normal p53 at low levels will escape an enhanced immune response to over-expressed mutant p53. In addition, there is considerable evidence that p53 mutation is associated with aggressive disease and metastasis. Antibodies against human p53 are demonstrable in a notable proportion of patients with breast, lung, colorectal, gastric, esophageal, ovarian, pancreatic, and prostate cancer. Furthermore, the presence of T cell responses to p53 has been demonstrated in peripheral blood mononuclear cells (PBMC) from patients with colon and ovarian cancer. Benson et al, Blood, 116(13)2286-94 (2010); Lambeck et al, Int J Cancer, 121(3):606-14 (2007); Song et al, Cancer Immunol Immun, 56(8): 1193-1205 (2007); Song et al, Cancer Invest, 29(8)501-510 (2011).

Attenuated poxviruses are being developed as vaccines in numerous diseases, including influenza, solid tumors like colon cancer, CMV, HIV, malaria and tuberculosis. Modified Vaccinia virus Ankara (MVA) is an attenuated, replication deficient vaccinia virus strain which is highly immunogenic. The lack of productive viral replication gives MVA a good safety profile, due to minimal potential for reversion to virulent forms, even when used in immunocompromised individuals. Despite its inability to replicate in most mammalian cells, MVA can still efficiently express viral and recombinant genes making it a potent antigen delivery platform. Furthermore, due to the inactivation of immune evasion genes, MVA vectors demonstrate useful adjuvant properties. MVA vectors are taken up by antigen presenting cells such as dendritic cells, allowing cross presentation of transgene encoded antigens and priming of specific T cell responses. Antoine et al, Virology, 244(2)365-396 (1998).

MVA was administered as a smallpox vaccine to over 120,000 individuals in Europe during the 1970s. No serious adverse events were reported and no reports of systemic infection occurred. Recombinant MVA vaccines have been evaluated in over 15 clinical trials in the United States and Europe and no serious adverse events have been reported. Minor adverse events include mild injection site discomfort and erythema and transient influenza like symptoms. In patients with cancer, administration of $5 \times 10^8$ pfu of recombinant MVA was well tolerated and resulted in recombinant protein specific immunogenicity and evidence of clinical cancer response. Meyer et al, Cancer Immunol Immunother, 54(5)453-467 (2005); Harrop et al, Clin Cancer Res, 13(15 Pt 1):4487-4494 (2007); Hardwick et al, Clin Cancer Res, 20(17):4459-4470 (2014).

The term "p53-targeting vaccine" or "p53 vaccine" as used herein refers to a viral composition capable of stimulating the production of antibodies against the p53 protein or a variant (e.g., mutant protein) thereof. In embodiments, the p53-targeting vaccine is a modified vaccinia Ankara (MVA) vector. In embodiments, p53MVA is a Modified Vaccina Ankara Virus vaccine expressing the full length, wild type human p53 gene. In embodiments, p53MVA is a Modified Vaccina Ankara Virus vaccine expressing the wild type human p53 gene. p53MVA and variants thereof are described in U.S. Pat. Nos. 7,256,037 and 7,563,448, the disclosures of which are incorporated by reference herein in their entirety.

In embodiments, the p53-targeting vaccine is a Modified Vaccina Ankara Virus vaccine expressing SEQ ID NO: 1. In embodiments, the p53MVA is a Modified Vaccina Ankara Virus vaccine expressing a nucleic acid sequence having at least 75% sequence identity to SEQ ID NO: 1. In embodiments, the p53MVA is a Modified Vaccina Ankara In embodiments, the p53MVA is a Modified Vaccina Ankara Virus vaccine expressing a nucleic acid sequence having at least 80% sequence identity to SEQ ID NO: 1. In embodiments, the p53MVA is a Modified Vaccina Ankara Virus vaccine expressing a nucleic acid sequence having at least 85% sequence identity to SEQ ID NO: 1. In embodiments, the p53MVA is a Modified Vaccina Ankara Virus vaccine expressing a nucleic acid sequence having at least 90% sequence identity to SEQ ID NO: 1. In embodiments, the p53MVA is a Modified Vaccina Ankara Virus vaccine expressing a nucleic acid sequence having at least 95% sequence identity to SEQ ID NO: 1. In embodiments, the MVA virus is GenBank Accesion Number U94848 that is a variant of the Ankara strain of vaccinia virus that was derived by over 570 serial passages on primary chicken embryo fibroblasts.

PD-1 Signaling Pathway

Provided herein are Programmed Death 1 (PD-1) pathway inhibitors or Programmed Death 1 (PD-1) signaling pathway inhibitors. PD-1 and its ligand PD-L1 play a key role in tumor immune escape and the formation of tumor microenvironment, closely related with tumor generation and development. Expression of PD-L1 is induced by multiple proinflammatory molecules, including types I and II IFN-γ, TNF-α, LPS, GM-CSF and VEGF, as well as the cytokines IL-10 and IL-4, with IFN-γ being the most potent inducer.

A "PD-1 protein," "PD-1," or "PD-1 receptor" as referred to herein includes any of the recombinant or naturally-occurring forms of Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto.

A "PD-L1" or "PD-L1 protein" as referred to herein includes any of the recombinant or naturally-occurring forms of programmed death ligand 1 (PD-L1) also known as cluster of differentiation 274 (CD 274) or variants or homologs thereof that maintain PD-L1 activity (e.g. within at least 50%, 80%, 90%, 95%, 96%, 97%, 98%, 99% or 100% activity compared to PD-L1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-L1 protein. In embodiments, the PD-L1 protein is substantially identical to the protein identified by the UniProt reference number Q9NZQ7 or a variant or homolog having substantial identity thereto.

A "PD-1 pathway inhibitor," "Programmed Death 1 (PD-1) pathway inhibitor," "PD-1 signaling pathway inhibitor," or "Programmed Death 1 (PD-1) signaling pathway inhibitor" as provided herein refers to a substance capable of detectably lowering expression of or activity level of the PD-1 signaling pathway compared to a control. The inhibited expression or activity of the PD-1 signaling pathway can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a compound or small molecule that inhibits the PD-1 signaling pathway e.g., by binding, partially or totally blocking stimulation of the PD-1 signaling pathway, decrease, prevent, or delay activation of the PD-1 signaling pathway, or inactivate, desensitize, or down-regulate signal transduction, gene expression or enzymatic activity of the PD-1 signaling pathway. The PD-1 pathway inhibitor provided herein may be a PD-1 antagonist or a PD-L1 antagonist. In embodiments, the PD-1 pathway inhibitor is a PD-1 antagonist. Thus, in embodiments, the PD-1 pathway inhibitor inhibits PD-1 activity or expression. In embodiments, the PD-1 pathway inhibitor is a PD-L1 antagonist. Thus, in embodiments, the PD-1 pathway inhibitor inhibits PD-L1 activity or expression. In embodiments, the PD-1 pathway inhibitor is a compound or a small molecule. In embodiments, the PD-1 pathway inhibitor is an antibody.

The term "PD-L1 antagonist" as provided herein refers to a substance capable of detectably lowering expression of or activity level of PD-L1 compared to a control. The inhibited expression or activity of PD-L1 can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. A PD-L1 antagonist inhibits PD-L1 e.g., by at least in part, partially or totally blocking stimulation, decreasing, preventing, or delaying activation, or inactivating, desensitizing, or down-regulating signal transduction, activity or amount of PD-L1 relative to the absence of the PD-L1 antagonist.

The term "PD-1 antagonist" as provided herein refers to a substance capable of detectably lowering expression of or activity level of PD-1 compared to a control. The inhibited expression or activity of PD-1 can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. A PD-1 antagonist inhibits PD-1 e.g., by at least in part, partially or totally blocking stimulation, decreasing, preventing, or delaying activation, or inactivating, desensitizing, or down-regulating signal transduction, activity or amount of PD-1 relative to the absence of the PD-1 antagonist.

In some embodiments, the PD-1 pathway inhibitor binds to a PD-1 receptor. Thus, the PD-1 pathway inhibitor may be a PD-1 antagonist. In some embodiments, the PD-1 pathway inhibitor is a small molecule inhibitor. In other embodiments, the PD-1 pathway inhibitor is a PD-1 antibody, for example a polyclonal or monoclonal antibody. In one preferred embodiment, the antibody is a monoclonal antibody. Non-limiting examples of suitable PD-1 pathway inhibitors include atezolizumab, nivolumab, pembrolizumab, pidilizumab, avelumab, BMS-936559, AMP-224, durvalumab, avelumab, a biosimilar of any of the foregoing, or any combination of two or more of the foregoing.

In embodiments, the PD-1 pathway inhibitor is nivolumab, pembrolizumab, pidilizumab, AMP-224, a biosimilar thereof, or any combination thereof. In embodiments, the PD-1 antagonist is nivolumab, pembrolizumab, pidilizumab, AMP-224, a biosimilar of any of the foregoing, or any combination of two or more of the foregoing.

In embodiments, the PD-1 pathway inhibitor is atezolizumab, avelumab, BMS-936559, durvalumab, a biosimilar thereof, or any combination thereof. In embodiments, the PD-L1 antagonist is atezolizumab, avelumab, BMS-936559, durvalumab, a biosimilar of any of the foregoing, or any combination of two or more of the foregoing.

In embodiments, the PD-1 pathway inhibitor binds to PD-L1. In embodiments, the PD-1 pathway inhibitor is a PD-L1 antibody. In embodiments, the PD-L1 antibody is avelumab, atezolizumab, durvalumab, or BMS-936559. In embodiments, the PD-1 pathway inhibitor is a compound or a small molecule.

The term "pembrolizumab" refers to a humanized, engineered monoclonal antibody of IgG4 isotype against the protein programmed cell death-1 (PD-1). In the customary sense, pembrolizumab refers to CAS Registry number 1374853-91-4. In embodiments, pembrolizumab is referred to with the tradename KEYTRUDA® by Merck. The term "pembrolizumab" encompasses biosimilars of pembrolizumab.

Pembrolizumab is indicated for the treatment of patients with unresectable or metastatic melanoma and disease progression following ipilimumab treatment and, if BRAF V600 mutation positive, a BRAF inhibitor. Pembrolizumab is a monoclonal antibody that binds to the PD-1 receptor and blocks its interaction with PD-L1 and PD-L2, releasing PD-1 pathway-mediated inhibition of the immune response, including the anti-tumor immune response. In syngeneic mouse tumor models, blocking PD-1 activity resulted in decreased tumor growth. The efficacy of pembrolizumab was investigated in a multicenter, open-label, randomized trial. Key eligibility criteria were progressive, unresectable/metastatic melanoma that was refractory to two or more doses of ipilimumab (3 mg/kg or higher). The trial excluded patients with autoimmune disease; medical conditions requiring immunosuppressive therapy and a history of severe immune-mediated adverse reactions to ipilimumab. 173 patients were randomized to receive 2 mg/kg (n=89) or 10 mg/kg (n=84) of pembrolizumab every 3 weeks until unacceptable toxicity or conformed disease progression. The overall response rate was 24% (95% CI) in the 2 mg/kg arm, consisting of 1 complete response and 20 partial responses. Among the 21 patients with an objective response, 3 (14%) showed progressive disease after the initial response. The remaining 18 patients (86%) had ongoing responses with durations ranging from 1.4 to 8.5 months, which included 8 patients with ongoing responses of 6 months or longer. Similar ORR results were observed in the 10 mg/kg arm. (KEYTRUDA® Prescribing Information in Merck Sharp & Dohme 2014).

The term "pidilizumab" or "CT-011" refers to a humanized, engineered monoclonal antibody of IgG1 isotype against the protein programmed cell death-1 (PD-1). In the customary sense, pidilizumab refers to CAS Registry number 1036730-42-3. The term "pidilizumab" includes biosimilars of pidilizumab.

The term "atezolizumab" or "MPDL3280A" refers to a humanized, engineered monoclonal antibody of IgG1 isotype against the protein programmed death-ligand 1 (PD-L1). In the customary sense, MPDL3280A refers to CAS Registry number 1380723-44-3. Atezolizumab is commercially available as TECENTRIQ® from Genentech. Atezolizumab is described in U.S. Pat. No. 8,217,149 which is incorporated by reference herein in its entirety and for all purposes.

The term "durvalumab" or "MEDI-4736" refers to a Fc optimized monoclonal antibody directed against the protein programmed death-ligand 1 (PD-L1). In the customary sense, durvalumab refers to CAS Registry number 1428935-60-7. Durvalumab is commercially available as IMFINZI® from AstraZeneca. The term "durvalumab" encompasses biosimilars of durvalumab.

The term "nivolumab" refers to a fully human immunoglobulin IgG4 monoclonal antibody directed against the protein programmed cell death-1 (PD-1) with immune checkpoint inhibitory and antineoplastic activities. In the customary sense, nivolumab refers to CAS Registry number 946414-94-4. Nivolumab is commercially available as OPDIVO® by Bristol-Myers Squibb. The term "nivolumab" encompasses biosimilars of nivolumab.

The term "avelumab" or "MSB0010718C" refers to a fully human IgG1 monoclonal antibody direct against programmed death-ligand 1 (PD-L1). In the customary sense, avelumab refers to CAS Registry number 1537032-82-8. Avelumab is commercially available as BAVENCIO® from EMD Serono and Pfizer. The term "avelumab" encompasses biosimilars of avelumab.

The term "AMP-224" refers to a recombinant B7-DC fusion protein that contains the extracellular domain of programmed cell death ligand 2 (PD-L2) and the Fc region of human IgG1. AMP-224 binds to programmed cell death-1 (PD-1) on chronically stimulated T-cells and reduces T-cell proliferation. AMP-224 is described in WO2010/027827 and WO2011/066342, the disclosure of which are incorporated by reference herein in their entirety. The term "AMP-224" encompasses biosimilars to AMP-224.

The term "BMS-936559" or "MDX1105" refers to an IgG4 monoclonal antibody directed against programmed death-ligand 1 (PD-L1) and are used interchangeably throughout. In the customary sense, BMS-936559 refers to CAS Registry number 1422185-22-5.

In some embodiments of the methods of treatment described herein, the PD-1 pathway inhibitor potentiates anti-tumor activity of the p53-targeting vaccine. It is contemplated that use of low-dose amounts of a p53-targeting vaccine (e.g., p53MVA), a PD-1 pathway inhibitor (e.g., pembrolizumab), or both can have surprising synergistic effects and/or reduce one or more of the negative side effects which limit the efficacy and use of p53-targeting vaccines and PD-1 pathway inhibitors.

Methods of Treatment

In embodiments, the disclosure provides of killing a cancer cell comprising delivering an effective amount of a p53-targeting vaccine and an effective amount of a PD-1 pathway inhibitor to a cancer cell. In embodiments, the cancer cell is part of a population of cultured cells (i.e., in vitro). In embodiments, the cancer cell is part of a population of cells of a subject having cancer (i.e., in vivo).

In embodiments, the disclosure provides methods for treating cancer in a subject in need thereof comprising administering to the subject an effective amount of a p53-targeting vaccine and an effective amount of a PD-1 pathway inhibitor. In aspects, the disclosure provides methods for treating cancer in a subject in need thereof comprising administering to the subject an effective amount of a p53-targeting vaccine and an effective amount of a PD-1 antagonist. In aspects, the disclosure provides methods for treating cancer in a subject in need thereof comprising administering to the subject an effective amount of a p53-targeting vaccine and an effective amount of a PD-L1 antagonist.

In embodiments, the disclosure provides methods for treating cancer in a subject in need thereof comprising administering to the subject an effective amount of a p53-targeting vaccine and an effective amount of two PD-1 pathway inhibitors. In aspects, the disclosure provides methods for treating cancer in a subject in need thereof comprising administering to the subject an effective amount of a p53-targeting vaccine and an effective amount of two PD-1 antagonists. In aspects, the disclosure provides methods for treating cancer in a subject in need thereof comprising administering to the subject an effective amount of a p53-targeting vaccine and an effective amount of two PD-L1 antagonists. In aspects, the disclosure provides methods for treating cancer in a subject in need thereof comprising administering to the subject an effective amount of a p53-targeting vaccine, an effective amount of a PD-L1 antagonist, and an effective amount of a PD-1 antagonist.

In an aspect is provided a method for treating a subject having cancer, the method comprising administering to the subject an effective amount of a p53-targeting vaccine and an effective amount of a PD-1 antagonist. In embodiments, the PD-1 antagonist binds to a PD-1 receptor. In embodiments, the PD-1 antagonist is a compound or small molecule. In embodiments, the PD-1 antagonist is an antibody. In embodiments, the PD-1 antagonist is a monoclonal antibody. Non-limiting examples of PD-1 antagonists include nivolumab, pembrolizumab, pidilizumab, AMP-224, and biosimilars thereof. In embodiments, the effective amount of a p53-targeting vaccine and the effective amount of PD-1 antagonist are a combined synergistic amount. In embodiments, the effective amount of a p53-targeting vaccine and the effective amount of PD-1 antagonist are a combined additive amount.

In an aspect is provided a method for treating a subject having cancer, the method including administering to the subject an effective amount of a p53-targeting vaccine and an effective amount of a PD-L1 antagonist. In embodiments, the PD-L1 antagonist binds to PD-L1. In embodiments, the PD-L1 antagonist is a compound or small molecule. In embodiments, the PD-L1 antagonist is a PD-L1 antibody. Non-limiting examples of PD-L1 antagonists that are PD-L1 include avelumab, atezolizumab, durvalumab, or BMS-936559 or biosimilars thereof. In embodiments, the effective amount of a p53-targeting vaccine and the effective amount of PD-L1 antagonist are a combined synergistic amount. In embodiments, the effective amount of a p53-targeting vaccine and the effective amount of PD-L1 antagonist are a combined additive amount.

In the methods provided herein, including embodiments thereof, more than one PD-1 pathway inhibitor may be administered to treat a subject having cancer. Thus, in an aspect is provided a method for treating a subject having cancer, the method including administering to the subject an effective amount of a p53-targeting vaccine, an effective amount of a first PD-1 pathway inhibitor, and an effective amount of a second PD-1 pathway inhibitor. In embodiments, the effective amount of a p53-targeting vaccine, the effective amount of a first PD-1 pathway inhibitor, and the effective amount of a second PD-1 pathway inhibitor are a combined synergistic amount. In embodiments, the effective amount of a p53-targeting vaccine, the effective amount of a first PD-1 pathway inhibitor, and the effective amount of a second PD-1 pathway inhibitor are a combined additive amount. In embodiments, the first PD-1 pathway inhibitor and the second PD-1 pathway inhibitor are both PD-1 antagonists. In embodiments, the first PD-1 pathway inhibitor and the second PD-1 pathway inhibitor are both PD-L1 antagonists. In embodiments, the first PD-1 pathway inhibitor is a PD-1 antagonist and the second PD-1 pathway inhibitor is a PD-L1 antagonist. In embodiments, the first PD-1 pathway inhibitor is a PD-L1 antagonist and the second PD-1 pathway inhibitor is a PD-1 antagonist.

Likewise, the methods provided herein, including embodiments thereof, do not restrict the combined use of PD-1 pathway inhibitors (e.g., PD-1 antagonists, PD-L1 antagonists). Thus, in an aspect is provided a method for treating a subject having cancer, the method including administering to the subject an effective amount of a p53-targeting vaccine, an effective amount of a PD-1 antagonist, and an effective amount of a PD-L1 antagonist. In embodiments, the effective amount of a p53-targeting vaccine, the effective amount of a PD-1 antagonist, and the effective amount of a PD-L1 antagonist are a combined synergistic amount. In embodiments, the effective amount of a p53-targeting vaccine, the effective amount of a PD-1 antagonist, and the effective amount of a PD-L1 antagonist are a combined additive amount.

As described above, the PD-1 pathway inhibitor used in the methods of treatment described herein may be a PD-1 antagonist or a PD-L1 antagonist. In embodiments, the PD-1 pathway inhibitor is a PD-1 antagonist. Thus, in embodiments, the PD-1 pathway inhibitor inhibits PD-1 activity or expression. In embodiments, the PD-1 pathway inhibitor is a PD-L1 antagonist. Thus, in embodiments, the PD-1 pathway inhibitor inhibits PD-L1 activity or expression. In embodiments, the PD-1 pathway inhibitor is a compound or a small molecule. In embodiments, the PD-1 pathway inhibitor is an antibody.

Cancers or tumors that can be treated by the compositions and methods described herein include cancers expressing and/or overexpressing p53, in particular p53 mutants. In embodiments, cancers or tumors that can be treated by the compositions and methods described herein include cancers expressing and/or overexpressing p53, in particular p53 mutants are metastatic cancers or metastatic tumors. Non-limiting types of cancers include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); bladder cancer; lung cancer, including non-small lung cancer; lymphomas, including Hodgkin's disease and lymphocytic lymphomas; bone cancers, including osteosarcoma and chondrosarcoma; neuroblastomas; oral cancer, including squamous cell carcinoma; ovarian cancer, including those arising from epithelial cells, stromal cells, germ cells and mesenchymal cells; uterus cancer; pancreas cancer; prostate cancer; rectal cancer; stomach cancer; sarcomas, including leiomyosarcoma, rhabdomyosarcoma, liposarcoma, fibrosarcoma and osteosarcoma; other soft tissue sarcomas; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; cancer of the lymph nodes; thyroid cancer, including thyroid adenocarcinoma and medullar carcinoma; squamous cell carcinoma of the head and neck; endocrine cancers, including adrenal gland tumors, carcinoid tumors, parathyroid tumors, pituitary gland tumors, and thyroid tumors; and renal cancer including adenocarcinoma and Wilms tumor. In preferred embodiments, cancers or tumors include breast cancer, ovarian, lymphoma, multiple myeloma, and melanoma. In certain embodiments, one or more of the cancer or tumors listed above is expressly excluded. For example, it is contemplated that the combination therapy can be beneficial for certain types of cancer (e.g., breast cancer, in particular triple negative breast cancer, and ovarian cancer), but provide a non-clinically significant or no benefit in other types of cancers.

In embodiments of the methods of treatment described herein, the cancer is breast cancer. The breast cancer can be noninvasive or invasive breast cancer. Non-limiting examples of breast cancer include ductal carcinoma in situ (DCIS), invasive ductal carcinoma (IDC), invasive lobular carcinoma (ILC), tubular carcinoma, mucinous (colloid) carcinoma, carcinomas with medullary features, invasive papillary carcinoma, and the like. In some embodiments, the breast cancer is characterized as being estrogen receptor-negative, progesterone receptor-negative, HER2-negative, or a combination of two or more thereof. In embodiments, the breast cancer is triple negative breast cancer (i.e., estrogen receptor-negative, progesterone receptor-negative, and HER2-negative). In embodiments, the breast cancer is advanced, refractory triple negative breast cancer. In embodiments, the cancer is stage I breast cancer. In embodiments, the cancer is stage II breast cancer. In embodiments, the cancer is stage III breast cancer. In embodiments, the cancer is metastatic breast cancer. In embodiments, the breast cancer is advanced, refractory breast cancer.

In embodiments of the methods of treatment described herein, the cancer is lung cancer. In embodiments, the lung cancer is non-small cell lung cancer. In embodiments, the cancer is metastatic lung cancer. In embodiments, the lung cancer is metastatic non-small cell lung cancer. In embodiments, the cancer is advanced, refractory lung cancer. In embodiments, the lung cancer is advanced, refractory non-small cell lung cancer. In embodiments, the lung cancer is a visercal metastasis.

In embodiments of the methods of treatment described herein, the cancer is a head and neck carcinoma. In embodiments, the head and neck carcinoma is squamous cell carcinoma of the head and neck. In embodiments, the cancer is metastatic head and neck carcinoma. In embodiments, the head and neck carcinoma is metastatic squamous cell carcinoma of the head and neck. In embodiments, the cancer is advanced, refractory head and neck carcinoma. In embodiments, the head and neck carcinoma is advanced, refractory squamous cell carcinoma of the head and neck.

In embodiments of the methods of treatment described herein, the cancer is hepatocellular carcinoma. In embodiments, the cancer is metastatic hepatocellular carcinoma. In embodiments, the cancer is advanced, refractory hepatocellular carcinoma. In embodiments, the hepatocellular carcinoma is a visercal metastasis.

In embodiments of the methods of treatment described herein, the cancer is renal cell carcinoma. In embodiments, the renal cell carcinoma is metastatic renal cell carcinoma. In embodiments, the renal cell carcinoma is advanced, refractory renal cell carcinoma. In embodiments, the renal cell carcinoma is a visercal metastasis.

In embodiments of the methods of treatment described herein, the cancer is melanoma. In embodiments, the melanoma is malignant melanoma. In embodiments, the melanoma is metastatic melanoma. In embodiments, the melanoma is advanced, refractory melanoma.

In embodiments of the methods of treatment described herein, the cancer is bladder cancer. In embodiments, the cancer is metastatic bladder cancer. In embodiments, the cancer is advanced, refractory bladder cancer.

In embodiments of the methods of treatment described herein, the cancer is colon cancer. In embodiments, the cancer is metastatic colon cancer. In embodiments, the cancer is advanced refractory colon cancer.

In embodiments of the methods of treatment described herein, the cancer is rectal cancer. In embodiments, the cancer is metastatic rectal cancer. In embodiments, the cancer is advanced refractory rectal cancer.

In embodiments of the methods of treatment described herein, the cancer is soft tissue sarcoma. In embodiments, the cancer is metastatic soft tissue sarcoma. In embodiments, the cancer is advanced refractory soft tissue sarcoma.

In embodiments of the methods of treatment described herein, the cancer is colorectal cancer. In embodiments, the colorectal cancer displays microsatellite instability. In embodiments, the cancer is metastatic colorectal cancer. In embodiments, the cancer is metastatic colorectal cancer that displays microsatellite instability. In embodiments, the cancer is advanced, refractory colorectal cancer. In embodiments, the cancer is advanced, refractory colorectal cancer that displays microsatellite instability.

In embodiments of the methods of treatment described herein, the cancer is pancreatic cancer. In embodiments, the cancer is metastatic pancreatic cancer. In embodiments, the cancer is advanced, refractory pancreatic cancer. In embodiments, the pancreatic cancer is a visercal metastasis.

In embodiments of the methods of treatment described herein, the cancer is ovarian cancer. In embodiments, the ovarian cancer is platinum-resistant ovarian cancer. In embodiments, the cancer is metastatic ovarian cancer. In embodiments, the cancer is metastatic platinum-resistant ovarian cancer. In embodiments, the cancer is advanced, refractory ovarian cancer. In embodiments, the cancer is advanced, refractory, platinum-resistant ovarian cancer.

In embodiments of the methods of treatment described herein, the cancer is fallopian tube carcinoma. In embodiments, the cancer is metastatic fallopian tube carcinoma. In embodiments, the cancer is advanced, refractory fallopian tube carcinoma.

In embodiments of the methods of treatment described herein, the cancer is peritoneal carcinoma. In embodiments, the cancer is metastatic peritoneal carcinoma. In embodiments, the cancer is advanced, refractory peritoneal carcinoma. In embodiments, the peritoneal carcinoma is a visercal metastasis.

In embodiments of the methods of treatment described herein, the cancer is a solid neoplasm. In embodiments, the cancer is metastatic solid neoplasm. In embodiments, the cancer is advanced, refractory solid neoplasm.

In embodiments, the compositions described herein, including embodiments thereof, are useful for treatment of cutaneous metastasis. In an aspect, a method of treating cutaneous metastasis in a subject in need thereof is provided. The method includes administering a combined effective amount of a p53-targeting vaccine and a PD-1 pathway inhibitor.

In an aspect, a method of treating cutaneous metastasis in a subject in need thereof is provided. The method includes administering a combined effective amount of a p53-targeting vaccine and a PD-1 antagonist. In embodiments, the p53-targeting vaccine is a p-53 targeting modified vaccinica Ankara virus vaccine. In embodiments, the PD-1 antagonist binds to a PD-1 receptor. In embodiments, the PD-1 antagonist is a compound or small molecule. In embodiments, the PD-1 antagonist is an antibody. In embodiments, the PD-1 antagonist is a monoclonal antibody. In embodiments, the PD-1 antagonist is nivolumab, pembrolizumab, pidilizumab, AMP-224, and biosimilars thereof. In embodiments, the combined effective amount of a p53-targeting vaccine and a PD-1 antagonist is a combined synergistic amount. In embodiments, the combined effective amount of a p53-targeting vaccine and a PD-1 antagonist is a combined additive amount.

In an aspect, a method of treating cutaneous metastasis in a subject in need thereof is provided. The method includes administering a combined effective amount of a p53-targeting vaccine and a PD-L1 antagonist. In embodiments, the PD-L1 antagonist binds to PD-L1. In embodiments, the PD-L1 antagonist is a compound or small molecule. In embodiments, the PD-L1 antagonist is a PD-L1 antibody. In embodiments, the PD-L1 antagonist is avelumab, atezolizumab, durvalumab, or BMS-936559 or biosimilars thereof. In embodiments, the combined effective amount of a p53-targeting vaccine and a PD-L1 antagonist is a combined synergistic amount. In embodiments, the combined effective amount of a p53-targeting vaccine and a PD-L1 antagonist is a combined additive amount.

In the methods provided herein, including embodiments thereof, more than one PD-1 pathway inhibitor may be administered to treat a subject having cutaneous metastasis. Thus, in an aspect, a method of treating cutaneous metastasis in a subject in need thereof is provided that includes administering a combined effective amount of a p53-targeting vaccine, a first PD-1 pathway inhibitor, and a second PD-1 pathway inhibitor. In embodiments, the combined effective amount of a p53-targeting vaccine, a first PD-1 pathway inhibitor, and a second PD-1 pathway inhibitor is a combined synergistic amount. In embodiments, the combined effective amount of a p53-targeting vaccine, a first PD-1 pathway inhibitor, and a second PD-1 pathway inhibitor is a combined additive amount.

Likewise, the methods provided herein, including embodiments thereof, do not restrict the combined use of PD-1 pathway inhibitor types (e.g., PD-1 antagonists, PD-L1 antagonists). Thus, in an aspect a method of treating cutaneous metastasis in a subject in need thereof is provided that includes administering a combined effective amount of a p53-targeting vaccine, a PD-1 antagonist, and a PD-L1 antagonist. In embodiments, the combined effective amount of a p53-targeting vaccine, a PD-1 antagonist, and a PD-L1 antagonist is a combined synergistic amount. In embodiments, the combined effective amount of a p53-targeting vaccine, a PD-1 antagonist, and a PD-L1 antagonist is a combined additive amount.

In embodiments, the compositions described herein, including embodiments thereof, are useful for treatment of visceral metastasis. In an aspect, a method of treating visceral metastasis in a subject in need thereof is provided. The method includes administering a combined effective amount of a p53-targeting vaccine and a PD-1 pathway inhibitor.

In an aspect, a method of treating visceral metastasis in a subject in need thereof is provided. The method includes administering a combined effective amount of a p53-targeting vaccine and a PD-1 antagonist. In embodiments, the p53-targeting vaccine is a p-53 targeting modified vaccinica Ankara virus vaccine. In embodiments, the PD-1 antagonist binds to a PD-1 receptor. In embodiments, the PD-1 antagonist is a compound or small molecule. In embodiments, the PD-1 antagonist is an antibody. In embodiments, the PD-1 antagonist is a monoclonal antibody. In embodiments, the PD-1 antagonist is nivolumab, pembrolizumab, pidilizumab, AMP-224, and biosimilars thereof. In embodiments, the combined effective amount of a p53-targeting vaccine and a PD-1 antagonist is a combined synergistic amount. In embodiments, the combined effective amount of a p53-targeting vaccine and a PD-1 antagonist is a combined additive amount.

In an aspect, a method of treating visceral metastasis in a subject in need thereof is provided. The method includes administering a combined effective amount of a p53-targeting vaccine and a PD-L1 antagonist. In embodiments, the PD-L1 antagonist binds to PD-L1. In embodiments, the PD-L1 antagonist is a compound or small molecule. In embodiments, the PD-L1 antagonist is a PD-L1 antibody. In embodiments, the PD-L1 antagonist is avelumab, atezolizumab, durvalumab, or BMS-936559 or biosimilars thereof. In embodiments, the combined effective amount of a p53-targeting vaccine and a PD-L1 antagonist is a combined synergistic amount. In embodiments, the combined effective amount of a p53-targeting vaccine and a PD-L1 antagonist is a combined additive amount.

In the methods provided herein, including embodiments thereof, more than one PD-1 pathway inhibitor may be administered to treat a subject having visceral metastasis. Thus, in an aspect, a method of treating visceral metastasis in a subject in need thereof is provided that includes administering a combined effective amount of a p53-targeting vaccine, a first PD-1 pathway inhibitor, and a second PD-1 pathway inhibitor. In embodiments, the combined effective amount of a p53-targeting vaccine, a first PD-1 pathway inhibitor, and a second PD-1 pathway inhibitor is a combined synergistic amount. In embodiments, the combined effective amount of a p53-targeting vaccine, a first PD-1 pathway inhibitor, and a second PD-1 pathway inhibitor is a combined additive amount.

Likewise, the methods provided herein, including embodiments thereof, do not restrict the combined use of PD-1 pathway inhibitor types (e.g., PD-1 antagonists, PD-L1 antagonists). Thus, in an aspect a method of treating visceral metastasis in a subject in need thereof is provided that includes administering a combined effective amount of a p53-targeting vaccine, a PD-1 antagonist, and a PD-L1 antagonist. In embodiments, the combined effective amount of a p53-targeting vaccine, a PD-1 antagonist, and a PD-L1 antagonist is a combined synergistic amount. In embodiments, the combined effective amount of a p53-targeting vaccine, a PD-1 antagonist, and a PD-L1 antagonist is a combined additive amount.

The frequency of administration can be any frequency that reduces the progression rate of cancer (e.g., breast cancer), increases the progression-free survival rate, or increases the median time to progression without producing significant toxicity to the subject. For example, the frequency of administration can be from about once a month to about three times a month, or from about twice a month to about six times a month, or from about once every two months to about three times every two months. The frequency of administration can remain constant or can be variable during the duration of treatment. A course of treatment with a p53-targeting vaccine and PD-1 pathway inhibitor combination therapy can include rest periods. For example, a p53-targeting vaccine and PD-1 pathway inhibitor combination therapy can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

In general, the compounds (e.g., p53-targeting vaccine, PD-1 pathway inhibitor, or both) described herein will be administered in a therapeutically effective amount by any of the accepted modes of administration for agents that serve similar utilities. The actual amount of the compound of this disclosure will depend upon numerous factors such as the severity of the disease to be treated, the age and relative health of the subject, the potency of the compound used, the route and form of administration, and other factors well known to the skilled artisan.

An effective amount or a therapeutically effective amount or dose of a compound (e.g., p53-targeting vaccine, PD-1 pathway inhibitor, or both), refers to an amount of compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Compounds that exhibit high therapeutic indices are preferred.

In embodiments of the methods of treatment described herein, the effective amount of a p53-targeting vaccine is from about $5 \times 10^{11}$ pfu to about $1 \times 10^2$ pfu. In embodiments, the effective amount of a p53-targeting vaccine is from about $5 \times 10^8$ pfu to about $1 \times 10^4$ pfu. In embodiments, the effective amount of a p53-targeting vaccine is from about $5 \times 10^6$ pfu to about $1 \times 10^4$ pfu. In embodiments, the effective amount of a p53-targeting vaccine is about $1 \times 10^{11}$ pfu. In embodiments, the effective amount of a p53-targeting vaccine is about $5 \times 10^{11}$ pfu. In embodiments, the effective amount of a p53-targeting vaccine is about $1 \times 10^{10}$ pfu. In embodiments, the effective amount of a p53-targeting vaccine is about $5 \times 10^{10}$ pfu. In embodiments, the effective amount of a p53-targeting vaccine is about $1 \times 10^9$ pfu. In embodiments, the effective amount of a p53-targeting vaccine is about $5 \times 10^9$ pfu. In embodiments, the effective amount of a p53-targeting vaccine is about $1 \times 10^8$ pfu. In embodiments, the effective amount of a p53-targeting vaccine is about $5 \times 10^8$ pfu. In embodiments, the effective amount of a p53-targeting vaccine is about $1 \times 10^7$ pfu. In embodiments, the effective amount of a p53-targeting vaccine is about $5 \times 10^7$ pfu. In embodiments, the effective amount of a p53-targeting vaccine is about $1 \times 10^6$ pfu. In embodiments, the effective amount of a p53-targeting vaccine is about $5 \times 10^6$ pfu. In embodiments, the effective amount of a p53-targeting vaccine is about $1 \times 10^5$ pfu. In embodiments, the effective amount of a p53-targeting vaccine is about $5 \times 10^5$ pfu. In embodiments, the effective amount of a p53-targeting vaccine is about $1 \times 10^4$ pfu. In embodiments, the effective amount of a p53-targeting vaccine is about $5 \times 10^4$ pfu. In embodiments, the effective amount of a p53-targeting vaccine is about $1 \times 10^3$ pfu. In embodiments, the effective amount of a p53-targeting vaccine is about $5 \times 10^3$ pfu. In embodiments, the effective amount of a p53-targeting vaccine is about $1 \times 10^2$ pfu. In embodiments, the effective amount of a p53-targeting vaccine is about $5 \times 10^2$ pfu.

In embodiments, a p53-targeting vaccine (e.g., p53MVA) used in the methods of treatment described herein is administered to the subject in an amount from about $5 \times 10^{11}$ pfu to about $1 \times 10^2$ pfu. In embodiments, a p53-targeting vaccine (e.g., p53MVA) is administered to the subject in an amount from about $5 \times 10^8$ pfu to about $1 \times 10^4$ pfu. In embodiments, a p53-targeting vaccine (e.g., p53MVA) is administered to the subject in an amount from about $5 \times 10^6$ pfu to about $1 \times 10^4$ pfu. In some embodiments, a p53-targeting vaccine (e.g., p53MVA) is administered to the subject in an amount about $1 \times 10^{11}$ pfu. In embodiments, a p53-targeting vaccine (e.g., p53MVA) is administered to the subject in an amount about $5 \times 10^{11}$ pfu. In embodiments, a p53-targeting vaccine (e.g., p53MVA) is administered to the subject in an amount about $1 \times 10^{10}$ pfu. In embodiments, a p53-targeting vaccine (e.g., p53MVA) is administered to the subject in an amount about $5 \times 10^{10}$ pfu. In embodiments, a p53-targeting vaccine (e.g., p53MVA) is administered to the subject in an amount about $1\times10^9$ pfu. In some embodiments, a p53-targeting vaccine (e.g., p53MVA) is administered to the subject in an amount about $5\times10^9$ pfu. In some embodiments, a p53-targeting vaccine (e.g., p53MVA) is administered to the subject in an amount about $1\times10^8$ pfu. In some embodiments, a p53-targeting vaccine (e.g., p53MVA) is administered to the subject in an effective amount of about $5\times10^8$ pfu. In some embodiments, a p53-targeting vaccine (e.g., p53MVA) is administered to the subject in an effective amount of about $1\times10^7$ pfu. In some embodiments, a p53-targeting vaccine (e.g., p53MVA) is administered to the subject in an amount about $5\times10^7$ pfu. In some embodiments, a p53-targeting vaccine (e.g., p53MVA) is administered to the subject in an amount about $1\times10^6$ pfu. In some embodiments, a p53-targeting vaccine (e.g., p53MVA) is administered to the subject in an amount about $5\times10^6$ pfu. In some embodiments, a p53-targeting vaccine (e.g., p53MVA) is administered to the subject in an amount about $1\times10^5$ pfu. In some embodiments, a p53-targeting vaccine (e.g., p53MVA) is administered to the subject in an amount about $5\times10^5$ pfu. In some embodiments, a p53-targeting vaccine (e.g., p53MVA) is administered to the subject in an amount about $1\times10^4$ pfu. In some embodiments, a p53-targeting vaccine (e.g., p53MVA) is administered to the subject in an amount about $5\times10^4$ pfu. In some embodiments, a p53-targeting vaccine (e.g., p53MVA) is administered to the subject in an amount about $1\times10^3$ pfu. In some embodiments, a p53-targeting vaccine (e.g., p53MVA) is administered to the subject in an amount about $5\times10^3$ pfu. In some embodiments, a p53-targeting vaccine (e.g., p53MVA) is administered to the subject in an amount about $1\times10^2$ pfu. In some embodiments, a p53-targeting vaccine (e.g., p53MVA) is administered to the subject in an amount about $5\times10^2$ pfu.

In embodiments of the methods of treatment described herein, the effective amount of a p53-targeting vaccine is from about $4.7\times10^8$ pfu to about $6.5\times10^8$ pfu. In embodiments, the effective amount of a p53-targeting vaccine is from about $4.8\times10^8$ pfu to about $6.4\times10^8$ pfu. In embodiments, the effective amount of a p53-targeting vaccine is from about $4.9\times10^8$ pfu to about $6.3\times10^8$ pfu. In embodiments, the effective amount of a p53-targeting vaccine is from about $5.0\times10^8$ pfu to about $6.2\times10^8$ pfu. In embodiments, the effective amount of a p53-targeting vaccine is from about $5.1\times10^8$ pfu to about $6.1\times10^8$ pfu. In embodiments, the effective amount of a p53-targeting vaccine is from about $5.2\times10^8$ pfu to about $6.0\times10^8$ pfu. In embodiments, the effective amount of a p53-targeting vaccine is from about $5.3\times10^8$ pfu to about $5.9\times10^8$ pfu. In embodiments, the effective amount of a p53-targeting vaccine is from about $5.4\times10^8$ pfu to about $5.8\times10^8$ pfu. In embodiments, the effective amount of a p53-targeting vaccine is from about $5.5\times10^8$ pfu to about $5.7\times10^8$ pfu.

In embodiments of the methods of treatment described herein, the effective amount of a p53-targeting vaccine is about $5.6\times10^8$ pfu. In embodiments, the effective amount of a p53-targeting vaccine is about $5.5\times10^8$ pfu. In embodiments, the effective amount of a p53-targeting vaccine is about $5.4\times10^8$ pfu. In embodiments, the effective amount of a p53-targeting vaccine is about $5.3\times10^8$ pfu. In embodiments, the effective amount of a p53-targeting vaccine is about $5.2\times10^8$ pfu. In embodiments, the effective amount of a p53-targeting vaccine is about $5.1\times10^8$ pfu. In embodiments, the effective amount of a p53-targeting vaccine is about $5.0\times10^8$ pfu. In embodiments, the effective amount of a p53-targeting vaccine is about $4.9\times10^8$ pfu. In embodiments, the effective amount of a p53-targeting vaccine is about $4.8\times10^8$ pfu. In embodiments, the effective amount of a p53-targeting vaccine is about $4.7\times10^8$ pfu. In embodiments, the effective amount of a p53-targeting vaccine is about $4.6\times10^8$ pfu. In embodiments, the effective amount of a p53-targeting vaccine is about $5.7\times10^8$ pfu. In embodiments, the effective amount of a p53-targeting vaccine is about $5.8\times10^8$ pfu. In embodiments, the effective amount of a p53-targeting vaccine is about $5.9\times10^8$ pfu. In embodiments, the effective amount of a p53-targeting vaccine is about $6.0\times10^8$ pfu. In embodiments, the effective amount of a p53-targeting vaccine is about $6.1\times10^8$ pfu. In embodiments, the effective amount of a p53-targeting vaccine is about $6.2\times10^8$ pfu. In embodiments, the effective amount of a p53-targeting vaccine is about $6.3\times10^8$ pfu. In embodiments, the effective amount of a p53-targeting vaccine is about $6.4\times10^8$ pfu. In embodiments, the effective amount of a p53-targeting vaccine is about $6.5\times10^8$ pfu.

In embodiments of the methods of treatment described herein, the effective amount of a p53-targeting vaccine is from about $1.8\times10^8$ pfu to about $3.8\times10^8$ pfu. In embodiments, the effective amount of a p53-targeting vaccine is from about $1.9\times10^8$ pfu to about $3.7\times10^8$ pfu. In embodiments, the effective amount of a p53-targeting vaccine is from about $2.0\times10^8$ pfu to about $3.6\times10^8$ pfu. In embodiments, the effective amount of a p53-targeting vaccine is from about $2.1\times10^8$ pfu to about $3.5\times10^8$ pfu. In embodiments, the effective amount of a p53-targeting vaccine is from about $2.2\times10^8$ pfu to about $3.4\times10^8$ pfu. In embodiments, the effective amount of a p53-targeting vaccine is from about $2.3\times10^8$ pfu to about $3.3\times10^8$ pfu. In embodiments, the effective amount of a p53-targeting vaccine is from about $2.4\times10^8$ pfu to about $3.2\times10^8$ pfu. In embodiments, the effective amount of a p53-targeting vaccine is from about $2.5\times10^8$ pfu to about $3.1\times10^8$ pfu. In embodiments, the effective amount of a p53-targeting vaccine is from about $2.6\times10^8$ pfu to about $3.0\times10^8$ pfu. In embodiments, the effective amount of a p53-targeting vaccine is from about $2.7\times10^8$ pfu to about $2.9\times10^8$ pfu.

In embodiments, the effective amount of a p53-targeting vaccine is about $2.8\times10^8$ pfu. In embodiments, the effective amount of a p53-targeting vaccine is about $2.7\times10^8$ pfu. In embodiments, the effective amount of a p53-targeting vaccine is about $2.6\times10^8$ pfu. In embodiments, the effective amount of a p53-targeting vaccine is about $2.5\times10^8$ pfu. In embodiments, the effective amount of a p53-targeting vaccine is about $2.4\times10^8$ pfu. In embodiments, the effective amount of a p53-targeting vaccine is about $2.3\times10^8$ pfu. In embodiments, the effective amount of a p53-targeting vaccine is about $2.2\times10^8$ pfu. In embodiments, the effective amount of a p53-targeting vaccine is about $2.1\times10^8$ pfu. In embodiments, the effective amount of a p53-targeting vaccine is about $2.0\times10^8$ pfu. In embodiments, the effective amount of a p53-targeting vaccine is about $2.9\times10^8$ pfu. In embodiments, the effective amount of a p53-targeting vaccine is about $3.0\times10^8$ pfu. In embodiments, the effective amount of a p53-targeting vaccine is about $3.1\times10^8$ pfu. In embodiments, the effective amount of a p53-targeting vaccine is about $3.2\times10^8$ pfu. In embodiments, the effective amount of a p53-targeting vaccine is about $3.3\times10^8$ pfu. In embodiments, the effective amount of a p53-targeting vaccine is about $3.4\times10^8$ pfu. In embodiments, the effective amount of a p53-targeting vaccine is about $3.5\times10^8$ pfu. In embodiments, the effective amount of a p53-targeting vaccine is about $3.6\times10^8$ pfu. In embodiments, the effective amount of a p53-targeting vaccine is about $3.7\times10^8$ pfu. In embodiments, the effective amount of a p53-targeting vaccine is about $3.8\times10^8$ pfu.

In embodiments of the methods of treatment described herein, the effective amount of a p53-targeting vaccine is from about $1.9 \times 10^8$ pfu to about $6.5 \times 10^8$ pfu. In embodiments, the effective amount of a p53-targeting vaccine is from about $2.0 \times 10^8$ pfu to about $6.4 \times 10^8$ pfu. In embodiments, the effective amount of a p53-targeting vaccine is from about $2.1 \times 10^8$ pfu to about $6.3 \times 10^8$ pfu. In embodiments, the effective amount of a p53-targeting vaccine is from about $2.2 \times 10^8$ pfu to about $6.2 \times 10^8$ pfu. In embodiments, the effective amount of a p53-targeting vaccine is from about $2.3 \times 10^8$ pfu to about $6.1 \times 10^8$ pfu. In embodiments, the effective amount of a p53-targeting vaccine is from about $2.4 \times 10^8$ pfu to about $6.0 \times 10^8$ pfu. In embodiments, the effective amount of a p53-targeting vaccine is from about $2.5 \times 10^8$ pfu to about $5.9 \times 10^8$ pfu. In embodiments, the effective amount of a p53-targeting vaccine is from about $2.6 \times 10^8$ pfu to about $5.8 \times 10^8$ pfu. In embodiments, the effective amount of a p53-targeting vaccine is from about $2.7 \times 10^8$ pfu to about $5.7 \times 10^8$ pfu. In embodiments, the effective amount of a p53-targeting vaccine is from about $2.8 \times 10^8$ pfu to about $5.6 \times 10^8$ pfu.

In embodiments, the p53-targeting vaccine (e.g., p53MVA) used in the methods described herein is present in a low dose amount. The phrase "low dose" or "low dose amount" of p53-targeting vaccine in the context of an effective amount to treat cancer refers to the use of a particular amount of p53-targeting vaccine that is lower than typically used for treating cancer. In embodiments, the "low dose" or "low dose amount" of p53-targeting vaccine is the "effective amount" or the "combined effective amount" as described herein.

In embodiments, the low dose of the p53-targeting vaccine (e.g., p53MVA) is 1/10 of the amount used for treating cancer. In embodiments, the low dose is about 1/2, about 1/3, about 1/4, about 1/5, about 1/6, about 1/7, about 1/8, about 1/9, or any range between two of the numbers, of the amount used for treating cancer. In embodiments, the low dose is about 1/2 of the amount used for treating cancer. In embodiments, the low dose is 1/2 of the amount used for treating cancer. In embodiments, the low dose is about 1/3 of the amount used for treating cancer. In embodiments, the low dose is 1/3 of the amount used for treating cancer. In embodiments, the low dose is about 1/4 of the amount used for treating cancer. In embodiments, the low dose is 1/4 of the amount used for treating cancer. In embodiments, the low dose is about 1/5 of the amount used for treating cancer. In embodiments, the low dose is 1/5 of the amount used for treating cancer. In embodiments, the low dose is about 1/6 of the amount used for treating cancer. In embodiments, the low dose is 1/6 of the amount used for treating cancer. In embodiments, the low dose is about 1/7 of the amount used for treating cancer. In embodiments, the low dose is 1/7 of the amount used for treating cancer. In embodiments, the low dose is about 1/8 of the amount used for treating cancer. In embodiments, the low dose is 1/8 of the amount used for treating cancer. In embodiments, the low dose is about 1/9 of the amount used for treating cancer. In embodiments, the low dose is 1/9 of the amount used for treating cancer.

In further embodiments, the low dose of p53-targeting vaccine used in the methods of treatment described herein is about 0.9 times, about 0.8 times, about 0.7 times, about 0.6 times, about 0.5 times, about 0.4 times, about 0.3 times, about 0.2 times, about 0.1 times, about 0.09 times, about 0.08 times, about 0.07 times, about 0.06 times, about 0.05 times, about 0.04 times, about 0.03 times, about 0.02 times, about 0.01 times, about 0.009 times, about 0.008 times, about 0.007 times, or any range between two of the numbers, less than the typical amount used for a particular situation (i.e., treating cancer).

In embodiments of the methods of treatment described herein, the low dose of p53-targeting vaccine is about 0.9 times less than the typical amount used for a particular situation (i.e., treating cancer). In embodiments, the low dose of p53-targeting vaccine is 0.9 times less than the typical amount used for a particular situation (i.e., treating cancer). In embodiments, the low dose of p53-targeting vaccine is about 0.8 times less than the typical amount used for a particular situation (i.e., treating cancer). In embodiments, the low dose of p53-targeting vaccine is 0.8 times less than the typical amount used for a particular situation (i.e., treating cancer). In embodiments, the low dose of p53-targeting vaccine is about 0.7 less than the typical amount used for a particular situation (i.e., treating cancer). In embodiments, the low dose of p53-targeting vaccine is 0.7 less than the typical amount used for a particular situation (i.e., treating cancer). In embodiments, the low dose of p53-targeting vaccine is about 0.6 times less than the typical amount used for a particular situation (i.e., treating cancer). In embodiments, the low dose of p53-targeting vaccine is 0.6 times less than the typical amount used for a particular situation (i.e., treating cancer). In embodiments, the low dose of p53-targeting vaccine is about 0.5 times less than the typical amount used for a particular situation (i.e., treating cancer). In embodiments, the low dose of p53-targeting vaccine is 0.5 times less than the typical amount used for a particular situation (i.e., treating cancer).

In embodiments, the low dose of p53-targeting vaccine is about 0.4 times less than the typical amount used for a particular situation (i.e., treating cancer). In embodiments, the low dose of p53-targeting vaccine is 0.4 times less than the typical amount used for a particular situation (i.e., treating cancer). In embodiments, the low dose of p53-targeting vaccine is about 0.3 times less than the typical amount used for a particular situation (i.e., treating cancer). In embodiments, the low dose of p53-targeting vaccine is 0.3 times less than the typical amount used for a particular situation (i.e., treating cancer). In embodiments, the low dose of p53-targeting vaccine is about 0.2 times less than the typical amount used for a particular situation (i.e., treating cancer). In embodiments, the low dose of p53-targeting vaccine is 0.2 times less than the typical amount used for a particular situation (i.e., treating cancer). In embodiments, the low dose of p53-targeting vaccine is about 0.1 times less than the typical amount used for a particular situation (i.e., treating cancer). In embodiments, the low dose of p53-targeting vaccine is 0.1 times less than the typical amount used for a particular situation (i.e., treating cancer). In embodiments, the low dose of p53-targeting vaccine is about 0.09 times less than the typical amount used for a particular situation (i.e., treating cancer). In embodiments, the low dose of p53-targeting vaccine is 0.09 times less than the typical amount used for a particular situation (i.e., treating cancer).

In embodiments of the methods of treatment described herein, the low dose of p53-targeting vaccine is about 0.08 times less than the typical amount used for a particular situation (i.e., treating cancer). In embodiments, the low dose of p53-targeting vaccine is 0.08 times less than the typical amount used for a particular situation (i.e., treating cancer). In embodiments, the low dose of p53-targeting vaccine is about 0.07 times less than the typical amount used for a particular situation (i.e., treating cancer). In embodiments, the low dose of p53-targeting vaccine is 0.07 times less than the typical amount used for a particular situation (i.e., treating cancer). In embodiments, the low dose of p53-targeting vaccine is about 0.06 times less than the typical amount used for a particular situation (i.e., treating cancer). In embodiments, the low dose of p53-targeting vaccine is 0.06 times less than the typical amount used for a particular situation (i.e., treating cancer). In embodiments, the low dose of p53-targeting vaccine is about 0.05 times less than the typical amount used for a particular situation (i.e., treating cancer). In embodiments, the low dose of p53-targeting vaccine is 0.05 times less than the typical amount used for a particular situation (i.e., treating cancer). In embodiments, the low dose of p53-targeting vaccine is about 0.04 times less than the typical amount used for a particular situation (i.e., treating cancer). In embodiments, the low dose of p53-targeting vaccine is 0.04 times less than the typical amount used for a particular situation (i.e., treating cancer). In embodiments, the low dose of p53-targeting vaccine is about 0.03 times less than the typical amount used for a particular situation (i.e., treating cancer). In embodiments, the low dose of p53-targeting vaccine is 0.03 times less than the typical amount used for a particular situation (i.e., treating cancer).

In embodiments of the methods of treatment described herein, the low dose of p53-targeting vaccine is about 0.02 times less than the typical amount used for a particular situation (i.e., treating cancer). In embodiments, the low dose of p53-targeting vaccine is 0.02 times less than the typical amount used for a particular situation (i.e., treating cancer). In embodiments, the low dose of p53-targeting vaccine is about 0.01 times less than the typical amount used for a particular situation (i.e., treating cancer). In embodiments, the low dose of p53-targeting vaccine is 0.01 times less than the typical amount used for a particular situation (i.e., treating cancer). In embodiments, the low dose of p53-targeting vaccine is about 0.009 times less than the typical amount used for a particular situation (i.e., treating cancer). In embodiments, the low dose of p53-targeting vaccine is 0.009 times less than the typical amount used for a particular situation (i.e., treating cancer). In embodiments, the low dose of p53-targeting vaccine is about 0.008 times less than the typical amount used for a particular situation (i.e., treating cancer). In embodiments, the low dose of p53-targeting vaccine is 0.008 times less than the typical amount used for a particular situation (i.e., treating cancer). In embodiments, the low dose of p53-targeting vaccine is about 0.007 times less than the typical amount used for a particular situation (i.e., treating cancer). In embodiments, the low dose of p53-targeting vaccine is 0.007 times less than the typical amount used for a particular situation (i.e., treating cancer).

In still further embodiments of the methods of treatment described herein, the low dose of p53-targeting vaccine is a dose reduced by about 5%, about 10%, about 20%, about 30%, about 40%, about 50%, about 60%, about 70%, about 80%, about 90%, or any range between two of the numbers as compared to a standard dose. In embodiments, the low dose of p53-targeting vaccine is a dose reduced by about 5% as compared to a standard dose. In embodiments, the low dose of p53-targeting vaccine is a dose reduced by 5% as compared to a standard dose. In embodiments, the low dose of p53-targeting vaccine is a dose reduced by about 10% as compared to a standard dose. In embodiments, the low dose of p53-targeting vaccine is a dose reduced by 10% as compared to a standard dose. In embodiments, the low dose of p53-targeting vaccine is a dose reduced by about 20% as compared to a standard dose. In embodiments, the low dose of p53-targeting vaccine is a dose reduced by 20% as compared to a standard dose. In embodiments, the low dose of p53-targeting vaccine is a dose reduced by about 30% as compared to a standard dose. In embodiments, the low dose of p53-targeting vaccine is a dose reduced by 30% as compared to a standard dose. In embodiments, the low dose of p53-targeting vaccine is a dose reduced by about 40% as compared to a standard dose. In embodiments, the low dose of p53-targeting vaccine is a dose reduced by 40% as compared to a standard dose. In embodiments, the low dose of p53-targeting vaccine is a dose reduced by about 50% as compared to a standard dose. In embodiments, the low dose of p53-targeting vaccine is a dose reduced by 50% as compared to a standard dose. In embodiments, the low dose of p53-targeting vaccine is a dose reduced by about 60% as compared to a standard dose. In embodiments, the low dose of p53-targeting vaccine is a dose reduced by 60% as compared to a standard dose. In embodiments, the low dose of p53-targeting vaccine is a dose reduced by about 70% as compared to a standard dose. In embodiments, the low dose of p53-targeting vaccine is a dose reduced by 70% as compared to a standard dose. In embodiments, the low dose of p53-targeting vaccine is a dose reduced by about 80% as compared to a standard dose. In embodiments, the low dose of p53-targeting vaccine is a dose reduced by 80% as compared to a standard dose. In embodiments, the low dose of p53-targeting vaccine is a dose reduced by about 90% as compared to a standard dose. In embodiments, the low dose of p53-targeting vaccine is a dose reduced by 90% as compared to a standard dose.

In embodiments of the methods of treatment described herein, the effective amount of a PD-1 pathway inhibitor is an amount from about 50 mg/kg to about 10 µg/kg. In embodiments, the effective amount of a PD-1 pathway inhibitor is an amount from about 50 mg/kg to about 25 µg/kg. In embodiments, the effective amount of a PD-1 pathway inhibitor is an amount from about 50 mg/kg to about 50 µg/kg. In embodiments, the effective amount of a PD-1 pathway inhibitor is an amount from about 50 mg/kg to about 100 µg/kg. In embodiments, the effective amount of a PD-1 pathway inhibitor is an amount from about 25 mg/kg to about 500 µg/kg. In embodiments, the effective amount of a PD-1 pathway inhibitor is an amount from about 10 mg/kg to about 1 mg/kg. In embodiments, the effective amount of a PD-1 pathway inhibitor is an amount from about 5 mg/kg to about 2 mg/kg. In embodiments, the effective amount of a PD-1 pathway inhibitor is about 50 mg/kg. In embodiments, the effective amount of a PD-1 pathway inhibitor is about 40 mg/kg. In embodiments, the effective amount of a PD-1 pathway inhibitor is about 30 mg/kg. In embodiments, the effective amount of a PD-1 pathway inhibitor is about 20 mg/kg. In embodiments, the effective amount of a PD-1 pathway inhibitor is about 15 mg/kg. In embodiments, the effective amount of a PD-1 pathway inhibitor is about 14 mg/kg. In embodiments, the effective amount of a PD-1 pathway inhibitor is about 13 mg/kg. In embodiments, the effective amount of a PD-1 pathway inhibitor is about 12 mg/kg. In embodiments, the effective amount of a PD-1 pathway inhibitor is about 11 mg/kg. In embodiments, the effective amount of a PD-1 pathway inhibitor is about 10 mg/kg. In embodiments, the effective amount of a PD-1 pathway inhibitor is about 9 mg/kg. In embodiments, the effective amount of a PD-1 pathway inhibitor is about 8 mg/kg. In embodiments, the effective amount of a PD-1 pathway inhibitor is about 7 mg/kg. In embodiments, the effective amount of a PD-1 pathway inhibitor is about 6 mg/kg. In embodiments, the effective amount of a PD-1 pathway inhibitor is about 5 mg/kg. In embodiments, the effective amount of a PD-1 pathway inhibitor is about 4 mg/kg. In embodiments, the effective amount of a PD-1 pathway inhibitor is about 3 mg/kg. In embodiments, the effective amount of a PD-1 pathway inhibitor is about 2 mg/kg. In embodiments, the effective amount of a PD-1 pathway inhibitor is about 1 mg/kg. In embodiments, the effective amount of a PD-1 pathway inhibitor is about 900 µg/kg. In embodiments, the effective amount of a PD-1 pathway inhibitor is about 800 µg/kg. In embodiments, the effective amount of a PD-1 pathway inhibitor is about 700 µg/kg. In embodiments, the effective amount of a PD-1 pathway inhibitor is about 600 µg/kg. In embodiments, the effective amount of a PD-1 pathway inhibitor is about 500 µg/kg. In embodiments, the effective amount of a PD-1 pathway inhibitor is about 400 µg/kg. In embodiments, the effective amount of a PD-1 pathway inhibitor is about 300 µg/kg. In embodiments, the effective amount of a PD-1 pathway inhibitor is about 200 µg/kg. In embodiments, the effective amount of a PD-1 pathway inhibitor is about 100 µg/kg. In embodiments, the effective amount of a PD-1 pathway inhibitor is about 50 µg/kg. In embodiments, the effective amount of a PD-1 pathway inhibitor is about 25 µg/kg. In embodiments, the effective amount of a PD-1 pathway inhibitor is about 10 µg/kg. In embodiments, the effective amount of a PD-1 pathway inhibitor is 50, 40, 30, 20, 15, 14, 13, 12, 11, 10, 9, 8, 7, 6, 5, 4, 3, 2, 1, 0.9, 0.8, 0.7, 0.6, 0.5, 0.4, 0.3, 0.2, 0.1, 0.05, 0.025, or 0.01 mg/kg. For the embodiments recited above, the PD-1 pathway inhibitor may be pembrolizumab, nivolumab, pidilizumab, avelumab, MPDL3280A, durvalumab, BMS-936559, a biosimilar thereof, or any combination thereof. In further embodiments, the PD-1 pathway inhibitor administered according to the embodiments provided herein is co-administered with a p53-targeting vaccine. The amounts provided above are an effective amount of a PD-1 pathway inhibitor provided herein including embodiments thereof. Thus, in embodiments the PD-1 pathway inhibitor is present in an effective amount of 50, 40, 30, 20, 15, 14, 13, 12, 11, 10, 9, 8, 7, 6, 5, 4, 3, 2, 1, 0.9, 0.8, 0.7, 0.6, 0.5, 0.4, 0.3, 0.2, 0.1, 0.05, 0.025, or 0.01 mg/kg.

In embodiments of the methods of treatment described herein, the PD-1 pathway inhibitor is present in an amount from about 1700 mg to about 5 mg. In embodiments, the PD-1 pathway inhibitor is present in an effective amount of about 1700 mg. In embodiments, the PD-1 pathway inhibitor is present in an effective amount of about 1650 mg. In embodiments, the PD-1 pathway inhibitor is present in an effective amount of about 1600 mg. In embodiments, the PD-1 pathway inhibitor is present in an effective amount of about 1550 mg. In embodiments, the PD-1 pathway inhibitor is present in an effective amount of about 1500 mg. In embodiments, the PD-1 pathway inhibitor is present in an effective amount of about 1450 mg. In embodiments, the PD-1 pathway inhibitor is present in an effective amount of about 1400 mg. In embodiments, the PD-1 pathway inhibitor is present in an effective amount of about 1350 mg. In embodiments, the PD-1 pathway inhibitor is present in an effective amount of about 1300 mg. In embodiments, the PD-1 pathway inhibitor is present in an effective amount of about 1250 mg. In embodiments, the PD-1 pathway inhibitor is present in an effective amount of about 1200 mg. In embodiments, the PD-1 pathway inhibitor is present in an effective amount of about 1150 mg. In embodiments, the PD-1 pathway inhibitor is present in an effective amount of about 1100 mg. In embodiments, the PD-1 pathway inhibitor is present in an effective amount of about 1000 mg. In embodiments, the PD-1 pathway inhibitor is present in an effective amount of about 900 mg. In embodiments, the PD-1 pathway inhibitor is present in an effective amount of about 850 mg. In embodiments, the PD-1 pathway inhibitor is present in an effective amount of about 800 mg. In embodiments, the PD-1 pathway inhibitor is present in an effective amount of about 750 mg. In embodiments, the PD-1 pathway inhibitor is present in an effective amount of about 700 mg. In embodiments, the PD-1 pathway inhibitor is present in an effective amount of about 650 mg. In embodiments, the PD-1 pathway inhibitor is present in an effective amount of about 600 mg. In embodiments, the PD-1 pathway inhibitor is present in an effective amount of about 500 mg. In embodiments, the PD-1 pathway inhibitor is present in an effective amount of about 400 mg. In embodiments, the PD-1 pathway inhibitor is present in an effective amount of about 300 mg. In embodiments, the PD-1 pathway inhibitor is present in an effective amount of about 200 mg. In embodiments, the PD-1 pathway inhibitor is present in an effective amount of about 100 mg. In embodiments, the PD-1 pathway inhibitor is present in an effective amount of about 50 mg. In embodiments, the PD-1 pathway inhibitor is present in an effective amount of about 25 mg. In embodiments, the PD-1 pathway inhibitor is present in an effective amount of about 10 mg. In embodiments, the PD-1 pathway inhibitor is present in an effective amount of about 5 mg. In embodiments, the PD-1 pathway inhibitor is present in an effective amount of 1700, 1650, 1600, 1550, 1500, 1450, 1400, 1350, 1300, 1250, 1200, 1150, 1100, 1000, 900, 850, 800, 750, 700, 650, 600, 500, 400, 300, 200, 100, 50, 25, 10, or 5 mg. For the embodiments recited in this paragraph, the PD-1 pathway inhibitor may be pembrolizumab, nivolumab, pidilizumab, avelumab, MPDL3280A, durvalumab, BMS-936559, a biosimilar thereof, or any combination thereof. In further embodiments, the PD-1 pathway inhibitor administered according to the embodiments provided herein may be co-administered with a p53-targeting vaccine. The amounts provided above may be an effective amount of a PD-1 pathway inhibitor provided herein including embodiments thereof. Thus, in embodiments the PD-1 pathway inhibitor is present in an effective amount of 1700, 1650, 1600, 1550, 1500, 1450, 1400, 1350, 1300, 1250, 1200, 1150, 1100, 1000, 900, 850, 800, 750, 700, 650, 600, 500, 400, 300, 200, 100, 50, 25, 10, or 5 mg.

In some embodiments of the methods of treatment described herein, the PD-1 pathway inhibitor is present in a low dose amount. The phrase "low dose" or "low dose amount" of PD-1 pathway inhibitor in the context of an effective amount to treat cancer refers to the use of a particular effective amount of PD-1 pathway inhibitor that is lower than typically used for treating cancer. In certain embodiments, the low dose is about 1/10 of the amount used for treating cancer. In other embodiments, the low dose of is about 1/2, about 1/3, about 1/4, about 1/5, about 1/6, about 1/7, about 1/8, about 1/9, or any range between two of the numbers, of the amount used for treating cancer. In further embodiments, the low dose of PD-1 pathway inhibitor is about 0.9 times, about 0.8 times, about 0.7 times, about 0.6 times, about 0.5 times, about 0.4 times, about 0.3 times, about 0.2 times, about 0.1 times, about 0.09 times, about 0.08 times, about 0.07 times, about 0.06 times, about 0.05 times, about 0.04 times, about 0.03 times, about 0.02 times, about 0.01 times, about 0.009 times, about 0.08 times, about 0.07 times, or any range between two of the numbers, less than the typical amount used for a particular situation (i.e., treating cancer). In still further embodiments, the low dose of PD-1 pathway inhibitor is a dose reduced by about 5%, about 10%, about 20%, about 30%, about 40%, about 50%, about 60%, about 70%, about 80%, about 90%, or any range between two of the numbers as compared to a standard dose. In embodiments, the "low dose" or "low dose amount" is the "effective dose" or "combined effective dose" as described herein.

In embodiments of the methods of treatment described herein, the PD-1 pathway inhibitor is pembrolizumab. In embodiments, the PD-1 antagonist is pembrolizumab. Pembrolizumab is a checkpoint inhibition antibody that binds to the PD-1 molecule expressed by activated T cells and other lymphocytes. In embodiments, pembrolizumab is administered in an effective amount of about 200 mg. In embodiments, pembrolizumab is administered in an effective amount of about 190 mg. In embodiments, pembrolizumab is administered in an effective amount of about 180 mg. In embodiments, pembrolizumab is administered in an effective amount of about 170 mg. In embodiments, pembrolizumab is administered in an effective amount of about 160 mg. In embodiments, pembrolizumab is administered in an effective amount of about 150 mg. In embodiments, pembrolizumab is administered in an effective amount of about 210 mg. In embodiments, pembrolizumab is administered in an effective amount of about 220 mg. In embodiments, pembrolizumab is administered in an effective amount of about 230 mg. In embodiments, pembrolizumab is administered in an effective amount of about 240 mg. In embodiments, pembrolizumab is administered in an effective amount of about 250 mg. In embodiments, pembrolizumab is administered in an effective amount of about 190 mg to about 210 mg. In embodiments, pembrolizumab is administered in an effective amount of about 180 mg to about 220 mg. In embodiments, pembrolizumab is administered in an effective amount of about 170 mg to about 230 mg. In embodiments, pembrolizumab is administered in an effective amount of about 160 mg to about 240 mg. In embodiments, pembrolizumab is administered in an effective amount of about 150 mg to about 250 mg. In embodiments, pembrolizumab is administered in an effective amount of about 140 mg to about 260 mg. In embodiments, pembrolizumab is administered in an effective amount of about 130 mg to about 270 mg. In embodiments, pembrolizumab is administered in an effective amount of about 120 mg to about 280 mg. In embodiments, pembrolizumab is administered in an effective amount of about 110 mg to about 290 mg. In embodiments, pembrolizumab is administered in an effective amount of about 100 mg to about 300 mg. In embodiments, pembrolizumab is administered in an effective amount of about 50 mg to about 400 mg. In embodiments, pembrolizumab is administered in an effective amount of about 1 mg to about 500 mg. In embodiments, pembrolizumab is administered in an effective amount of about 2.0 mg/kg. In embodiments, pembrolizumab is administered in an effective amount of about 1.5 mg/kg to about 2.5 mg/kg. In embodiments, pembrolizumab is administered in an effective amount of about 1.0 mg/kg to about 3.0 mg/kg. In embodiments, pembrolizumab is administered in an effective amount of about 0.5 mg/kg to about 3.5 mg/kg. In embodiments, pembrolizumab is administered in an effective amount of about 0.1 mg/kg to about 5.0 mg/kg. In embodiments, the effective amount of pembrolizumab is administered once every one to four weeks. In embodiments, the effective amount of pembrolizumab is administered once every two to four weeks. In embodiments, the effective amount of pembrolizumab is administered once per week. In embodiments, the effective amount of pembrolizumab is administered once every two weeks. In embodiments, the effective amount of pembrolizumab is administered once every three weeks. the effective amount of pembrolizumab is administered once every four weeks.

In embodiments of the methods of treatment described herein, the PD-1 pathway inhibitor is pidilizumab. In embodiments, the PD-1 antagonist is pidilizumab. In embodiments of the methods of treatment described herein, pidilizumab is administered in an effective amount of about 200 mg. In embodiments, pidilizumab is administered in an effective amount from about 190 mg to about 210 mg. In embodiments, pidilizumab is administered in an effective amount from about 180 mg to about 220 mg. In embodiments, pidilizumab is administered in an effective amount from about 170 mg to about 230 mg. In embodiments, pidilizumab is administered in an effective amount from about 160 mg to about 240 mg. In embodiments, pidilizumab is administered in an effective amount from about 150 mg to about 250 mg. In embodiments, pidilizumab is administered in an effective amount from about 140 mg to about 260 mg. In embodiments, pidilizumab is administered in an effective amount from about 130 mg to about 270 mg. In embodiments, pidilizumab is administered in an effective amount from about 120 mg to about 280 mg. In embodiments, pidilizumab is administered in an effective amount from about 110 mg to about 290 mg. In embodiments, pidilizumab is administered in an effective amount from about 100 mg to about 300 mg. In embodiments, pidilizumab is administered in an effective amount from about 50 mg to about 400 mg. In embodiments, pidilizumab is administered in an effective amount from about 1 mg to about 500 mg. In embodiments, the effective amount of pidilizumab is administered from about once every thirty days to about once every ninety days. In embodiments, the effective amount of pidilizumab is administered from about once every thirty days to about once every sixty days. In embodiments, the effective amount of pidilizumab is administered from about once every forty days to about once every forty-four days. In embodiments, the effective amount of pidilizumab is administered from about once every forty-two days.

In embodiments of the methods of treatment described herein, the PD-1 pathway inhibitor is atezolizumab. In embodiments, the PD-L1 antagonist is atezolizumab. The term "atezolizumab" encompasses biosimilars of atezolizumab. In embodiments, atezolizumab is administered in an effective amount of about 1200 mg. In embodiments, atezolizumab is administered in an effective amount of about 500 mg, 600 mg, 700 mg, 800 mg, 900 mg, 1000 mg, 1100 mg, 1200 mg, 1300 mg, 1400 mg, 1500 mg, 1600 mg, 1700 mg, 18000 mg, 1900 mg, or 2000 mg. In embodiments, atezolizumab is administered in an effective amount from about 500 mg to about 2000 mg. In embodiments, atezolizumab is administered in an effective amount from about 1150 mg to about 1250 mg. In embodiments, atezolizumab is administered in an effective amount from about 1100 mg to about 1300 mg. In embodiments, atezolizumab is administered in an effective amount from about 1000 mg to about 1400 mg. In embodiments, atezolizumab is administered in an effective amount from about 900 mg to about 1500 mg. In embodiments, atezolizumab is administered in an effective amount from about 800 mg to about 1600 mg. In embodiments, atezolizumab is administered in an effective amount from about 700 mg to about 1700 mg. In embodiments, atezolizumab is administered in an effective amount from about 600 mg to about 1800 mg. In embodiments, atezolizumab is administered in an effective amount from about 500 mg to about 1900 mg. In embodiments, the effective amount of atezolizumab is administered once every one to four weeks. In embodiments, the effective amount of atezolizumab is administered once every two to four weeks. In embodiments, the effective amount of atezolizumab is administered once per week. In embodiments, the effective amount of atezolizumab is administered once every two weeks. In embodiments, the effective amount of atezolizumab is administered once every three weeks. In embodiments, the effective amount of atezolizumab is administered once every four weeks.

In embodiments of the methods of treatment described herein, the PD-1 pathway inhibitor is durvalumab. In embodiments, the PD-L1 antagonist is durvalumab. In embodiments of the methods of treatment described herein, durvalumab is administered in an effective amount from about 1 mg/kg to about 25 mg/kg. In embodiments, durvalumab is administered in an effective amount from about 5 mg/kg to about 15 mg/kg. In embodiments, durvalumab is administered in an effective amount from about 8 mg/kg to about 12 mg/kg. In embodiments, durvalumab is administered in an effective amount from about 9 mg/kg to about 11 mg/kg. In embodiments, durvalumab is administered in an effective amount of about 5 mg/kg. In embodiments, durvalumab is administered in an effective amount of about 6 mg/kg. In embodiments, durvalumab is administered in an effective amount of about 7 mg/kg. In embodiments, durvalumab is administered in an amount of about 8 mg/kg. In embodiments, durvalumab is administered in an amount of about 9 mg/kg. In embodiments, durvalumab is administered in an effective amount of about 10 mg/kg. In embodiments, durvalumab is administered in an effective amount of about 11 mg/kg. In embodiments, durvalumab is administered in an effective amount of about 12 mg/kg. In embodiments, durvalumab is administered in an effective amount of about 13 mg/kg. In embodiments, durvalumab is administered in an effective amount of about 14 mg/kg. In embodiments, durvalumab is administered in an effective amount of about 15 mg/kg. In embodiments, durvalumab is administered in an effective amount of 5, 6, 7, 8, 9, 10, 11, 12, 13, 14, or 15 mg/kg. When the subject being treated weighs less than 30 kg, durvalumab may be administered in an effective amount of 10 mg/kg. In embodiments, durvalumab is administered in an effective amount from about 600 mg to about 1650 mg. In embodiments, durvalumab is administered in an effective amount from about 600 mg to about 1000 mg. In embodiments, durvalumab is administered in an effective amount from about 700 mg to about 800 mg. In embodiments, durvalumab is administered in an effective amount from about 1400 mg to about 1600 mg. In embodiments, durvalumab is administered in an effective amount of about 600 mg. In embodiments, durvalumab is administered in an effective amount of about 700 mg. In embodiments, durvalumab is administered in an effective amount of about 710 mg. In embodiments, durvalumab is administered in an effective amount of about 720 mg. In embodiments, durvalumab is administered in an effective amount of about 730 mg. In embodiments, durvalumab is administered in an effective amount of about 740 mg. In embodiments, durvalumab is administered in an effective amount of about 750 mg. In embodiments, durvalumab is administered in an effective amount of about 760 mg. In embodiments, durvalumab is administered in an effective amount of about 770 mg. In embodiments, durvalumab is administered in an effective amount of about 780 mg. In embodiments, durvalumab is administered in an effective amount of about 790 mg. In embodiments, durvalumab is administered in an effective amount of about 800 mg. In embodiments, durvalumab is administered in an effective amount of about 900 mg. In embodiments, In embodiments, durvalumab is administered in an effective amount of about 1000 mg. In embodiments, durvalumab is administered in an effective amount of about 1100 mg. In embodiments, durvalumab is administered in an effective amount of about 1200 mg. In embodiments, durvalumab is administered in an effective amount of about 1300 mg. In embodiments, durvalumab is administered in an effective amount of about 1400 mg. In embodiments, durvalumab is administered in an effective amount of about 1450 mg. In embodiments, durvalumab is administered in an effective amount of about 1460 mg. In embodiments, durvalumab is administered in an effective amount of about 1470 mg. In embodiments, durvalumab is administered in an effective amount of about 1480 mg. In embodiments, durvalumab is administered in an effective amount of about 1490 mg. In embodiments, durvalumab is administered in an effective amount of about 1500 mg. In embodiments, durvalumab is administered in an effective amount of about 1510 mg. In embodiments, durvalumab is administered in an effective amount of about 1520 mg. In embodiments, durvalumab is administered in an effective amount of about 1530 mg. In embodiments, durvalumab is administered in an effective amount of about 1540 mg. In embodiments, durvalumab is administered in an effective amount of about 1550 mg. In embodiments, durvalumab is administered in an effective amount of about 1650 mg. In embodiments, durvalumab is administered in an effective amount of 600, 700, 710, 720, 730, 740, 750, 760, 770, 780, 790, 800, 900, 1000, 1100, 1200, 1300, 1400, 1450, 1460, 1470, 1480, 1490, 1500, 1510, 1520, 1530, 1540, 1550, 1650 mg. In embodiments, the effective amount of durvalumab is administered once every one to four weeks. In embodiments, the effective amount of durvalumab is administered once every two to four weeks. In embodiments, the effective amount of durvalumab is administered once every week. In embodiments, the effective amount of durvalumab is administered once every two weeks. In embodiments, the effective amount of durvalumab is administered once every three weeks. the effective amount of durvalumab is administered once every four weeks.

In embodiments of the methods of treatment described herein, the PD-1 pathway inhibitor is nivolumab. In embodiments, the PD-1 antagonist is nivolumab. In embodiments of the methods of treatment described herein, the effective amount of nivolumab is about 240 mg. In embodiments, the effective amount of nivolumab is from about 230 mg to about 250 mg. In embodiments, the effective amount of nivolumab is from about 220 mg to about 260 mg. In embodiments, the effective amount of nivolumab is from about 210 mg to about 270 mg. In embodiments, the effective amount of nivolumab is from about 200 mg to about 280 mg. In embodiments, the effective amount of nivolumab is from about 190 mg to about 290 mg. In embodiments, the effective amount of nivolumab is from about 180 mg to about 300 mg. In embodiments, the effective amount of nivolumab is from about 170 mg to about 310 mg. In embodiments, the effective amount of nivolumab is from about 100 mg to about 500 mg. In embodiments, the effective amount of nivolumab is about 3 mg/kg. In embodiments, the effective amount of nivolumab is from about 2.5 mg/kg to about 3.5 mg/kg. In embodiments, the effective amount of nivolumab is from about 2.0 mg/kg to about 4.0 mg/kg. In embodiments, the effective amount of nivolumab is from about 1.5 mg/kg to about 4.5 mg/kg. In embodiments, the effective amount of nivolumab is from about 1.0 mg/kg to about 5.0 mg/kg. In embodiments, the effective amount of nivolumab is from about 0.5 mg/kg to about 5.5 mg/kg. In embodiments, the effective amount of nivolumab is from about 0.1 mg/kg to about 10 mg/kg. In embodiments, the effective amount of nivolumab is administered once every one to four weeks. In embodiments, the effective amount of nivolumab is administered once every two to four weeks. In embodiments, the effective amount of nivolumab is administered once every week. In embodiments, the effective amount of nivolumab is administered once every two weeks. In embodiments, the effective amount of nivolumab is administered once every three weeks. the effective amount of nivolumab is administered once every four weeks.

In embodiments of the methods of treatment described herein, the PD-1 pathway inhibitor is avelumab. In embodiments, the PD-L1 antagonist is avelumab. In embodiments of the methods of treatment described herein, avelumab is administered in an effective amount from about 5 mg/kg to 15 mg/kg. In embodiments, avelumab is administered in an effective amount of about 5 mg/kg. In embodiments, avelumab is administered in an effective amount of about 6 mg/kg. In embodiments, avelumab is administered in an effective amount of about 7 mg/kg. In embodiments, avelumab is administered in an effective amount of about 8 mg/kg. In embodiments, avelumab is administered in an effective amount of about 9 mg/kg. In embodiments, avelumab is administered in an effective amount of about 10 mg/kg. In embodiments, avelumab is administered in an effective amount of about 11 mg/kg. In embodiments, avelumab is administered in an effective amount of about 12 mg/kg. In embodiments, avelumab is administered in an effective amount of about 13 mg/kg. In embodiments, avelumab is administered in an effective amount of about 14 mg/kg. In embodiments, avelumab is administered in an effective amount of about 15 mg/kg. In embodiments, avelumab is administered in an effective amount of 5, 6, 7, 8, 9, 10, 11, 12, 13, 14, or 15 mg/kg. In embodiments, avelumab is administered in an effective amount from about 5 mg/kg to about 15 mg/kg. In embodiments, avelumab is administered in an effective amount from about 1 mg/kg to about 20 mg/kg. In embodiments, avelumab is administered in an effective amount of 0.5 mg/kg to about 25 mg/kg. In embodiments, the effective amount of avelumab is administered once every one to four weeks. In embodiments, the effective amount of avelumab is administered once every two to four weeks. In embodiments, the effective amount of avelumab is administered once every week. In embodiments, the effective amount of avelumab is administered once every two weeks. In embodiments, the effective amount of avelumab is administered once every three weeks. the effective amount of avelumab is administered once every four weeks.

In embodiments of the methods of treatment described herein, the PD-1 pathway inhibitor is AMP-224. In embodiments, the PD-1 antagonist is AMP-224. In embodiments of the methods of treatment described herein, AMP-224 is administered in an effective amount from about 1 mg/kg to about 100 mg/kg. In embodiments, AMP-224 is administered in an effective amount from about 1 mg/kg to about 50 mg/kg. In embodiments, AMP-224 is administered in an effective amount from about 1 mg/kg to about 20 mg/kg. In embodiments, AMP-224 is administered in an effective amount from about 5 mg/kg to about 15 mg/kg. In embodiments, AMP-224 is administered in an effective amount of about 10 mg/kg. In embodiments, the effective amount of AMP-224 is administered once every one to four weeks. In embodiments, the effective amount of AMP-224 is administered once every two to four weeks. In embodiments, the effective amount of AMP-224 is administered once per week. In embodiments, the effective amount of AMP-224 is administered once every two weeks. In embodiments, the effective amount of AMP-224 is administered once every three weeks. In embodiments, the effective amount of AMP-224 is administered once every four weeks.

In embodiments of the methods of treatment described herein, the PD-1 pathway inhibitor is BMS-963559. In embodiments, the PD-L1 antagonist is BMS-963559. In embodiments of the methods of treatment described herein, BMS-936559 is administered in an effective amount from about 0.1 mg/kg to about 10 mg/kg. In embodiments, BMS-936559 is administered in an effective amount f about 0.1 mg/kg. In embodiments, BMS-936559 is administered in an effective amount of about 0.2 mg/kg. In embodiments, BMS-936559 is administered in an effective amount of about 0.3 mg/kg. In embodiments, BMS-936559 is administered in an effective amount of about 0.4 mg/kg. In embodiments, BMS-936559 is administered in an effective amount of about 0.5 mg/kg. In embodiments, BMS-936559 is administered in an effective amount of about 0.6 mg/kg. In embodiments, BMS-936559 is administered in an effective amount of about 0.7 mg/kg. In embodiments, BMS-936559 is administered in an effective amount of about 0.8 mg/kg. In embodiments, BMS-936559 is administered in an effective amount of about 0.9 mg/kg. In embodiments, BMS-936559 is administered in an effective amount of about 1 mg/kg. In embodiments, BMS-936559 is administered in an effective amount of about 2 mg/kg. In embodiments, BMS-936559 is administered in an effective amount of about 3 mg/kg. In embodiments, BMS-936559 is administered in an effective amount of about 4 mg/kg. In embodiments, BMS-936559 is administered in an effective amount of about 5 mg/kg. In embodiments, BMS-936559 is administered in an effective amount of about 6 mg/kg. In embodiments, BMS-936559 is administered in an effective amount of about 7 mg/kg. In embodiments, BMS-936559 is administered in an effective amount of about 8 mg/kg. In embodiments, BMS-936559 is administered in an effective amount of about 9 mg/kg. In embodiments, BMS-936559 is administered in an effective amount of about 10 mg/kg. In embodiments, BMS-936559 is administered in an effective amount of 0.1, 0.2, 0.3, 0.4, 0.5, 0.6, 0.7, 0.8, 0.9, 1, 2, 3, 4, 5, 6, 7, 8, 9, or 10 mg/kg. In embodiments, the effective amount of BMS-936559 is administered once every one to four weeks. In embodiments, the effective amount of BMS-936559 is administered once every two to four weeks. In embodiments, the effective amount of BMS-936559 is administered once every week. In embodiments, the effective amount of BMS-936559 is administered once every two weeks. In embodiments, the effective amount of BMS-936559 is administered once every three weeks. the effective amount of BMS-936559 is administered once every four weeks.

In embodiments of the methods of treatment described herein, the combined effective amount of a p53-targeting vaccine is about $5.0 \times 10^8$ pfu and the combined effective amount of a PD-1 pathway inhibitor is about 2 mg/kg. In embodiments, the combined effective amount of a p53-targeting vaccine is about $5.1 \times 10^8$ pfu and the combined effective amount of a PD-1 pathway inhibitor is about 2 mg/kg. In embodiments, the combined effective amount of a p53-targeting vaccine is about $5.2 \times 10^8$ pfu and the combined effective amount of a PD-1 pathway inhibitor is about 2 mg/kg. In embodiments, the combined effective amount of a p53-targeting vaccine is about $5.3 \times 10^8$ pfu and the combined effective amount of a PD-1 pathway inhibitor is about 2 mg/kg. In embodiments, the combined effective amount of a p53-targeting vaccine is about $5.4 \times 10^8$ pfu and the combined effective amount of a PD-1 pathway inhibitor is about 2 mg/kg. In embodiments, the combined effective amount of a p53-targeting vaccine is about $5.5 \times 10^8$ pfu and the combined effective amount of a PD-1 pathway inhibitor is about 2 mg/kg. In embodiments, the combined effective amount of a p53-targeting vaccine is about $5.6 \times 10^8$ pfu and the combined effective amount of a PD-1 pathway inhibitor is about 2 mg/kg. In embodiments, the combined effective amount of a p53-targeting vaccine is about $5.7 \times 10^8$ pfu and the combined effective amount of a PD-1 pathway inhibitor is about 2 mg/kg. In embodiments, the combined effective amount of a p53-targeting vaccine is about $5.8 \times 10^8$ pfu and the combined effective amount of a PD-1 pathway inhibitor is about 2 mg/kg. In embodiments, the combined effective amount of a p53-targeting vaccine is about $5.9 \times 10^8$ pfu and the combined effective amount of a PD-1 pathway inhibitor is about 2 mg/kg. In embodiments, the combined effective amount of a p53-targeting vaccine is about $6 \times 10^8$ pfu and the combined effective amount of a PD-1 pathway inhibitor is about 2 mg/kg.

In embodiments of the methods of treatment described herein, the combined effective amount of a p53-targeting vaccine is about $2.0 \times 10^8$ pfu and the combined effective amount of a PD-1 pathway inhibitor is about 2 mg/kg. In embodiments, the combined effective amount of a p53-targeting vaccine is about $2.1 \times 10^8$ pfu and the combined effective amount of a PD-1 pathway inhibitor is about 2 mg/kg. In embodiments, the combined effective amount of a p53-targeting vaccine is about $2.2 \times 10^8$ pfu and the combined effective amount of a PD-1 pathway inhibitor is about 2 mg/kg. In embodiments, the combined effective amount of a p53-targeting vaccine is about $2.3 \times 10^8$ pfu and the combined effective amount of a PD-1 pathway inhibitor is about 2 mg/kg. In embodiments, the combined effective amount of a p53-targeting vaccine is about $2.4 \times 10^8$ pfu and the combined effective amount of a PD-1 pathway inhibitor is about 2 mg/kg. In embodiments, the combined effective amount of a p53-targeting vaccine is about $2.5 \times 10^8$ pfu and the combined effective amount of a PD-1 pathway inhibitor is about 2 mg/kg. In embodiments, the combined effective amount of a p53-targeting vaccine is about $2.6 \times 10^8$ pfu and the combined effective amount of a PD-1 pathway inhibitor is about 2 mg/kg. In embodiments, the combined effective amount of a p53-targeting vaccine is about $2.7 \times 10^8$ pfu and the combined effective amount of a PD-1 pathway inhibitor is about 2 mg/kg. In embodiments, the combined effective amount of a p53-targeting vaccine is about $2.8 \times 10^8$ pfu and the combined effective amount of a PD-1 pathway inhibitor is about 2 mg/kg. In embodiments, the combined effective amount of a p53-targeting vaccine is about $2.9 \times 10^8$ pfu and the combined effective amount of a PD-1 pathway inhibitor is about 2 mg/kg. In embodiments, the combined effective amount of a p53-targeting vaccine is about $3 \times 10^8$ pfu and the combined effective amount of a PD-1 pathway inhibitor is about 2 mg/kg.

In embodiments, the combined effective amount of a p53-targeting vaccine is about $5.6 \times 10^8$ pfu and the combined effective amount of a PD-1 pathway inhibitor is about 2 mg/kg. In embodiments, the combined effective amount of a p53-targeting vaccine is about $2.8 \times 10^8$ pfu and the combined effective amount of a PD-1 pathway inhibitor is about 2 mg/kg.

In one embodiment of the methods of treatment described herein, the first PD-1 pathway inhibitor is pembrolizumab, and the second PD-1 pathway inhibitor is atezolizumab, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 1200 mg.

In one embodiment of the methods of treatment described herein, the first PD-1 pathway inhibitor is pembrolizumab, and the second PD-1 pathway inhibitor is atezolizumab, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 1200 mg.

In one embodiment of the methods of treatment described herein, the first PD-1 pathway inhibitor is pembrolizumab, and the second PD-1 pathway inhibitor is durvalumab, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 10 mg/kg.

In one embodiment of the methods of treatment described herein, the first PD-1 pathway inhibitor is pembrolizumab, and the second PD-1 pathway inhibitor is durvalumab, and the combined effective amount of the p53-targetting vaccine is $5.6 \times 10^8$ pfu, the combined effective amount of the first PD-1 pathway inhibitor is 2 mg/kg and the combined effective amount of the second PD-1 pathway inhibitor is 750 mg.

In one embodiment of the methods of treatment described herein, the first PD-1 pathway inhibitor is pembrolizumab, and the second PD-1 pathway inhibitor is durvalumab, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 1500 mg.

In one embodiment of the methods of treatment described herein, the first PD-1 pathway inhibitor is pembrolizumab, and the second PD-1 pathway inhibitor is durvalumab, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 10 mg/kg.

In one embodiment of the methods of treatment described herein, the first PD-1 pathway inhibitor is pembrolizumab, and the second PD-1 pathway inhibitor is durvalumab, and the combined effective amount of the p53-targetting vaccine is $2.8 \times 10^8$ pfu, the combined effective amount of the first PD-1 pathway inhibitor is 2 mg/kg and the combined effective amount of the second PD-1 pathway inhibitor is 750 mg.

In one embodiment of the methods of treatment described herein, the first PD-1 pathway inhibitor is pembrolizumab, and the second PD-1 pathway inhibitor is durvalumab, and the combined effective amount of the p53-targetting vaccine is $2.8 \times 10^8$ pfu, the combined effective amount of the first PD-1 pathway inhibitor is 2 mg/kg and the combined effective amount of the second PD-1 pathway inhibitor is 1500 mg.

In one embodiment of the methods of treatment described herein, the first PD-1 pathway inhibitor is pembrolizumab, and the second PD-1 pathway inhibitor is avelumab, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 10 mg/kg.

In one embodiment of the methods of treatment described herein, the first PD-1 pathway inhibitor is pembrolizumab, and the second PD-1 pathway inhibitor is avelumab, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 10 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 0.1 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 0.3 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 1 mg/kg.

In one embodiment of the methods of treatment described herein, the first PD-1 pathway inhibitor is pembrolizumab, and the second PD-1 pathway inhibitor is BMS-936559, and wherein the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 3 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 2 mg/kg, and the combined effective amount of the second PD-1 pathway inhibitor is 10 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 0.1 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 0.3 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 1 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 3 mg/kg.

In one embodiment of the methods of treatment described herein, the first PD-1 pathway inhibitor is pembrolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 2 mg/kg, and the combined effective amount of the second PD-1 pathway inhibitor is 10 mg/kg.

In one embodiment of the methods of treatment described herein, the first PD-1 pathway inhibitor is atezolizumab, and the second PD-1 pathway inhibitor is durvalumab, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 10 mg/kg.

In one embodiment of the methods of treatment described herein, the first PD-1 pathway inhibitor is atezolizumab, and the second PD-1 pathway inhibitor is durvalumab, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 750 mg.

In one embodiment of the methods of treatment described herein, the first PD-1 pathway inhibitor is atezolizumab, and the second PD-1 pathway inhibitor is durvalumab, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 1500 mg.

In one embodiment of the methods of treatment described herein, the first PD-1 pathway inhibitor is atezolizumab, and the second PD-1 pathway inhibitor is durvalumab, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 10 mg/kg.

In one embodiment of the methods of treatment described herein, the first PD-1 pathway inhibitor is atezolizumab, and the second PD-1 pathway inhibitor is durvalumab, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 750 mg.

In one embodiment of the methods of treatment described herein, the first PD-1 pathway inhibitor is atezolizumab, and the second PD-1 pathway inhibitor is durvalumab, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 1500 mg.

In one embodiment of the methods of treatment described herein, the first PD-1 pathway inhibitor is atezolizumab, and the second PD-1 pathway inhibitor is avelumab, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 10 mg/kg.

In one embodiment of the methods of treatment described herein, the first PD-1 pathway inhibitor is atezolizumab, and the second PD-1 pathway inhibitor is avelumab, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 10 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 0.1 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 0.3 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 1 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 3 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 1200 mg, and the combined effective amount of the second PD-1 pathway inhibitor is 10 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 0.1 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 0.3 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 1 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 3 mg/kg.

In one embodiment of the methods of treatment described herein, the first PD-1 pathway inhibitor is atezolizumab, and the second PD-1 pathway inhibitor is BMS-936559, and the combined effective amount of the p53-targetting vaccine is $2.8 \times 10^8$ pfu, the combined effective amount of the first PD-1 pathway inhibitor is 1200 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is avelumab, and the combined effective amount of the p53-targetting vaccine is $5.6 \times 10^8$ pfu, the combined effective amount of the first PD-1 pathway inhibitor is 10 mg/kg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is avelumab, and the combined effective amount of the p53-targetting vaccine is $5.6 \times 10^8$ pfu, the combined effective amount of the first PD-1 pathway inhibitor is 750 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is avelumab, and the combined effective amount of the p53-targetting vaccine is $5.6 \times 10^8$ pfu, the combined effective amount of the first PD-1 pathway inhibitor is 1500 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is avelumab, and the combined effective amount of the p53-targetting vaccine is $2.8 \times 10^8$ pfu, the combined effective amount of the first PD-1 pathway inhibitor is 10 mg/kg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is avelumab, and the combined effective amount of the p53-targetting vaccine is $2.8 \times 10^8$ pfu, the combined effective amount of the first PD-1 pathway inhibitor is 750 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is avelumab, and the combined effective amount of the p53-targetting vaccine is $2.8 \times 10^8$ pfu, the combined effective amount of the first PD-1 pathway inhibitor is 1500 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is $5.6 \times 10^8$ pfu, the combined effective amount of the first PD-1 pathway inhibitor is 10 mg/kg, and the combined effective amount of the second PD-1 pathway inhibitor is 0.1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 0.3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 750 mg, and the combined effective amount of the second PD-1 pathway inhibitor is 0.1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 750 mg, and the combined effective amount of the second PD-1 pathway inhibitor is 0.3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 750 mg, and the combined effective amount of the second PD-1 pathway inhibitor is 1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 750 mg, and the combined effective amount of the second PD-1 pathway inhibitor is 3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 750 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 1500 mg, and the combined effective amount of the second PD-1 pathway inhibitor is 0.1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 1500 mg, and the combined effective amount of the second PD-1 pathway inhibitor is 0.3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 1500 mg, and the combined effective amount of the second PD-1 pathway inhibitor is 1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 1500 mg, and the combined effective amount of the second PD-1 pathway inhibitor is 3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 5.6×10⁸ pfu, the combined effective amount of the first PD-1 pathway inhibitor is 1500 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 0.1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 0.3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 750 mg, and the combined effective amount of the second PD-1 pathway inhibitor is 0.1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 750 mg, and the combined effective amount of the second PD-1 pathway inhibitor is 0.3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 750 mg, and the combined effective amount of the second PD-1 pathway inhibitor is 1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 750 mg, and the combined effective amount of the second PD-1 pathway inhibitor is 3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 750 mg, and the combined effective amount of the second PD-1 pathway inhibitor is 10 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 1500 mg, and the combined effective amount of the second PD-1 pathway inhibitor is 0.1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 1500 mg, and the combined effective amount of the second PD-1 pathway inhibitor is 0.3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 1500 mg, and the combined effective amount of the second PD-1 pathway inhibitor is 1 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 1500 mg, and the combined effective amount of the second PD-1 pathway inhibitor is 3 mg/kg.

In one embodiment of the methods of treatment described herein, the first PD-1 pathway inhibitor is durvalumab, and the second PD-1 pathway inhibitor is BMS-936559, and the combined effective amount of the p53-targetting vaccine is 2.8×10⁸ pfu, the combined effective amount of the first PD-1 pathway inhibitor is 1500 mg, and the combined effective amount of the second PD-1 pathway inhibitor is 10 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 0.1 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 0.3 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 1 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 3 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 5.6×10⁸ pfu, the combined effective amount of the first PD-1 pathway inhibitor is 10 mg/kg, and the combined effective amount of the second PD-1 pathway inhibitor is 10 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 0.1 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 0.3 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 1 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 3 mg/kg.

In one embodiment of the methods of treatment described herein, the first PD-1 pathway inhibitor is avelumab, and the second PD-1 pathway inhibitor is BMS-936559, and the combined effective amount of the p53-targetting vaccine is 2.8×10⁸ pfu, the combined effective amount of the first PD-1 pathway inhibitor is 10 mg/kg, and the combined effective amount of the second PD-1 pathway inhibitor is 10 mg/kg.

In embodiments, the PD-1 pathway inhibitor potentiates anti-tumor activity of the p53-targeting vaccine. The term "potentiates" as used herein refers to the ability of a second therapeutic agent (e.g., a p-53 targeting vaccine as provided herein) to increase the effectiveness of a first therapeutic agent (e.g., a PD-1 pathway inhibitor as provided herein) relative to the absence of said second therapeutic agent (e.g., a p-53 targeting vaccine as provided herein).

In embodiments of the methods of treatment described herein, the effective amount of a p53-targeting vaccine and the effective amount of a PD-1 pathway inhibitor are a combined additive amount.

A "combined additive amount" as used herein refers to the sum of a first amount (e.g., an effective amount of a p53-targeting vaccine) and a second amount (e.g., an effective amount of a PD-1 pathway inhibitor), and, optionally, a third amount (e.g., an effective amount of a PD-1 pathway inhibitor), that results in an additive effect (i.e. an effect equal to the sum of the effects). Therefore, the terms "additive", "combined additive amount", and "additive therapeutic effect" which are used herein interchangeably, refer to a measured effect of compounds administered in combination where the measured effect is equal to the sum of the individual effects of each of the compounds administered alone as a single agent.

In embodiments of the methods of treatment described herein, the effective amount of a p53-targeting vaccine and the effective amount of a PD-1 pathway inhibitor are a combined synergistic amount.

A "combined synergistic amount" as used herein refers to the sum of a first amount (e.g., an effective amount of a p53-targeting vaccine) and a second amount (e.g., an effective amount of a PD-1 pathway inhibitor), and, optionally, a third amount (e.g., an effective amount of a PD-1 pathway inhibitor), that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments of the methods of treatment described herein, an effective amount of one or more PD-1 pathway inhibitors is administered. In embodiments, an effective amount of a first PD-1 pathway inhibitor and an effective amount of a second PD-1 pathway inhibitor is administered. In embodiments, the first PD-1 pathway inhibitor is a PD-1 antagonist and the second PD-1 pathway inhibitor is a PD-L1 antagonist. In embodiments, the first PD-1 pathway inhibitor binds to a PD-1 receptor and the second PD-1 pathway inhibitor binds to PD-L1.

In embodiments of the methods of treatment described herein, the effective amount of a first PD-1 pathway inhibitor and the effective amount of a second PD-1 pathway inhibitor are a combined additive amount.

In embodiments of the methods of treatment described herein, the effective amount of a first PD-1 pathway inhibitor and the effective amount of a second PD-1 pathway inhibitor are a combined synergistic amount.

Administration

"Administration," "administering" and the like, when used in connection with a composition of the invention refer both to direct administration, which may be administration to cells in vitro, administration to cells in vivo, administration to a subject by a medical professional or by self-administration by the subject and/or to indirect administration, which may be the act of prescribing a composition of the invention. When used herein in reference to a cell, refers to introducing a composition to the cell. Typically, an effective amount is administered, as described herein, and which amount can be determined by one of skill in the art. Any method of administration may be used. Compounds (e.g., drugs and antibodies) may be administered to the cells by, for example, addition of the compounds to the cell culture media or injection in vivo. Administration to a subject can be achieved by, for example, intravascular injection, direct intratumoral delivery, and the like.

Administering may mean oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

In embodiments of the methods of treatment described herein, the p53-targeting vaccines and PD-1 pathway inhibitors are administered to a subject parenterally. In embodiments, the p53-targeting vaccines and PD-1 pathway inhibitors are administered to a subject by injection. In embodiments, the p53-targeting vaccines and PD-1 pathway inhibitors are administered to a subject by subcutaneous injection. In embodiments, the p53-targeting vaccines are administered to a subject by subcutaneous injection. In embodiments, the p53-targeting vaccines and PD-1 pathway inhibitors are administered to a subject by intravenous injection. In embodiments, the p53-targeting vaccines and PD-1 pathway inhibitors are administered to a subject by intravenous infusion. In embodiments, the p53-targeting vaccines and PD-1 pathway inhibitors are administered to a subject by infusion. In embodiments, the PD-1 pathway inhibitors are administered to a subject by intravenous injection. In embodiments, the PD-1 pathway inhibitors are administered to a subject by intravenous infusion. In embodiments, the PD-1 pathway inhibitors are administered to a subject by infusion. In embodiments, the PD-1 pathway inhibitors are administered to a subject by intratumoral injection (direct injection into a tumor). In embodiments, the PD-1 pathway inhibitors are administered to a subject by intratumoral perfusion (perfusion into a tumor). Other modes of injection that can be used for the p53-targeting vaccines and PD-1 pathway inhibitors described herein include intra-arterial injection, intra-arterial infusion, intramuscular injection, intravascular injections, intratumoral injection, intraperitoneal injection, intracranial injection, intradermal, intralesional injection, intrathecal injection, and the like. The skilled artisan will appreciate that administration by infusion may occur over a sufficient period of time.

In one embodiment, the p53-targeting vaccine, PD-1 pathway inhibitor, or both are administered systemically or locally (e.g. intratumoral injection, intravenous injection, subcutaneous injection) at intervals of 6 hours, 12 hours, daily or every other day or on a weekly or monthly basis to elicit the desired benefit or otherwise provide a therapeutic effect. In another embodiment, the p53-targeting vaccine, PD-1 pathway inhibitor, or both are administered as required to elicit the desired benefit or otherwise provide a therapeutic effect.

In some embodiments of the methods of treatment described herein, the p53-targeting vaccine and PD-1 are administered sequentially. In other embodiments, the p53-targeting vaccine and PD-1 are administered concurrently. During the course of treatment the p53-targeting vaccine and PD-1 may at times be administered sequentially and at other times be administered concurrently. In one embodiment, at least one dose of PD-1 is administered without a concurrent or substantially concurrent dose of the p53-targeting vaccine.

The terms "concurrent" or "substantially concurrent" in connection with administration are used in their customary sense. Particularly, concurrent or substantially concurrent refer to contemporaneous administration wherein two therapeutic agents are administered simultaneously or with temporal proximity, respectively. For example, a dose of PD-1 pathway inhibitor and a dose of p53-targeting vaccine may be delivered simultaneously or with one dose preceding the second dose by a short window of time (e.g., less than 10, 30, 60, 90, or 120 minutes).

In some embodiments of the methods of treatment described herein, p53-targeting vaccine and PD-1 are admixed together prior to administration.

In one embodiment of the methods of treatment described herein, a response rate to the p53 vaccine is reduced as compared to baseline reference or control reference. The term "response rate" is used herein in its customary sense to indicate the percentage of patients who respond with cancer recession following treatment. Response rates include, for example, partial or complete recession. A partial response includes an about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, or about 99% recession of cancer cells. In some embodiments, the control reference is obtained from a healthy subject, a cancer subject (e.g., the cancer subject being treated or another cancer subject), or any population thereof.

In some embodiments of the methods of treatment described herein, the subject is administered a single dose of the p53-targeting vaccine, PD-1 pathway inhibitor, or both. In other embodiments, the subject is administered multiple doses of the p53-targeting vaccine, the PD-1 pathway inhibitor, or both. For example, the subject is administered 2, 3, 4, 5, 6, 7, 8, 9, 10, or more doses of the p53-targeting vaccine, the PD-1 pathway inhibitor, or both. In some embodiments, the subject is administered 2, 3, 4, 5, or 6 doses of the p53-targeting vaccine. In one preferred embodiment, the subject is administered 3 doses of the p53-targeting vaccine. In some embodiments, the subject is administered a maximum of 4, 5, 6, 7, 8, 9, or 10 doses of the PD-1 pathway inhibitor. In one preferred embodiment, the subject is administered a maximum of 7 doses of the PD-1 pathway inhibitor.

In some embodiments of the methods of treatment described herein, the p53-targeting vaccine and PD-1 pathway inhibitor are administered at the same time or at substantially the same time. In other embodiments, the p53-targeting vaccine and PD-1 pathway inhibitor are administered separately. During the course of treatment the p53-targeting vaccine and PD-1 pathway inhibitor may at times be administered at the same time (or substantially the same time) and at other times separately. For example, the p53-targeting vaccine and PD-1 pathway inhibitor can be administered at the same time for 1, 2, 3, 4, 5, 6, or 7 consecutive doses followed by 1, 2, 3, 4, 5, 6, or 7 doses of the p53-targeting vaccine or PD-1 pathway inhibitor, and any combination thereof. In some embodiments, the p53-targeting vaccine is administered for one dose or a plurality of doses prior to administration of the first dose of PD-1 pathway inhibitor. In other embodiments, the PD-1 pathway inhibitor is administered for one dose or a plurality of doses prior to administration of the first dose of p53-targeting vaccine.

In one embodiment of the methods of treatment described herein, the treatment with a p53-targeting vaccine and PD-1 pathway inhibitor combination therapy will extend over a period, for example, of about 1 day to about 52 weeks, about 1 day to about 26 weeks, about 1 day to about 16 weeks, about 1 day to about 12 weeks, about 1 day to about 10 weeks, about 1 day to about 5 weeks, about 1 week to about 4 weeks, about 2 weeks to about 3 weeks, about 1 day to about 2 weeks, about 1 week, about 1 to 6 days, about 1 to 4 days, or about 1 to 2 days.

Figure 3:
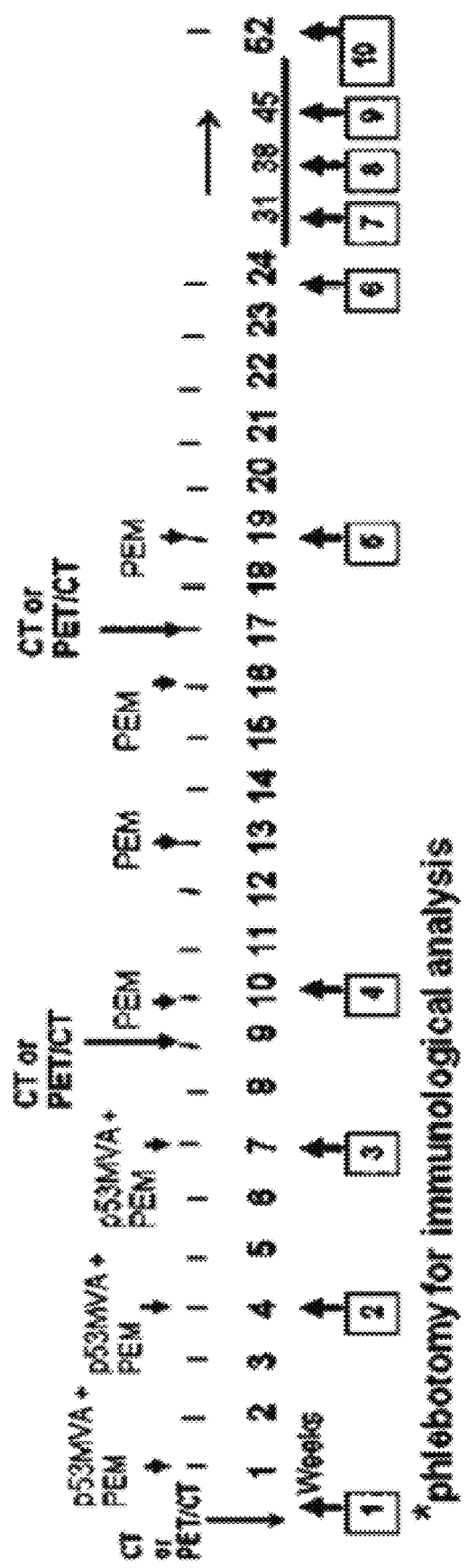
FIG. 3 depicts a schematic representation of the treatment, monitoring, and follow-up schedule.

In some embodiments of the methods of treatment described herein, the p53-targeting vaccine (e.g., p53MVA) and PD-1 pathway inhibitor (e.g., pembrolizumab) will be administered according to the modified schedule shown in FIG. 3, of shorter duration than that employed in single agent studies (e.g., p53MVA only).

In some embodiments of the methods of treatment described herein, the dosage of the p53-targeting vaccine, PD-1 pathway inhibitor, or both remains the same throughout the duration of the treatment. In other embodiments, the dosage of the p53-targeting vaccine, PD-1 pathway inhibitor or both changes (e.g., increase or decrease) during the duration of the treatment.

In some embodiments, if there is any clinical evidence to suggest myopericarditis, patients will receive a full cardiac evaluation, including EKG, serial troponins, echocardiography and consultation by a cardiologist. The p53-targeting vaccine (e.g., p53MVA vaccination) will be withheld in patients showing ≥Grade 2 hepatitis. Non-limiting examples of dosing reductions are listed in Table 1 below.

TABLE 1

Dosing Reductions

| Toxicity | Management |
| --- | --- |
| Grade ≥ 2 hepatitis related or unrelated to p53MVA | Skip and follow the patient weekly or as needed until the toxicity improves to <Grade 2. |
| Grade ≥ 3 allergic reactions possibly related to p53MVA | May resume p53MVA in the next cycle at $2.8 \times 10^8$ pfu |
| Grade 3 non-hematologic toxicity, unrelated to p53MVA | Skip and follow the patient weekly or as needed until the toxicity improves to <Grade 2. Resume p53MVA at $2.8 \times 10^8$ pfu |
| Grade 4 non-hematologic toxicity (even if unrelated to p53MVA) | Off protocol |

In some embodiments of the methods of treatment described herein, the dosage of PD-1 pathway inhibitor (e.g., pembrolizumab) is modified during the duration of treatment. Treatment may be withheld for any of the following reasons: Pneumonitis >Grade 2; Colitis ≥Grade 2; Symptomatic hypophysitis; Grade 2 nephritis; Grade 3 hyperthyroidism; Aspartate aminotransferase (AST) or alanine aminotransferase (ALT) greater than 3 times upper limit of normal (ULN) or total bilirubin greater than 1.5 times ULN. Subjects with elevated bilirubin should be evaluated for biliary obstruction. If biliary obstruction is found to be the cause of the elevated bilirubin and is corrected, treatment may resume at current dose level once bilirubin has improved to ≤1.5. If biliary obstruction is due to disease progression, treatment should be discontinued; Any other severe or Grade 3 treatment-related adverse reaction Dose reductions/delays for anemia are not mandated on this protocol. Supportive care such as red blood cell transfusions and/or growth factors should be implemented according to institutional guidelines. Treatment will resume in patients when AEs recover to Grade 0-1.

In some embodiments of the methods of treatment described herein, the subject has been determined to have a p53 over expressing tumor prior to administration of the p53-targeting vaccine, PD-1 pathway inhibitor, or both. Any known method for testing for p53 over expressing is suitable including, for example, immuno-histochemistry and/or detection of p53 mutation(s) from molecular analysis on DNA obtained from tumor tissue. p53 mutations are distributed in all coding exons of the p53 gene, with a strong predominance in exons 4-9, which encode the DNA-binding domain of the protein. Non-limiting examples of residues that can be mutated include R175, G245, R248, R249, R273, and D281, R282.

In another embodiment of the methods of treatment described herein, upon treatment a p53-targeting vaccine and PD-1 pathway inhibitor combination therapy according to embodiments disclosed, the subject(s) or treatment group(s), including experimental animals such as mice in animal models, exhibit one or more of the following outcomes compared to controls:

an improvement in immune response, as measured by blood draw, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

an improvement in CD4$^+$ and CD8$^+$ T cell responses, as measured by blood draw, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

an improvement in quantification of immunosuppressive cell types (e.g., MDSC, Tregs), as measured by blood draw, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

an improvement in quantification of lymphocyte markers (e.g., PD-1, PDL-1 and PDL-2), as measured by blood draw, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

a reduction in lesions (target and/or non-target lesions, as measured by CT scan or physical exam for apparent lesions, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

a reduction in bone lesions, as measured by bone scan, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

a dissipation (i.e., evaporation) of skin metastases and/or visceral metastases, as measured by biopsy, magnetic resonance imaging, or other suitable methods, of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

a reduction in tumor burden (e.g., number of cancer cells, the size of a tumor, or the amount of cancer in the body) of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control);

an increase in progression-free survival (PFS), of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control); and/or an increase in overall survival (OS), of at least about 99%, at least about 95%, at least about 90%, at least about 80%, at least about 70%, at least about 60%, at least about 50%, at least about 45%, at least about 40%, at least about 35%, at least about 30%, at least about 25%, at least about 20%, at least about 15%, at least about 10%, or at least about 5%, for example, about 30% to about 99%, about 80% to about 90%, about 70% to about 90%, about 60% to about 90%, about 50% to about 90%, about 40% to about 90%, about 35% to about 90%, about 30% to about 90%, about 25% to about 90%, about 5% to about 85%, or about 10% to about 80% (actual % change or median % change compared to baseline or control).

In embodiments, the p53-targeting vaccine and PD-1 are administered sequentially. In embodiments, the p53-targeting vaccine and PD-1 are administered concurrently. In embodiments, the p53-targeting vaccine and PD-1 are admixed together prior to administration.

In embodiments, a response rate to the p53 vaccine (e.g., p53-targeting vaccine) is reduced as compared to baseline reference or control reference. In embodiments, the baseline reference is obtained from the subject prior to administration of the p53-targeting vaccine, PD-1 pathway inhibitor, or both. In embodiments, the baseline reference is obtained from the subject prior to administration of the p53-targeting vaccine. In embodiments, the baseline reference is obtained from the subject prior to administration of the PD-1 pathway inhibitor. In embodiments, the baseline reference is obtained from the subject prior to administration of the p53-targeting vaccine and the PD-1 pathway inhibitor. In embodiments, the control reference is obtained from a healthy subject, a cancer subject, or any population thereof. In embodiments, the control reference is obtained from a healthy subject. In embodiments, the control reference is obtained from a cancer subject. In embodiments, the control reference is obtained from any population of healthy or cancer subjects.

In embodiments, the subject is administered multiple doses of the p53-targeting vaccine, the PD-1 pathway inhibitor, or both. In embodiments, the subject is administered multiple doses of the p53-targeting vaccine. In embodiments, the subject is administered multiple doses of the PD-1 pathway inhibitor. In embodiments, the subject is administered multiple doses of the p53-targeting vaccine and the PD-1 pathway inhibitor.

In embodiments, the subject is administered 2, 3, 4, 5, 6, 7, 8, 9, or 10 doses of the p53-targeting vaccine, the PD-1 pathway inhibitor, or both. In embodiments, the subject is administered 2 doses of the p53-targeting vaccine, the PD-1 pathway inhibitor, or both. In embodiments, the subject is administered 3 doses of the p53-targeting vaccine, the PD-1 pathway inhibitor, or both. In embodiments, the subject is administered 4 doses of the p53-targeting vaccine, the PD-1 pathway inhibitor, or both. In embodiments, the subject is administered 5 doses of the p53-targeting vaccine, the PD-1 pathway inhibitor, or both. In embodiments, the subject is administered 6 doses of the p53-targeting vaccine, the PD-1 pathway inhibitor, or both. In embodiments, the subject is administered 7 doses of the p53-targeting vaccine, the PD-1 pathway inhibitor, or both. In embodiments, the subject is administered 8 doses of the p53-targeting vaccine, the PD-1 pathway inhibitor, or both. In embodiments, the subject is administered 9 doses of the p53-targeting vaccine, the PD-1 pathway inhibitor, or both. In embodiments, the subject is administered 10 doses of the p53-targeting vaccine, the PD-1 pathway inhibitor, or both.

In embodiments, at least one (e.g., 1, 2, 3, 4, 5, 6, 7, 8, 9, 10) dose of the p53-targeting vaccine is administered prior to at least one dose of the PD-1 pathway inhibitor. In embodiments, 2 doses of the p53-targeting vaccine are administered prior to at least one dose of the PD-1 pathway inhibitor. In embodiments, 3 doses of the p53-targeting vaccine are administered prior to at least one dose of the PD-1 pathway inhibitor. In embodiments, 4 doses of the p53-targeting vaccine are administered prior to at least one dose of the PD-1 pathway inhibitor. In embodiments, 5 dose of the p53-targeting vaccine are administered prior to at least one dose of the PD-1 pathway inhibitor. In embodiments, 6 doses of the p53-targeting vaccine are administered prior to at least one dose of the PD-1 pathway inhibitor. In embodiments, 7 doses of the p53-targeting vaccine are administered prior to at least one dose of the PD-1 pathway inhibitor. In embodiments, 8 doses of the p53-targeting vaccine are administered prior to at least one dose of the PD-1 pathway inhibitor. In embodiments, 9 doses of the p53-targeting vaccine are administered prior to at least one dose of the PD-1 pathway inhibitor. In embodiments, 10 doses of the p53-targeting vaccine are administered prior to at least one dose of the PD-1 pathway inhibitor.

In embodiments, at least one dose of the p53-targeting vaccine is administered prior to at least one (e.g., 1, 2, 3, 4, 5, 6, 7, 8, 9, 10) dose of the PD-1 pathway inhibitor. In embodiments, at least one dose of the p53-targeting vaccine is administered prior to 2 doses of the PD-1 pathway inhibitor. In embodiments, at least one dose of the p53-targeting vaccine is administered prior to 3 doses of the PD-1 pathway inhibitor. In embodiments, at least one dose of the p53-targeting vaccine is administered prior to 4 doses of the PD-1 pathway inhibitor. In embodiments, at least one dose of the p53-targeting vaccine is administered prior to 5 doses of the PD-1 pathway inhibitor. In embodiments, at least one dose of the p53-targeting vaccine is administered prior to 6 doses of the PD-1 pathway inhibitor. In embodiments, at least one dose of the p53-targeting vaccine is administered prior to 7 doses of the PD-1 pathway inhibitor. In embodiments, at least one dose of the p53-targeting vaccine is administered prior to 8 doses of the PD-1 pathway inhibitor. In embodiments, at least one dose of the p53-targeting vaccine is administered prior to 9 doses of the PD-1 pathway inhibitor. In embodiments, at least one dose of the p53-targeting vaccine is administered prior to 10 doses of the PD-1 pathway inhibitor.

In embodiments, the subject is administered 3 doses of the p53-targeting vaccine. In embodiments, the subject is administered a maximum of 7 doses of the PD-1 pathway inhibitor. In embodiments, the subject is administered 3 doses of the p53-targeting vaccine and a maximum of 7 doses of the PD-1 pathway inhibitor.

In embodiments, at least one (e.g., 1, 2, 3, 4, 5, 6, 7, 8, 9, 10) dose of PD-1 is administered without a concurrent or substantially concurrent dose of the p53-targeting vaccine. In embodiments, 2 doses of PD-1 are administered without a concurrent or substantially concurrent dose of the p53-targeting vaccine. In embodiments, 3 doses of PD-1 are administered without a concurrent or substantially concurrent dose of the p53-targeting vaccine. In embodiments, 4 doses of PD-1 are administered without a concurrent or substantially concurrent dose of the p53-targeting vaccine. In embodiments, 5 doses of PD-1 are administered without a concurrent or substantially concurrent dose of the p53-targeting vaccine. In embodiments, 6 doses of PD-1 are administered without a concurrent or substantially concurrent dose of the p53-targeting vaccine. In embodiments, 7 doses of PD-1 are administered without a concurrent or substantially concurrent dose of the p53-targeting vaccine. In embodiments, 8 doses of PD-1 are administered without a concurrent or substantially concurrent dose of the p53-targeting vaccine. In embodiments, 9 doses of PD-1 are administered without a concurrent or substantially concurrent dose of the p53-targeting vaccine. In embodiments, 10 doses of PD-1 are administered without a concurrent or substantially concurrent dose of the p53-targeting vaccine.

In one embodiment, the combined effective amount of a p53-targeting vaccine is $5.6 \times 10^8$ pfu and the combined effective amount of a PD-1 pathway inhibitor is 2 mg/kg. In one further embodiment, the subject is administered 3 doses of the p53-targetting vaccine. In one further embodiment, the subject is administered a maximum of 7 doses of the PD-1 pathway inhibitor. In one further embodiment, the subject is administered 1 dose of the p53-targeting vaccine every 3 weeks. In one further embodiment, at least one dose of PD-1 is administered without a concurrent or substantially concurrent dose of the p53-targeting vaccine. In one more further embodiment, at least one dose of the p53-targeting vaccine is administered prior to at least one dose of the PD-1 pathway inhibitor.

In one embodiment, the combined effective amount of a p53-targeting vaccine is $2.8 \times 10^8$ pfu and the combined effective amount of a PD-1 pathway inhibitor is 2 mg/kg. In one further embodiment, the subject is administered 3 doses of the p53-targetting vaccine. In one further embodiment, the subject is administered a maximum of 7 doses of the PD-1 pathway inhibitor. In one further embodiment, the subject is administered 1 dose of the p53-targeting vaccine every 3 weeks. In one further embodiment, at least one dose of PD-1 is administered without a concurrent or substantially concurrent dose of the p53-targeting vaccine. In one more further embodiment, at least one dose of the p53-targeting vaccine is administered prior to at least one dose of the PD-1 pathway inhibitor.

Compositions of p53-Targeting Vaccines and PD-1 Pathway Inhibitors

In some aspects of the methods of treatment described herein, the disclosure provides compositions comprising a p53-targeting vaccine and a PD-1 pathway inhibitor. Also provided are compositions comprising a p53-targeting vaccine and a PD-1 pathway inhibitor and a carrier, optionally a pharmaceutically acceptable excipient. In some embodiments, the compositions further comprise a stabilizer and/or a preservative. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds, chlorbutanol, 2-ethoxyethanol, and imidurea.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like.

To control tonicity, the pharmaceutical composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Parenteral compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate in locating and properly placing the composition to the intended treatment site.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

The composition is preferably sterile. The composition is preferably gluten free. The composition is preferably non-pyrogenic.

The pharmaceutical composition can be administered by any appropriate route, which will be apparent to the skilled person depending on the disease or condition to be treated. In embodiments, the p53 targeting vaccines and PD-1 pathway inhibitors are administered parenterally. Typical routes of administration include intravenous, intra-arterial, intramuscular, subcutaneous, intracranial, intranasal or intraperitoneal.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In some embodiments, the formulation is a controlled release formulation. The term "controlled release formulation" includes sustained release and time-release formulations. Controlled release formulations are well-known in the art. These include excipients that allow for sustained, periodic, pulse, or delayed release of the composition. Controlled release formulations include, without limitation, embedding of the composition (p53-targeting vaccine, PD-1 pathway inhibitor, or both) into a matrix; enteric coatings; micro-encapsulation; gels and hydrogels; implants; and any other formulation that allows for controlled release of a composition.

In one aspect is provided a kit of parts comprising the above-mentioned composition (p53-targeting vaccine, PD-1 pathway inhibitor, or both). The kit may further comprise a document or an instruction that describes a protocol for growing cells in culture for virus production or for administering the composition to a subject in need thereof or for a cancer treatment regimen.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

EMBODIMENTS

Embodiment 1

A method of treating a cutaneous metastasis or a visceral metastasis in a subject in need thereof, the method comprising administering to the subject an effective amount of a p53-targeting modified vaccinia Ankara vaccine and an effective amount of a PD-1 pathway inhibitor to treat the cutaneous metastasis or the visceral metastasis.

Embodiment 2

The method of Embodiment 1, wherein the PD-1 pathway inhibitor comprises pembrolizumab, nivolumab, pidilizumab, avelumab, atezolizumab, durvalumab, BMS-936559, AMP-224, or a combination of two or more thereof.

Embodiment 3

The method of Embodiment 1, wherein the PD-1 pathway inhibitor comprises pembrolizumab.

Embodiment 4

The method of Embodiment 3, wherein the effective amount of the p53-targeting modified vaccinia Ankara vaccine is from about $2.3 \times 10^8$ pfu to about $3.3 \times 10^8$ pfu, and the effective amount of the pembrolizumab is from about 100 mg to about 300 mg.

Embodiment 5

The method of Embodiment 3, wherein the effective amount of the p53-targeting modified vaccinia Ankara vaccine is from about $5.1 \times 10^8$ pfu to about $6.1 \times 10^8$ pfu, and the effective amount of the pembrolizumab is from about 100 mg to about 300 mg.

Embodiment 6

The method of any one of Embodiments 1 to 5, wherein the subject is a breast cancer patient.

Embodiment 7

The method of any one of Embodiments 1 to 5, wherein the subject is a triple negative breast cancer patient.

Embodiment 8

The method of any one of Embodiments 1 to 6, wherein the subject is an estrogen receptor-expressing cancer subject, a human epidermal growth factor receptor 2-expressing cancer subject, or a combination thereof.

Embodiment 9

The method of any one of Embodiments 1 to 8, wherein the subject is an indolent cancer patient.

Embodiment 10

The method of any one of Embodiments 1 to 8, wherein said subject does not have a detectable breast cancer tumor.

Embodiment 11

The method of any one of Embodiments 1 to 10, wherein the subject is a p53-mutant cancer subject.

Embodiment 12

The method of Embodiment 11, wherein the p53-mutant cancer patient does not detectably express a mutated oncogenic protein in addition to a p53 mutant protein.

Embodiment 13

The method of any one of Embodiments 1 to 12, wherein the method comprises treating the cutaneous metastasis.

Embodiment 14

A method for treating a metastatic cancer in a subject in need thereof, the method comprising administering to the subject an effective amount of a p53-targeting vaccine and an effective amount of a PD-1 pathway inhibitor to treat the metastatic cancer.

Embodiment 15

A method for treating cancer in a subject in need thereof, the method comprising administering to the subject an effective amount of a p53-targeting vaccine and an effective amount of a PD-1 pathway inhibitor to treat the cancer.

Embodiment 16

The method of Embodiment 14 or 15, wherein the cancer is squamous cell carcinoma of the head and neck.

Embodiment 17

The method of Embodiment 14 or 15, wherein the cancer is non-small cell lung cancer.

Embodiment 18

The method of Embodiment 14 or 15, wherein the cancer is hepatocellular carcinoma.

Embodiment 19

The method of Embodiment 14 or 15, wherein the cancer is renal cell carcinoma.

Embodiment 20

The method of Embodiment 14 or 15, wherein the cancer is melanoma.

Embodiment 21

The method of Embodiment 14 or 15, wherein the cancer is bladder cancer.

Embodiment 22

The method of Embodiment 14 or 15, wherein the cancer is colon cancer.

Embodiment 23

The method of Embodiment 14 or 15, wherein the cancer is rectal cancer.

Embodiment 24

The method of Embodiment 14 or 15, wherein the cancer is soft tissue sarcoma.

Embodiment 25

The method of Embodiment 14 or 15, wherein the cancer is breast cancer.

Embodiment 26

The method of Embodiment 25, wherein the breast cancer is triple negative breast cancer.

Embodiment 27

The method of Embodiment 25 or 26, wherein the breast cancer is HER2/neu negative breast cancer.

Embodiment 28

The method of any one of Embodiments 25 or 27, wherein the breast cancer is progesterone receptor negative breast cancer.

Embodiment 29

The method of Embodiment 14 or 15, wherein the cancer is colorectal cancer.

Embodiment 30

The method of Embodiment 29, wherein the colorectal cancer displays microsatellite instability.

Embodiment 31

The method of Embodiment 14 or 15, wherein the cancer is pancreatic cancer.

Embodiment 32

The method of Embodiment 14 or 15, wherein the cancer is ovarian cancer.

Embodiment 33

The method of Embodiment 32, wherein the ovarian cancer is platinum-resistant ovarian cancer.

Embodiment 34

The method of Embodiment 14 or 15, wherein the cancer is fallopian tube carcinoma.

Embodiment 35

The method of Embodiment 14 or 15, wherein the cancer is peritoneal carcinoma.

Embodiment 36

The method of Embodiment 14 or 15, wherein the cancer is a solid neoplasm.

Embodiment 37

The method of any one of Embodiments 14 to 36, wherein the effective amount of the p53-targeting vaccine is a low dose amount of the p53-targeting vaccine.

Embodiment 38

The method of Embodiment 37, wherein the low dose amount of the p53-targeting vaccine is a dose reduced by 5%, 10%, 20%, 30%, 40%, 50%, 60%, 70%, 80%, or 90% as compared to a standard dose.

Embodiment 39

The method of any one of Embodiments 14 to 38, wherein the p53-targeting vaccine is a modified vaccinia Ankara.

Embodiment 40

The method of any one of Embodiments 14 to 39, wherein the PD-1 pathway inhibitor binds to a PD-1 receptor.

Embodiment 41

The method of any one of Embodiments 14 to 40, wherein the PD-1 pathway inhibitor is a PD-1 antibody.

Embodiment 42

The method of Embodiment 41, wherein the PD-1 antibody is a monoclonal antibody.

Embodiment 43

The method of Embodiment 41 or 42, wherein the antibody is pembrolizumab, nivolumab, pidilizumab, atezolizumab, durvalumab, a biosimilar thereof, or a combination of two or more thereof.

Embodiment 44

The method of any one of Embodiments 14 to 43, wherein the PD-1 pathway inhibitor potentiates anti-tumor activity of the p53-targeting vaccine.

Embodiment 45

The method of any one of Embodiments 1 to 44, wherein the subject is a mammal.

Embodiment 46

The method of Embodiment 45, wherein the mammal is a human.

Embodiment 47

The method of any one of Embodiments 1 to 46, wherein the p53-targeting vaccine and PD-1 are administered sequentially.

Embodiment 48

The method of any one of Embodiments 1 to 46, wherein the p53-targeting vaccine and PD-1 are administered concurrently.

Embodiment 49

The method of any one of Embodiments 1 to 46, wherein the p53-targeting vaccine and PD-1 are admixed together prior to administration.

Embodiment 50

The method of any one of Embodiments 1 to 49, wherein a response rate to the p53-targeting vaccine is reduced as compared to baseline reference or control reference.

Embodiment 51

The method of Embodiment 50, wherein the baseline reference is obtained from the subject prior to administration of the p53-targeting vaccine, PD-1 pathway inhibitor, or both.

Embodiment 52

The method of Embodiment 50 or 51, wherein the control reference is obtained from a healthy subject, a cancer subject, or any population thereof.

Embodiment 53

The method of any one of Embodiments 14 to 52, wherein the subject has been determined to have a p53 over expressing tumor prior to administration of the p53-targeting vaccine, and the PD-1 pathway inhibitor.

Embodiment 54

The method of any one of Embodiments 1 to 53, wherein the subject is administered multiple doses of the p53-targeting vaccine and the PD-1 pathway inhibitor.

Embodiment 55

The method of Embodiment 54, wherein the subject is administered 2, 3, 4, 5, 6, 7, 8, 9, or 10 doses of the p53-targeting vaccine and the PD-1 pathway inhibitor.

Embodiment 56

The method of any one of Embodiments 1 to 55, wherein at least one dose of the p53-targeting vaccine is administered prior to at least one dose of the PD-1 pathway inhibitor.

Embodiment 57

The method of any one of Embodiments 1 to 56, wherein the subject is administered 3 doses of the p53-targeting vaccine.

Embodiment 58

The method of any one of Embodiments 1 to 57, wherein the subject is administered a maximum of 7 doses of the PD-1 pathway inhibitor.

Embodiment 59

The method of any one of Embodiments 1 to 58, wherein at least one dose of PD-1 is administered without a concurrent or substantially concurrent dose of the p53-targeting vaccine.

Embodiment 60

The method of any one of Embodiments 1 to 59, wherein the effective amount of a p53-targeting vaccine and the effective amount of a PD-1 pathway inhibitor are a combined additive amount.

Embodiment 61

The method of any one of Embodiments 1 to 59, wherein the effective amount of a p53-targeting vaccine and the effective amount of a PD-1 pathway inhibitor are a combined synergistic amount.

Embodiment 62

A method of treating a cutaneous metastasis or a visceral metastasis in a subject in need thereof, the method comprising administering to the subject an effective amount of a p53-targeting vaccine and an effective amount of a PD-1 pathway inhibitor to treat the cutaneous metastasis or the visceral metastasis.

Embodiment 63

The method of Embodiment 62, wherein the combined effective amount is a combined synergistic amount.

Embodiment 64

The method of Embodiment 62 or 63, wherein the subject is a p53-mutant cancer patient.

Embodiment 65

The method of Embodiment 64, wherein the p53-mutant cancer patient does not detectably express a mutated oncogenic protein in addition to a p53 mutant protein.

Embodiment 66

The method of any one of Embodiments 63 to 65, comprising treating the cutaneous metastasis.

Embodiment 67

The method of any one of Embodiments 63 to 66, comprising treating the visceral metastasis.

Embodiment 68

The method of any one of Embodiments 63 to 67, wherein the subject is a triple negative breast cancer patient.

Embodiment 69

The method of any one of Embodiments 63 to 67, wherein said subject is a breast cancer patient.

Embodiment 70

The method of any one of Embodiments 63 to 69, wherein said subject is an indolent cancer patient.

Embodiment 71

The method of any one of Embodiments 63 to 70, wherein said subject does not have a detectable breast cancer tumor.

Embodiment 72

The method of any one of Embodiments 63 to 71, wherein said subject does not have a detectable cancer tumor.

Embodiment 73

The method of any one of Embodiments 62 to 72, wherein the effective amount of the p53-targeting vaccine is a low dose amount of the p53-targeting vaccine.

Embodiment 74

The method of any one of Embodiments 62 to 73, wherein the low dose amount of the p53-targeting vaccine is a dose reduced by 5%, 10%, 20%, 30%, 40%, 50%, 60%, 70%, 80%, or 90% as compared to a standard dose.

Embodiment 75

The method of any one of Embodiments 62 to 74, wherein the p53-targeting vaccine is a modified vaccinia Ankara.

Embodiment 76

The method of any one of Embodiments 62 to 75, wherein the PD-1 pathway inhibitor binds to a PD-1 receptor.

Embodiment 77

The method of any one of Embodiments 62 to 76, wherein the PD-1 pathway inhibitor is a PD-1 antibody.

Embodiment 78

The method of any one of Embodiments 62 to 77, wherein the PD-1 pathway inhibitor is a monoclonal PD-1 antibody.

Embodiment 79

The method of Embodiment 77 or 78, wherein the PD-1 antibody is pembrolizumab, nivolumab, pidilizumab, MPDL3280A, durvalumab, a biosimilar thereof, or a combination of two or more thereof.

Embodiment 80

The method of any one of Embodiments 62 to 79, wherein the PD-1 pathway inhibitor potentiates anti-tumor activity of the p53-targeting vaccine.

Embodiment 81

The method of any one of Embodiments 62 to 80, wherein the subject is a mammal.

Embodiment 82

The method of any one of Embodiments 62 to 81, wherein the subject is a human.

Embodiment 83

The method of any one of Embodiments 62 to 82, wherein the p53-targeting vaccine and PD-1 are administered sequentially.

Embodiment 84

The method of any one of Embodiments 62 to 82, wherein the p53-targeting vaccine and PD-1 are administered concurrently.

Embodiment 85

The method of Embodiment 84, wherein the p53-targeting vaccine and PD-1 are admixed together prior to administration.

Embodiment 86

The method of any one of Embodiments 62 to 85, wherein a response rate to the p53-targeting vaccine is reduced as compared to baseline reference or control reference.

Embodiment 87

The method of Embodiment 86, wherein the baseline reference is obtained from the subject prior to administration of the p53-targeting vaccine, PD-1 pathway inhibitor, or both.

Embodiment 88

The method of Embodiment 86, wherein the control reference is obtained from a healthy subject, a cancer subject, or any population thereof.

Embodiment 89

The method of any one of Embodiments 62 to 88, wherein the subject is administered multiple doses of the p53-targeting vaccine, the PD-1 pathway inhibitor, or both.

Embodiment 90

The method of any one of Embodiments 62 to 89, wherein the subject is administered 2, 3, 4, 5, 6, 7, 8, 9, or 10 doses of the p53-targeting vaccine, the PD-1 pathway inhibitor, or both.

Embodiment 91

The method of any one of Embodiments 62 to 83 or 86 to 90, wherein at least one dose of the p53-targeting vaccine is administered prior to at least one dose of the PD-1 pathway inhibitor.

Embodiment 92

The method of any one of Embodiments 62 to 91, wherein the subject is administered 3 doses of the p53-targeting vaccine.

Embodiment 93

The method of any one of Embodiments 62 to 92, wherein the subject is administered a maximum of 7 doses of the PD-1 pathway inhibitor.

Embodiment 94

The method of any one of Embodiments 62 to 83 or 86 to 93, wherein at least one dose of PD-1 is administered without a concurrent or substantially concurrent dose of the p53-targeting vaccine.

Embodiment 95

The method of any one of Embodiments 1, 2, and 14 to 84, wherein the effective amount of the p53-targeting vaccine is about $2.8 \times 10^8$ pfu.

Embodiment 96

The method of any one of Embodiments 1, 2, and 14 to 84, wherein the effective amount of the p53-targeting vaccine is about $5.6 \times 10^8$ pfu.

Embodiment 97

The method of any one of Embodiments 1, 2, and 14 to 84, wherein the effective amount of the p53-targeting vaccine is from about $1.9 \times 10^8$ pfu to about $6.5 \times 10^8$ pfu.

Embodiment 98

The method of any one of Embodiments 1, 2, and 14 to 84, wherein the effective amount of the p53-targeting vaccine is from about $2.0 \times 10^8$ pfu to about $6.4 \times 10^8$ pfu.

Embodiment 99

The method of any one of Embodiments 1, 2, and 14 to 84, wherein the effective amount of the p53-targeting vaccine is from about $2.1 \times 10^8$ pfu to about $6.3 \times 10^8$ pfu.

Embodiment 100

The method of any one of Embodiments 1, 2, and 14 to 84, wherein the effective amount of the p53-targeting vaccine is from about $2.2 \times 10^8$ pfu to about $6.2 \times 10^8$ pfu.

Embodiment 101

The method of any one of Embodiments 1, 2, and 14 to 84, wherein the effective amount of the p53-targeting vaccine is from about $2.3 \times 10^8$ pfu to about $6.1 \times 10^8$ pfu.

Embodiment 102

The method of any one of Embodiments 1, 2, and 14 to 84, wherein the effective amount of the p53-targeting vaccine is from about $2.4 \times 10^8$ pfu to about $6.0 \times 10^8$ pfu.

Embodiment 103

The method of any one of Embodiments 1, 2, and 14 to 84, wherein the effective amount of the p53-targeting vaccine is from about $2.5 \times 10^8$ pfu to about $5.9 \times 10^8$ pfu.

Embodiment 104

The method of any one of Embodiments 1, 2, and 14 to 84, wherein the effective amount of the p53-targeting vaccine is from about $2.6 \times 10^8$ pfu to about $5.8 \times 10^8$ pfu.

Embodiment 105

The method of any one of Embodiments 1, 2, and 14 to 84, wherein the effective amount of the p53-targeting vaccine is from about $2.7 \times 10^8$ pfu to about $5.7 \times 10^8$ pfu.

Embodiment 106

The method of any one of Embodiments 1, 2, and 14 to 84, wherein the effective amount of the p53-targeting vaccine is from about $2.8 \times 10^8$ pfu to about $5.6 \times 10^8$ pfu.

Embodiment 107

The method of any one of Embodiments 1, 2, and 14 to 84, wherein the effective amount of the p53-targeting vaccine is from about $4.7 \times 10^8$ pfu to about $6.5 \times 10^8$ pfu.

Embodiment 108

The method of any one of Embodiments 1, 2, and 14 to 84, wherein the effective amount of the p53-targeting vaccine is from about $4.8 \times 10^8$ pfu to about $6.4 \times 10^8$ pfu.

Embodiment 109

The method of any one of Embodiments 1, 2, and 14 to 84, wherein the effective amount of the p53-targeting vaccine is from about $4.9 \times 10^8$ pfu to about $6.3 \times 10^8$ pfu.

Embodiment 110

The method of any one of Embodiments 1, 2, and 14 to 84, wherein the effective amount of the p53-targeting vaccine is from about $5.0 \times 10^8$ pfu to about $6.2 \times 10^8$ pfu.

Embodiment 111

The method of any one of Embodiments 1, 2, and 14 to 84, wherein the effective amount of the p53-targeting vaccine is from about $5.1 \times 10^8$ pfu to about $6.1 \times 10^8$ pfu.

Embodiment 112

The method of any one of Embodiments 1, 2, and 14 to 84, wherein the effective amount of the p53-targeting vaccine is from about $5.2 \times 10^8$ pfu to about $6.0 \times 10^8$ pfu.

Embodiment 113

The method of any one of Embodiments 1, 2, and 14 to 84, wherein the effective amount of the p53-targeting vaccine is from about $5.3 \times 10^8$ pfu to about $5.9 \times 10^8$ pfu.

Embodiment 114

The method of any one of Embodiments 1, 2, and 14 to 84, wherein the effective amount of the p53-targeting vaccine is from about $5.4 \times 10^8$ pfu to about $5.8 \times 10^8$ pfu.

Embodiment 115

The method of any one of Embodiments 1, 2, and 14 to 84, wherein the effective amount of the p53-targeting vaccine is from about $5.5 \times 10^8$ pfu to about $5.7 \times 10^8$ pfu.

Embodiment 116

The method of any one of Embodiments 1, 2, and 14 to 84, wherein the effective amount of the p53-targeting vaccine is from about $1.8 \times 10^8$ pfu to about $3.8 \times 10^8$ pfu.

Embodiment 117

The method of any one of Embodiments 1, 2, and 14 to 84, wherein the effective amount of the p53-targeting vaccine is from about $1.9 \times 10^8$ pfu to about $3.7 \times 10^8$ pfu.

Embodiment 118

The method of any one of Embodiments 1, 2, and 14 to 84, wherein the effective amount of the p53-targeting vaccine is from about $2.0 \times 10^8$ pfu to about $3.6 \times 10^8$ pfu.

Embodiment 119

The method of any one of Embodiments 1, 2, and 14 to 84, wherein the effective amount of the p53-targeting vaccine is from about $2.1 \times 10^8$ pfu to about $3.5 \times 10^8$ pfu.

Embodiment 120

The method of any one of Embodiments 1, 2, and 14 to 84, wherein the effective amount of the p53-targeting vaccine is from about $2.2 \times 10^8$ pfu to about $3.4 \times 10^8$ pfu.

Embodiment 121

The method of any one of Embodiments 1, 2, and 14 to 84, wherein the effective amount of the p53-targeting vaccine is from about $2.3 \times 10^8$ pfu to about $3.3 \times 10^8$ pfu.

Embodiment 122

The method of any one of Embodiments 1, 2, and 14 to 84, wherein the effective amount of the p53-targeting vaccine is from about $2.4 \times 10^8$ pfu to about $3.2 \times 10^8$ pfu.

Embodiment 123

The method of any one of Embodiments 1, 2, and 14 to 84, wherein the effective amount of the p53-targeting vaccine is from about $2.5 \times 10^8$ pfu to about $3.1 \times 10^8$ pfu.

Embodiment 124

The method of any one of Embodiments 1, 2, and 14 to 84, wherein the effective amount of the p53-targeting vaccine is from about $2.6 \times 10^8$ pfu to about $3.0 \times 10^8$ pfu.

Embodiment 125

The method of any one of Embodiments 1 to 84, wherein the effective amount of the p53-targeting vaccine is from about $2.7 \times 10^8$ pfu to about $2.9 \times 10^8$ pfu.

Embodiment 126

The method of any one of Embodiments 1 to 25, wherein the effective amount of the p53-targeting vaccine is administered about once per week to about once every four weeks.

Embodiment 127

The method of any one of Embodiments 1 to 125, wherein the effective amount of the p53-targeting vaccine is administered about once every three weeks.

Embodiment 128

The method of any one of Embodiments 1 to 127, wherein the p53-targeting vaccine is administered by subcutaneous injection.

Embodiment 129

The method of any one of Embodiments 1, 2, and 14 to 128, wherein the PD-1 pathway inhibitor is pembrolizumab.

Embodiment 130

The method of Embodiment 129, wherein the effective amount of pembrolizumab is from about 100 mg to about 300 mg.

Embodiment 131

The method of Embodiment 129, wherein the effective amount of pembrolizumab is from about 150 mg to about 250 mg.

Embodiment 132

The method of Embodiment 129, wherein the effective amount of pembrolizumab is about 200 mg.

Embodiment 133

The method of any one of Embodiments 129 to 132, wherein the effective amount of pembrolizumab is administered about once per week to about once every four weeks.

Embodiment 134

The method of any one of Embodiments 129 to 132, wherein the effective amount of pembrolizumab is administered about once every three weeks.

Embodiment 135

The method of any one of Embodiments 1, 2, and 14 to 118, wherein the PD-1 pathway inhibitor is atezolizumab.

Embodiment 136

The method of Embodiment 135, wherein the effective amount of atezolizumab is from about 500 mg to about 2000 mg.

Embodiment 137

The method of Embodiment 135, wherein the effective amount of atezolizumab is about 1200 mg.

Embodiment 138

The method of any one of Embodiments 135 to 137, wherein the effective amount of atezolizumab is administered about once per week to about once every four weeks.

Embodiment 139

The method of any one of Embodiments 135 to 137, wherein the effective amount of atezolizumab is administered about once every three weeks.

Embodiment 140

The method of any one of Embodiments 1, 2, and 14 to 128, wherein the PD-1 pathway inhibitor is nivolumab.

Embodiment 141

The method of Embodiment 140, wherein the effective amount of nivolumab is from about 200 mg to about 280 mg.

Embodiment 142

The method of Embodiment 140, wherein the effective amount of nivolumab is about 240 mg.

Embodiment 143

The method of any one of Embodiments 140 to 142, wherein the effective amount of nivolumab is administered from about once per week to about once every four weeks.

Embodiment 144

The method of any one of Embodiments 140 to 142, wherein the effective amount of nivolumab is administered about once every two weeks.

Embodiment 145

The method of any one of Embodiments 1, 2, and 14 to 128, wherein the PD-1 pathway inhibitor is pidilizumab.

Embodiment 146

The method of Embodiment 145, wherein the effective amount of pidilizumab is from about 100 mg to about 300 mg.

Embodiment 147

The method of Embodiment 145, wherein the effective amount of pidilizumab is about 200 mg.

Embodiment 148

The method of any one of Embodiments 145 to 147, wherein the effective amount of pidilizumab is administered from about once every twenty-eight days to about once every sixty days.

Embodiment 149

The method of any one of Embodiments 1, 2, and 14 to 128, wherein the PD-1 pathway inhibitor is durvalumab.

Embodiment 150

The method of Embodiment 149, wherein the effective amount of durvalumab is from about 5 mg/kg to about 15 mg/kg.

Embodiment 151

The method of Embodiment 149, wherein the effective amount of durvalumab is about 10 mg/kg.

Embodiment 152

The method of any one of Embodiments 149 to 151, wherein the effective amount of durvalumab is administered from about once per week to about once every four weeks.

Embodiment 153

The method of any one of Embodiments 149 to 151, wherein the effective amount of durvalumab is administered about once every two weeks.

Embodiment 154

The method of any one of Embodiments 1, 2, and 14 to 128, wherein the PD-1 pathway inhibitor is avelumab.

Embodiment 155

The method of Embodiment 154, wherein the effective amount of avelumab is from about 5 mg/kg to about 15 mg/kg.

Embodiment 156

The method of Embodiment 154, wherein the effective amount of avelumab is about 10 mg/kg.

Embodiment 157

The method of any one of Embodiments 154 to 156, wherein the effective amount of avelumab is administered about once per week to about once every four weeks.

Embodiment 158

The method of any one of Embodiments 154 to 156, wherein the effective amount of avelumab is administered about once every two weeks.

Embodiment 159

The method of any one of Embodiments 1 to 158, wherein the PD-1 pathway inhibitor is administered by intravenously.

Embodiment 160

The method of any one of Embodiments 1 to 158, wherein the PD-1 pathway inhibitor is administered by intravenous infusion.

EXAMPLES

The following examples are intended to further illustrate certain embodiments of the disclosure. The examples are put forth so as to provide one of ordinary skill in the art and are not intended to limit its scope.

Example 1

Treatment of Metastatic Mouse Model with Pembrolizumab

Pre-clinical data with a murine equivalent of pembrolizumab has shown dramatic success in a metastatic model of pancreatic cancer that is resistant to the chemotherapy agent GEMZAR® and ABRAXANE® combinations. The preliminary experiments show that anti-murine PD-1 monoclonal antibody (kindly provided by Dr. Bruce Blazar, University of Minnesota Cancer Center) induces tumor regression in an immunocompetent syngeneic orthotopic (o.t.) murine KPC (Kras and p53 mutant) PDAC (PD-L1+) cell model. Mice with 13 day established tumors received treatment on days 13 and 20 and showed dramatic regressions of both small and large tumors (data not shown). These tumors express PD-L1. Therefore, it is contemplated that the remissions likely involve, at least in part, the PD-1/PDL-1 inhibitor pathway.

Figure 2A:
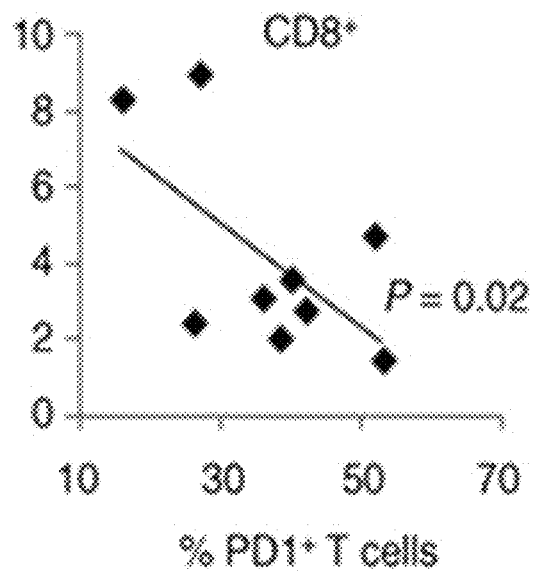

High frequencies of PD-1+ T cells were detected in the patients receiving p53MVA alone as compared to healthy donors FIG. 1. Since in vitro studies with human PBMC have shown that PD-1 ligation dramatically shifts the dose-response curve, making T cells less sensitive to T-cell receptor-generated signals it was of concern. It was determined that even low levels of PD-1 expression can inhibit functions such as cytokine release and T cell expansion. Further investigation showed that antibody blockade of PD-1 in vitro increased the p53 immune responses detected after the second or third immunizations. FIG. 2B.

These data suggested that treatment with checkpoint inhibitor (i.e., PD-1 monoclonal antibodies) in combination with p53MVA will confer durable anti-tumor immunity and extend remission.

Example 2

Combination Therapy of p53MVA Vaccine with Pembrolizumab.

Despite the detection of immunological responses to the p53MVA vaccine, clinical responses were not apparent when the vaccine was used as a monotherapy. A Phase I, single center study was conducted to determine the safety and tolerability of combined p53MVA vaccine and pembrolizumab that are well-tolerated in patients with refractory, p53 over expressing cancer. Additionally, clinical response and anti-p53 T cell immune responses were evaluated. Approximately, 9 to 19 patients will be enrolled. The study will utilize a modified 3+3 design, although this is not a true MTD seeking trial since the upper limit of the p53MVA single agent dosing and the upper limit of pembrolizumab are already established. Since the toxicities of each agent are not overlapping, 3 patients will be initially enrolled at a single dose level and dose de-escalation of p53MVA will be employed if necessary.

The primary endpoint will be toxicity, classified using the NCI Common Toxicity Criteria for adverse events (CTCAE) v4.3. This allows determination of the tolerability of p53MVA and pembrolizumab in combination. Secondary endpoints will be clinical response and T cell reactivity to p53.

Inclusion Criteria: The trial will be open to patients with advanced, refractory cancer, including, non-small cell lung cancer, squamous cell carcinoma of the head and neck, hepatocellular carcinoma, renal cell carcinoma, melanoma, bladder, soft tissue sarcoma, triple-negative breast cancer, and colorectal carcinoma displaying microsatellite instability and pancreatic cancer overexpressing p53 who have failed, intolerant of, or refuse standard treatment and have an Eastern Cooperative Oncology Group (ECOG) status of ≤2 (Karnofsky ≥60%) and no brain metastases. Patients must be at least 18 years of age and able to give informed consent. There must be evidence of p53 over-expression by immunohistochemistry and/or detection of p53 mutation from molecular analysis on DNA obtained from tumor tissue. In addition, patients must have at least one of an absolute neutrophil count: ≥1,500/l; platelets ≥100,000/l; a hemoglobin level must be greater than 9 g/dL; renal function: calculated or measured creatinine clearance ≥50 ml/min and/or serum creatinine ≤1.6 mg/dl; and hepatic function: total bilirubin ≤1.5× institutional upper limit of normal, AST and ALT ≤3 times institutional upper normal level (AST and ALT ≤5 times institutional upper normal level, if there is evidence of liver metastasis). In addition p53 over expression will be determined by immunohistochemistry (e.g., ≥10% of cells within the tumor staining positive) or those with a p53 mutation as determined by mutational analysis of tumor tissue will be eligible. Patients with prior exposure to p53-based vaccines will be eligible.

Exclusion Criteria: The trial will not be open to patients with immunodeficiency (HIV, organ grafts), autoimmune disease, concurrent use of systemic corticosteroids. Patients with a history of severe neurological, cardiovascular, renal, endocrine, respiratory or bone marrow dysfunction, congestive heart failure, coronary artery disease or myopericarditis will not be eligible. Pregnancy or lactation, allergy to egg proteins and radiation within the 4 weeks preceding enrollment will also exclude participation.

A subcutaneous dose of $5.6 \times 10^8$ pfu was well-tolerated in the previous Phase I single agent trial of p53MVA, therefore this study will employ an equivalent dose. Hardwick N R, Clin Cancer Res, 2014, 10(17)4459-70. An FDA approved, standard dose of pembrolizumab of 2 mg/kg will be employed. Dose modification of p53MVA will be employed in the case of dose limiting toxicity (DLT). Any of the following will be considered a DLT: any life-threatening adverse reaction; any grade 2 or higher myocarditis and pneumonitis; grade 3 or 4 infusion-related reactions despite medications; other toxicities Grade ≥3 (Note: transient Grade 3-4 laboratory abnormalities that are not clinically significant and resolve within 72 hours, will not be considered DLTs); and a dosing delay due to toxicity for >21 consecutive days.

Treatment Schedule: p53MVA and pembrolizumab will be given concurrently according to the schedule in Table 2 and Table 3. The aim is to use pembrolizumab to enhance the activity of the p53MVA vaccine to deliver clinical benefit. Patients will receive injections of p53MVA vaccine, for a total of three injections. Patients will be evaluated for DLT through the first cycle of therapy. Pembrolizumab will be administered at a standard dose of 2 mg/kg every 3-4 weeks, for a maximum of 7 doses.

TABLE 2

Dosing Schedule

| Time | Treatment |
|---|---|
| Week 1 (day 1): | p53MVA + pembrolizumab |
| Week 4: | p53MVA + pembrolizumab |
| Week 7: | p53MVA + pembrolizumab |
| Week 10: | pembrolizumab |
| Week 13: | pembrolizumab |
| Week 16: | pembrolizumab |
| Week 20: | pembrolizumab |

TABLE 3

Regimen Description
Regimen Description (dose level 1)

| Agent | Precautions | Dose* | Route | Schedule | Cycle Length |
|---|---|---|---|---|---|
| p53MVA | Monitor for severe adverse events prior to each vaccination | $5.6 \times 10^8$ pfu In a volume of 1.0 ml | Single injection into subcutaneous tissue of the upper arm (over deltoid muscle) | Every 3 weeks for a total of 3 vaccinations | 3 weeks |
| Pembrolizumab (PEM) | Monitor for severe adverse events prior to each infusion | 2 mg/kg | i.v. infusion in 0.9% sodium chloride injection, USP, over 30 minutes | on weeks 1, 4, 7, 10, 13, 16 and 19 for a maximum of 7 doses | |

In the case of grade 3 vaccine related toxicity, the dose of p53MVA will be decreased. In the case of pembrolizumab induced immune-mediated reactions, treatment will be held or permanently discontinued according to the package insert. This study will be conducted in compliance with the protocol, Good Clinical Practice (GCP) and the applicable regulatory requirements.

A physical exam will be performed pre-study and prior to treatment at weeks 1, 4, 7, 10, 13, 16, 19 and post study (week 52) if appropriate. A CT scan (or physical exam for apparent lesions) will be performed pre study, and every two months according to standard of care.

All subjects will be monitored for one hour in the clinic after each immunization. Subject's temperature and any local reaction at the injection site will be noted. The subjects will be contacted after each immunization to evaluate vaccine related complications. If there is any clinical evidence to suggest myopericarditis, patients will receive a full cardiac evaluation, including EKG, serial troponins, echocardiography and consultation by a cardiologist.

Phlebotomy will be performed for comprehensive metabolic panel (CMP), complete blood count with differential (CBC/DBC) and immunological assays. Blood draws for immunological monitoring together with a differential blood count may continue up to 12 months if the PI deems necessary and the patient is able to provide a specimen. Patients with an Hgb level of less than 9 g/dL will not undergo further immunologic blood draws until the Hgb level has been documented to rise above 9 g/dL. Immunological monitoring will include determination of $CD4^+$ and $CD8^+$ T cell responses to a p53 peptide library and quantification of immunosuppressive cell types (MDSC, Tregs) and selected lymphocyte markers such as PD-1, PDL-1 and PDL-2.

$CD8^+$ T cell signals will be evaluated for levels that exceed those as compared to the single agent p53MVA delivery. During delivery of p53MVA alone, p53-reactive $CD8^+$ T cells increased above baseline after the first immunization, but did not expand further with subsequent immunization. It is contemplated that the $CD8^+$ T cell response will be enhanced by pembrolizumab, resulting in larger or more durable increases in the $CD8^+$ T cell response. The total area under the curve (AUC) of the $CD8^+$ T cell reactivity over three injections (minus the baseline) provides a metric for this requirement. There is at least 84% power to detect a 2.1-fold increase in AUC with a type I error of 22%. Empirically, this is associated with a cut-off of a 55% increase in AUC. These estimates use the Wilcoxon rank-sum test, and are based on residual re-sampling simulations based on historical AUC values (subtracting baseline) and a hypothesized increase in that AUC.

TABLE 4

Dosing/Administration may be de-escalated if needed.
Dose De-Escalation Table (if needed)

| Dose Level/Arm | 1. Dose | |
|---|---|---|
| | p53MVA | pembrolizumab |
| Level 1 | $5.6 \times 10^8$ pfu every 3 wks | 2 mg/kg every three weeks |
| Level-1 | $2.8 \times 10^8$ pfu every 3 wks | 2 mg/kg every three weeks |

Patients completing combination therapy (p53MVA+ PEM on weeks 1, 4 and 7) may be treated with up to 4 more doses of pembrolizumab (PEM) on weeks 10, 13, 16 and 19.

Example 3

62-year-old gentleman with P 16 positive squamous cell carcinoma of the oropharynx metastatic to the liver. He was initially diagnosed in July 2013. He received cisplatin in combination with radiation therapy completed September 2013. In June 2014 he developed metastatic disease to the liver. He was treated on clinical trial with ARQ 197+ cetuximab. He had progressive disease after 2 cycles. He was switched to carboplatin and cetuximab chemotherapy but had toxicities and was intermittently treated with 5-FU. He then enrolled in IRB #15002 with MVAp53 and pembrolizumab. His tumor had 10-15% staining for p53. He initiated treatment on Feb. 16, 2017 with cycle 1 day 1. He tolerated the therapy well without any significant toxicity. His first CT scan showed a 25% increase from baseline. He remained on the clinical trial since he was clinically doing well. Follow-up CT scan on Jun. 8, 2017 showed that his disease was stable. He continued on protocol and completed the 7 cycles of chemotherapy. He currently remains on pembrolizumab alone.

Example 4

42-year-old female with triple negative breast cancer metastatic to the chest wall, mediastinal lymph nodes, left axillary lymph nodes and liver metastasis. Her tumor profile shows tumor infiltrating lymphocytes at 60%, PD-L1 at 30% and a TP53 mutation on foundation one analysis. She was initially diagnosed in 2012 and underwent neoadjuvant ACT chemotherapy. She underwent surgical resection but developed metastatic disease. She was treated systemically with Ixempra and Xeloda followed by Gemzar and then most recently carboplatin and Taxol prior to enrolling in the clinical trial. On Aug. 13, 2017 she received cycle 1 day 1 of the combination of MVA p53 and pembrolizumab. Her first CT scan on Oct. 10, 2017 showed stable disease by RECIST criteria. She remains on protocol with cycle 5 day 1 being given on Nov. 14, 2017.

Example 5

Treatment of Patient with Cutaneous Metastasis with p53MVA Vaccine with Pembrolizumab.

Figure 4A:
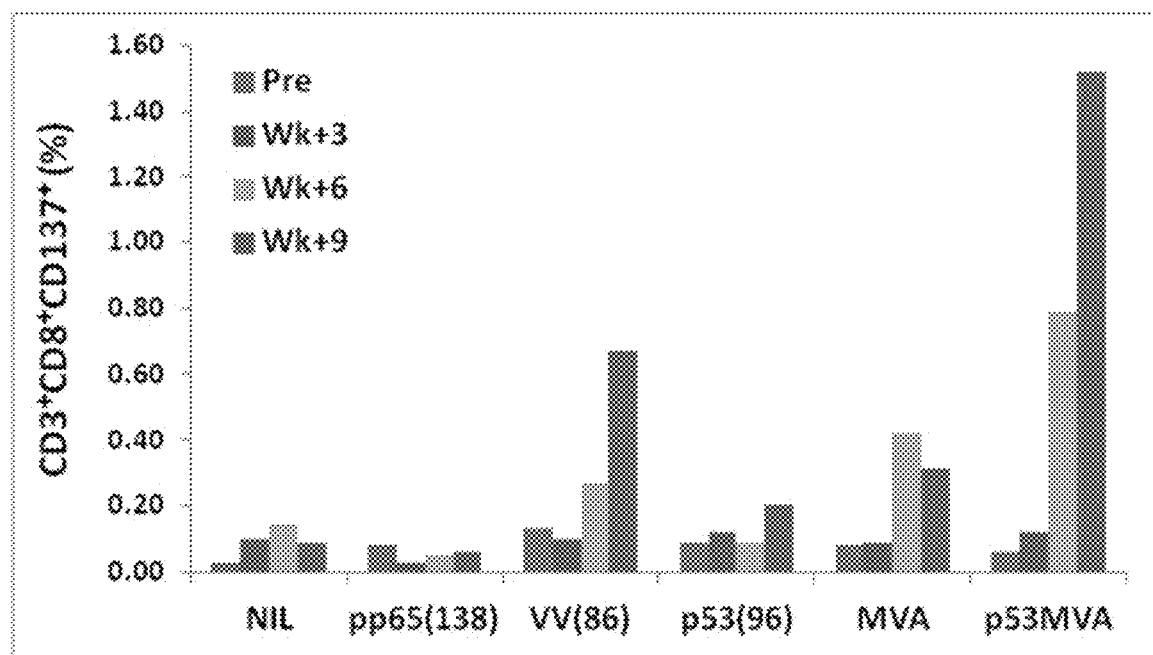
Figure 4B:
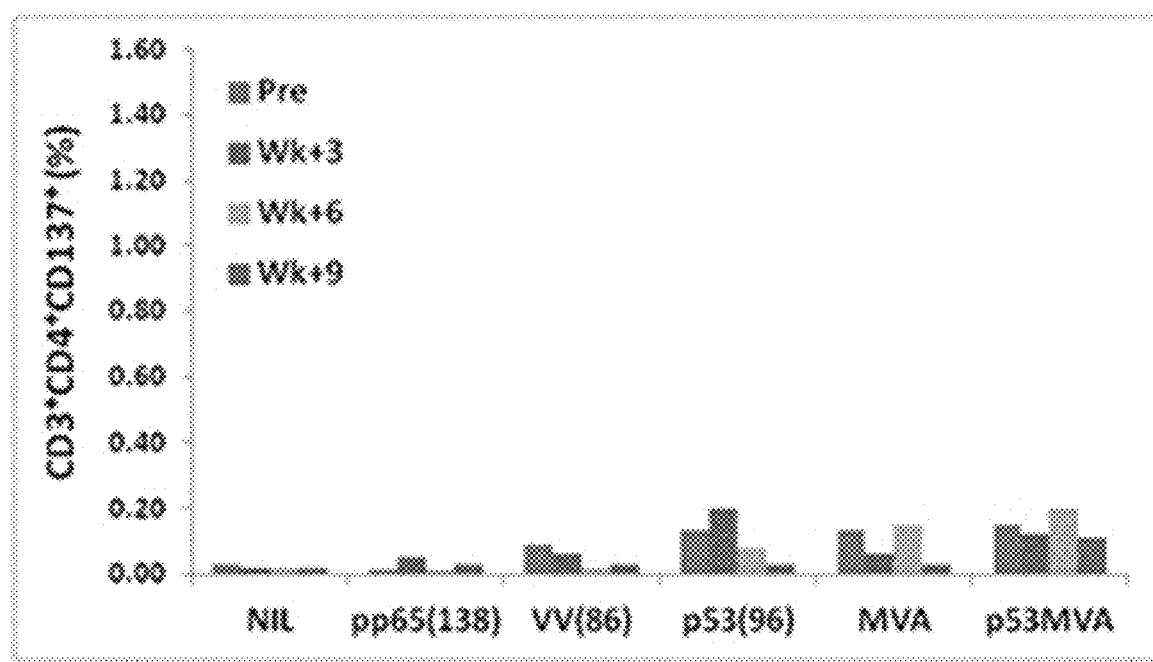
Figure 5:
FIG. 5 shows clinical observations of a patient over duration of combination p53MVA and pembrolizumab treatment.
Figure 6A:
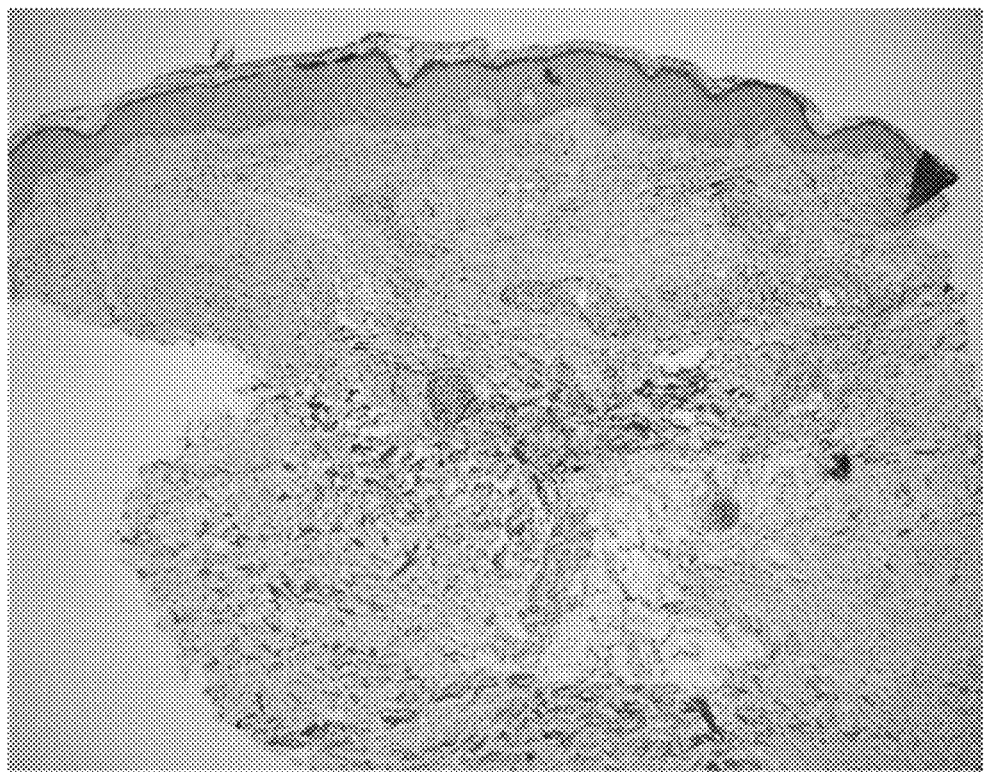
FIGS. 6A-6D are representative images of pathology of biopsy showing carcinoma present, mostly within the lymphatics at baseline (FIG. 6A) and baseline at high magnification (FIG. 6B) and post treatment showing mild superficial perivascular lymphocytic infiltrate and negative for metastatic breast cancer (FIG. 6C) and post treatment at high magnification showing no tumor cells present (FIG. 6D).
Figure 6B:
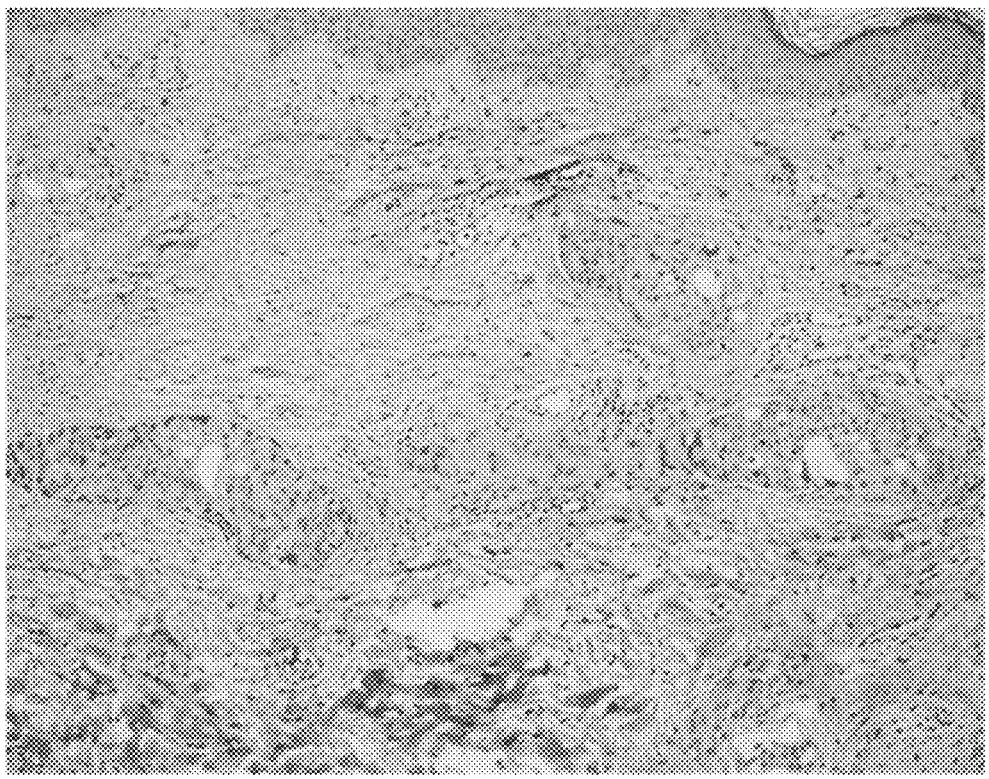
Figure 6C:
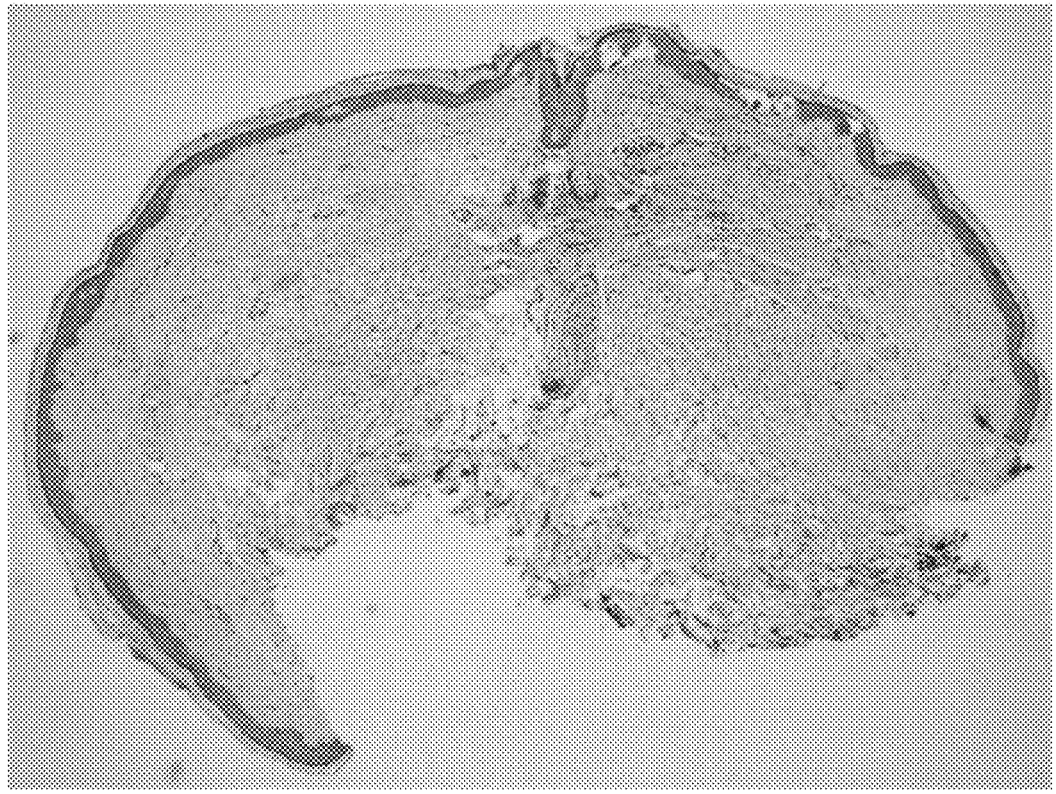
Figure 6D:
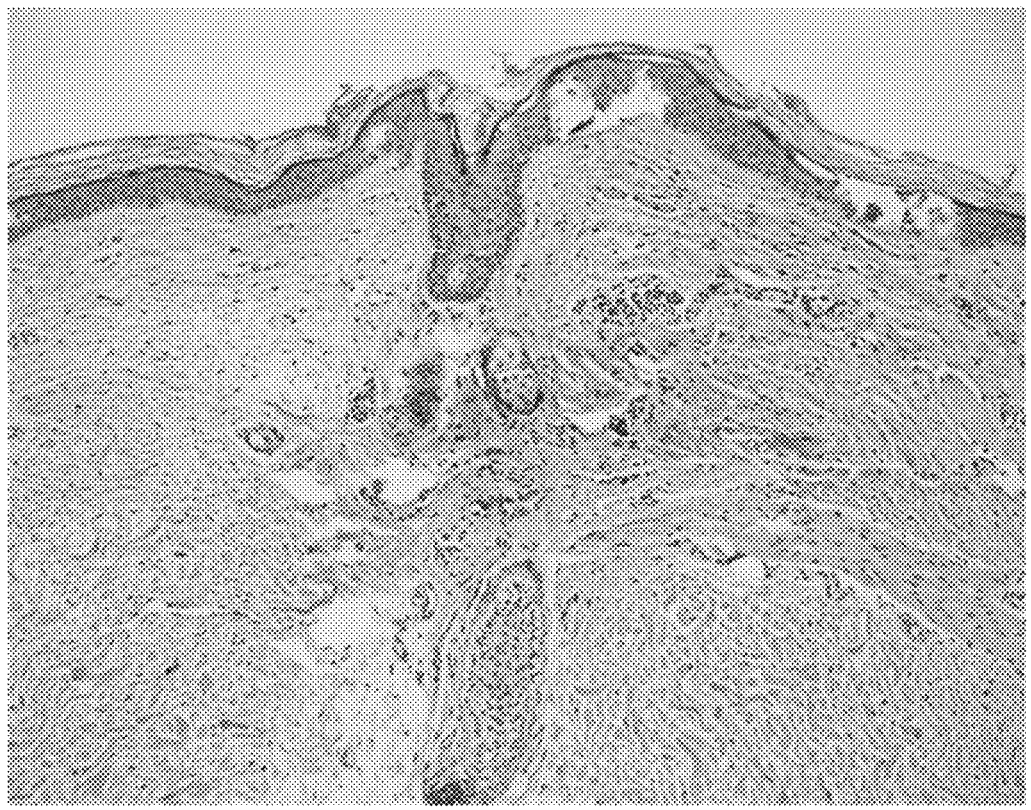

A 69-year old female patient diagnosed with triple negative breast cancer overexpressing mutant p53 (D281E) and non-responsive to conventional treatment regimens that included capeitabine, paclitaxel, eribulin, ixabepilone, doxil, and gemcitabine received the combination p53MVA-pembrolizumab combination therapy as outlined above. As shown in FIG. 5, Visible clearing of skin, including reducing of lesions, inflammation and discoloration were observed within six weeks following start of treatment and continued through Week +9. In particular, skin metastases dissipated (i.e., evaporated). At baseline, pathology showed carcinoma present, mostly within lymphatics. Surprisingly, at six weeks post-vaccination patient exhibited a partial response (PR) of cutaneous metastasis and biopsy at four different locations all showed no tumor cells based on pathology report with mild superficial perivascular lymphocytic infiltrate. FIG. 6. In addition, T cells from PBMCs collected from the patient showed an increased specificity in response in 24 hour stimulation culture with p53MVA, MVA, $p53_{96}$, $VV_{86}$, and $pp65_{138}$. FIG. 4A-C.

Example 6

Continued treatment of patient with cutaneous metastasis with P53mva vaccine with pembrolizumab. Applicants developed a vaccine construct targeting wild type human p53 antigen using the delivery vector modified Ankara or MVA. After having limited clinical success as a single agent, Applicants initiated two clinical trials combining either gemcitabine (NCT02275039) or the monoclonal antibody (mAb) referred to as KEYTRUDA® or pembrolizumab (NCT02432963) with the p53MVA vaccine. While the combination p53MVA and pembrolizumab (PEM) treatment was unsuccessful in halting disease progression in two pancreatic adenocarcincoma patients, Applicants enrolled a late-stage triple negative breast cancer patient who showed remarkable clearance of all tumor cells in the patient's skin after only nine weeks of therapy. Patient had 60-70% of skin covered by inflamed lesions, primarily on thigh and back. The patient received three doses of vaccine and a corresponding three doses of KEYTRUDA®. The patient has continued to show improvement in the skin lesions, and most remarkably in index visceral ling, bone, and invasive soft tissue metastases by CT scan. The patient has reduced pain, better performance status, and increased mobility. Pathological analyses of select skin biopsies revealed the absence of any evidence of breast carcinoma tumor cells. The patient was declared cancer-free in the skin samples that were analyzed. Investigations of the patient's peripheral blood mononuclear cells showed a prominent and increasing p53-specific immune response, as well as poxvirus immunity, mainly in the CD 8 T cell subset. The patient continues to improve at the four month time point after initiation of therapy. For comparison, the Keynote-012 trials (NCT02447003) demonstrated an overall 18.5% response rate, with one complete remission (CR 3.5%), and a median time of response of 17.9 weeks, although median PFS had not yet been defined.

Example 7

Applicants will initiate Phase II/III clinical trials including randomized and single arm studies as follows.

Triple negative breast cancer (TNBC): TNBC is an excellent candidate indication for the randomized Phase II/III clinical trial as pembrolizumab (PEM) is not approved, and yet its response rate (RR) is 18.5%. Furthermore, the potential for receiving p53MVA in addition to PEM makes this a compelling study for patients to enroll.

The Phase II portion of the Phase II/III study will require at least 99 patients. This sample size will provide adequate power (83%) to detect an improvement in the response rate from 20% to 40% with a type I error of 0.2. The study will use 2:1 randomization, with 33 v 66 patients. The primary endpoint of this study is an assessment of the effectiveness of the combination therapy, while the secondary endpoint of the study is to evaluate immune correlatives.

Ovarian Cancer: Single arm studies with convincing clinical benefit can lead to off-label use once the drug is approved, and ovarian cancer is a population where a randomized study against pembrolizumab alone would not be possible. This is because the reported response rate of pembrolizumab of around 10% would discourage patients from enrolling in a study that could randomize patients to pembrolizumab alone. The alternative is a single arm study using the p53MVA+Pembro combination. This single arm study will require approximately 28-34 patients and should complete accrual within 2 years. The study should be available for a full report in approximately 3 years after study initiation.

The reported response to pembrolizumab is 11%, and response to nivolumab is 23% in ovarian cancer. 90% power will be required to distinguish between a promising response rate of 31% vs 11% with 10% type I error.

Stage 1: 16 points. Stage 2: if two or more responders, add 12 points. Total: 28 points: minimum of 6 responders.

The study will also evaluate immune correlatives.

Sarcoma: Another population where a randomized study would not be expected is in sarcoma, an orphan disease of mixed histologies, where single arm studies are often employed due to the flexibility afforded by orphan diseases, the limited patient numbers, and competing large randomized studies through SARC and other cooperative groups. The FDA also has a special office (FDA Office of Orphan Products Development) and this study has the potential to be the first indication if there are sufficient numbers of responders. This study is targeted to complete within 3 years after study initiation.

The reported response to pembrolizumab in soft-tissue sarcoma is 19%. 90% power is required to distinguish between a promising response rate of 39% vs 19% with 10% type I error.

Stage 1: 19 pts. Stage 2: if 3 or more responders, add 15 pts. Total: 34 pts: minimum of 10 responders required.

The study will also evaluate immune correlatives.

These three clinical trials result in 161 patients, and accounting for a 5% drop-out rate, Applicants anticipate 169 patients.

Example 8

Example 8 relates to and provides further details on Example 5 and Example 6.

A heavily pretreated patient with triple negative breast cancer distinguished by cutaneous metastases received p53MVA vaccine in combination with pembrolizumab. Her cutaneous metastases regressed and after two cycles of therapy, a skin biopsy showed a complete pathological response. Systemic response was confirmed with restaging CT and bone scans. Activation of p53-specific T cell responses and elevation of multiple immune response genes in peripheral blood correlated with the rapid clinical response which lasted for 6 months after the initiation of combined therapy.

Triple negative breast cancer (TNBC) represents approximately 15% of all breast cancers, and is associated with poor outcomes with a median survival of only 13.3 months in the metastatic setting. (1). Due to the lack of expression of estrogen (ER), progesterone (PR), and epidermal growth factor receptor-2/neu (HER-2/neu) receptors that are targets for most breast cancer therapies, cytotoxic chemotherapy associated with significant systemic toxicity remains the only treatment option. (2,3). Hence, effective and less toxic targeted therapy is urgently needed to improve outcomes in TNBC.

A majority of solid tumors, including TNBC, carry p53 gene mutations resulting in the accumulation of p53 protein within tumor cells. (4). Most mutations of p53 involve the alteration of a single amino acid, thus, the majority of p53 epitopes processed and presented for T cell recognition on tumor cells are wild-type in sequence. Of notable interest, wild-type p53 is not presented on the surface of normal parenchymal cells in healthy adults making the protein cryptic for the immune system. (5). However, humans retain the potential of developing anti-p53 immune responses when p53 becomes available for presentation as an antigen. To take advantage of this scenario, Applicants have developed a genetically engineered Modified Vaccinia Ankara (MVA) viral vector to express wild-type human p53 transgene (p53MVA). (6,7) Using p53MVA to deliver full-length p53 has the potential to generate sustained antigen expression and the presentation of numerous antigenic epitopes in the context of various HLA molecules. (6-8). In the first-in-human phase I trial, p53MVA vaccination was well tolerated and increased the frequency of p53-reactive T cells that were detected in peripheral blood. (9).

Cancer evades immune surveillance by maintaining a highly immunosuppressive tumor microenvironment. Multiple solid tumors including TNBC have been shown to upregulate PD-1 ligand (PD-L1) surface molecules to modulate immune-regulating checkpoints. (10). PD-1, an inhibitory checkpoint receptor expressed on activated T cells, upon interaction with its ligands PD-L1 or PD-L2 transmits a negative control signal that limits T cell activity. This antitumor immune activity can be potentially restored by blocking PD-1/PD-L1 interaction with antibodies directed against PD-1 or PD-L1. One of the anti-PD-1 antibodies—pembrolizumab showed acceptable safety profile and clinical activity in TNBC patients with the overall response rate of 19% and complete response of just 4%. (11). Currently, there are ongoing phase II and III clinical trials that evaluate pembrolizumab as a monotherapy or in combination with chemotherapy in TNBC patients. (12).

Applicants previously reported that p53MVA vaccine single agent trial participants had significantly higher frequencies of PD-1$^+$ T cells in their peripheral blood than healthy controls. (9). 30 Furthermore, the percentage of PD-1$^+$ T cells and peak of anti-p53 response showed an inverse correlation in the CD8$^+$ T cell compartment. (8). Applicants hypothesized in a previous report that the immunological responses observed in the p53MVA single agent study could be boosted to clinically beneficial levels if the PD-1-mediated immune suppression was inhibited. (13). Hence a phase I clinical trial evaluating the combination of p53MVA and pembrolizumab was initiated.

Results

Patient report. A 69-year-old woman was initially diagnosed with right-sided, cT3N1MO, locally advanced triple negative breast cancer in the Fall of 2008. She received 6 cycles of neoadjuvant docetaxel plus cyclophosphamide therapy, and underwent a mastectomy and axillary lymph node biopsy in June of 2009. Surgical pathology revealed residual ypT1aN1 invasive ductal carcinoma. Approximately 2 months after surgery, there was evidence of dermal recurrence and she received 6 cycles of carboplatin plus gemcitabine followed by adjuvant radiation therapy to the chest wall. Two years later the patient experienced a chest wall recurrence which was biopsy proven. A PET/CT in June 2012 revealed fluorodeoxyglucose (FDG) uptake in the left femur. She was started on capecitabine and denosumab and received radiation therapy to the left-sided femur. Four months later, she suffered a pathological fracture of the left-sided femur which was treated with an intramedullary nailing, while continuing on capecitabine and denosumab. Chemotherapy was switched to second line therapy with paclitaxel upon evidence of dermal progression. In January 2014, she underwent left-sided, proximal femur resection for nonunion and a prosthesis readjustment. Her chemotherapy was changed to third-line therapy with eribulin from February 2014 till January 2015. Due to another episode of dermal metastases progression, chemotherapy was switched to a fourth line therapy with ixabepilone in February 2015. A bone metastases specimen was sent for FoundationOne® genomic analysis which demonstrated a single TP53 D281E mutation. This missense mutation is known to result in a loss of function and overexpression of p53 protein. In July 2015 she was started on fifth line therapy liposomal doxorubicin and completed 3 cycles. Upon clinical examination, worsening dermal lesions were apparent but a PET scan did not show overt visceral disease. In September 2015, she started single-agent, 6th line gemcitabine and completed 3 cycles of treatment. This course of therapy was complicated by thrombocytopenia with continued progression as determined by PET/CT imaging in November 2015, which showed increased FDG uptake and sclerotic osseous lesions in the left side of the ileum and L3 vertebral body. The patient reported increased back pain and was referred to radiation oncology for palliative radiation. Gemcitabine was discontinued. The patient completed palliative radiation to the left ileum and L3 in December 2015, which improved her pain. In January 2016 she developed new dermal lesions on the right upper extremity. The patient enrolled in a clinical trial of PHI-70 (oral FdCyd plus THU) in February 2016. The first cycle was complicated by hospitalizations for grade 3 diarrhea, nausea, vomiting, and abdominal pain. A PET/CT in May 2016 showed increased FDG activity in the left-side iliac bone and a portion of the left iliac wing, and the study drug was held. The patient received her last dose of PHI-70 in June 2016. She was referred to palliative radiation and consideration of hospice care due to no further treatment options. She was referred in August 2016 to City of Hope for a phase I study of p53MVA vaccine in combination with pembrolizumab (FIG. 7A; NCT02432963), at which time, she had clinically evident macular dermal metastases.

Figure 7A:
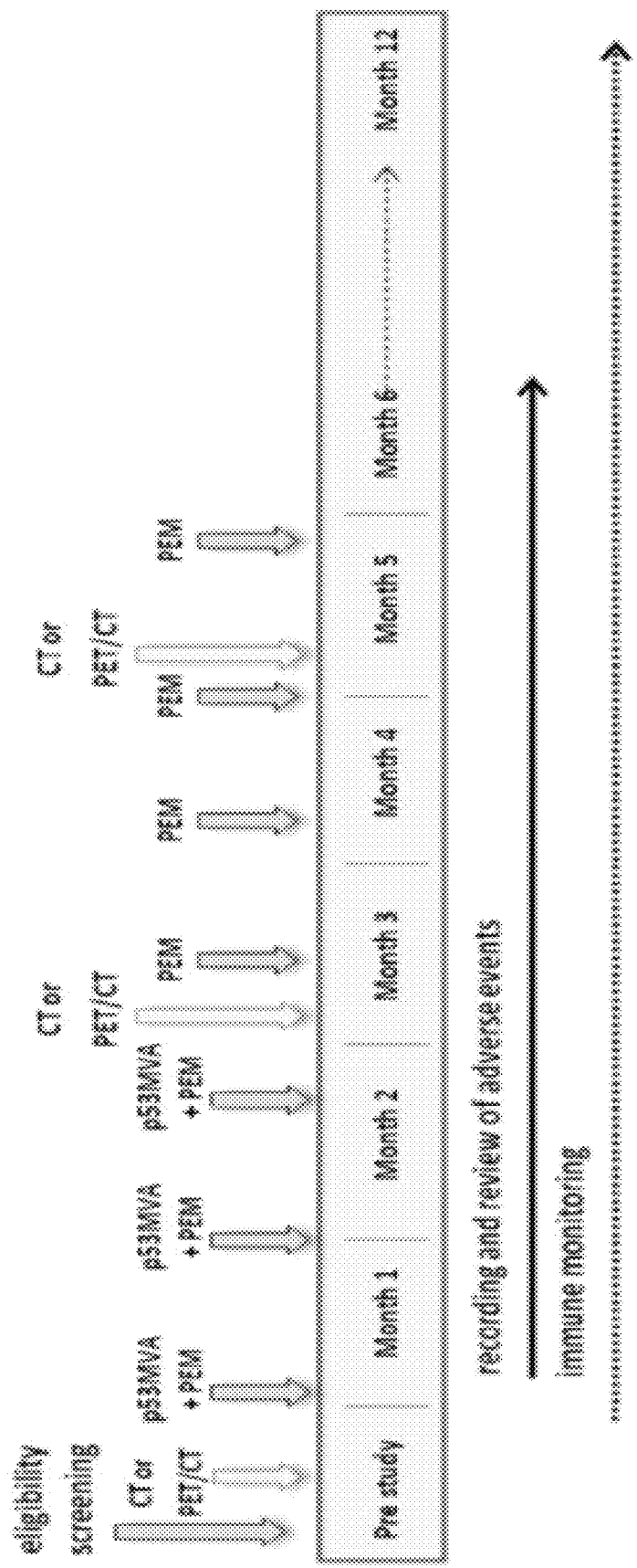
FIGS. 7A-7C. Regression of cutaneous metastases after two doses of p53MVA vaccine and pembrolizumab.
Figure 7B:
Figure 7B:
Figure 7C:
Figure 7C:
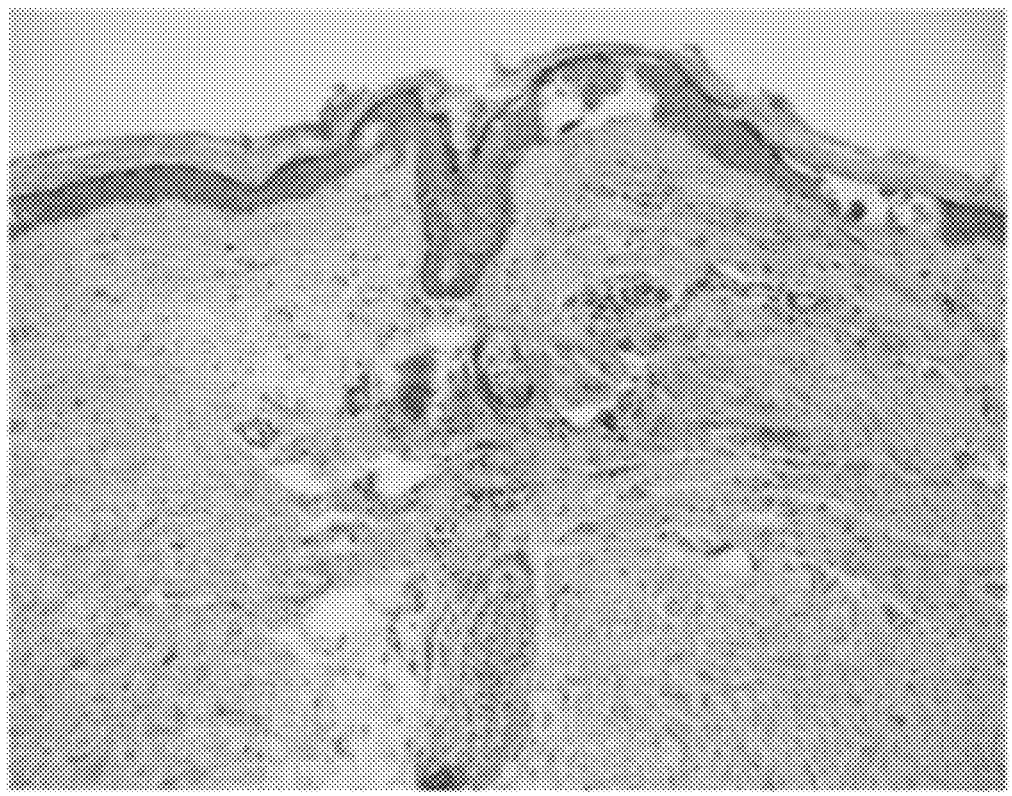

Clinical response. Prior to treatment the patient had diffuse dermal metastases in the form of erythematous macules distributed on her back, chest wall, bilateral arms and thighs, covering at least 50% of her body surface area, which were associated with severe itchiness and pain (FIG. 7B). Pretreatment skin punch biopsy revealed subcutaneous clusters of tumor cells and lymphovascular invasion (FIG. 7C). Immunohistochemistry staining confirmed ER$^-$/PR/HER-2$^-$ status. Additional analysis performed by the Foundation Medicine, Inc. (Morrisville, N.C.) with the use of Ventana PD-L1 (SP142) antibody showed no detectable expression of PD-L1 on tumor cells. While the level of PD-L1 expression has proven to be a useful tool at predicting likelihood of the response to anti-PD-1 treatment, high expression does not guarantee response and low expression does not predict failure. The growing consensus is that patients with PD-L1-negative tumors may still benefit from PD-1/PD-L1 checkpoint inhibitors. (14). The first dose of p53MVA and pembrolizumab was given in August 2016. Six weeks later, dermal metastases showed significant improvement with reduced erythematous macules and itchiness (FIG. 7B, right panel). By week 9, her skin lesions had regressed almost entirely. A skin punch biopsy performed on the same area as the pre-treatment biopsy demonstrated no evidence of residual tumor (FIG. 7C). Restaging CT scan and bone scan in December 2016 showed enhancing nodules in the left lower back musculature as being the same or decreased, concomitant with decreased periosteal signal enhancement compared to August 2016. Of the several bilateral subcentimeter pulmonary nodules present at baseline in August 2016, only one 3 mm nodule remained. During clinic follow up in December 2016, the patient remained free of skin metastases. Post treatment FoundationOne® mutational analysis of paraspinal soft tissue mass biopsy revealed metastatic breast cancer with the following genomic alterations: PTEN Y76*, INPP4B K444*, MLL3 E78fs*17, PIK3R1 1571_L573del, RB1 C278fs*1, TP53 D281E and R209fs*6. Additional disease-relevant genes were found not to be altered: ERBB2, BRCA1 and BRCA2.

FoundationOne® is a next-generation sequencing based assay that identifies genomic alterations within cancer-related genes. This particular assay analyzed 315 genes as well as introns of 28 genes involved in chromosomal genetic rearrangements. The patient tolerated the combined therapy well, with only low grade adverse events reported. The highest grade adverse events recorded as 'possibly attributed' to p53MVA or pembrolizumab were grade 2 nausea and grade 1 vomiting. A transient grade 1 skin rash was reported as 'possibly related' to pembrolizumab.

Although complete clearance of cutaneous metastases was seen as early as 9 weeks into the treatment, dermal disease showed evidence of minimal relapse at week 33 which is apparent at the time of writing of this report. Nevertheless, the patient is alive and enjoying a good quality of life. The patient decided to discontinue her treatment at City of Hope and transferred care to her local oncologist to continue receiving pembrolizumab treatment, near her place of residence several hundred miles away from City of Hope.

Figure 8A:
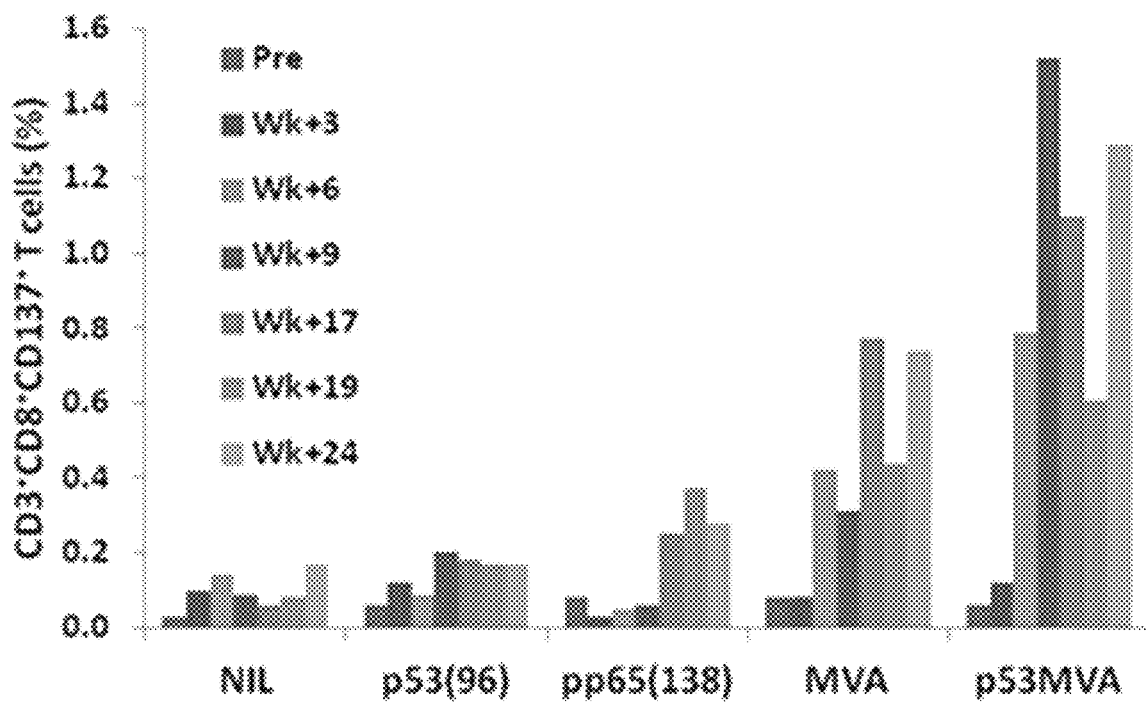
FIGS. 8A-8F. p53MVA/pembrolizumab activate persistent p53-specific CD8$^+$ T cell responses in the blood the timing of which correlates with lymphocytic infiltration of the resolved dermal metastases. The response of CD8$^+$ (FIG. 8A) and CD4$^+$ (FIG. 8B) T cells from PBMCs after 24-h stimulation culture with p53MVA, MVA, p53$_{96}$, and pp65$_{138}$, as determined by flow cytometric analysis. The upregulation of CD137 expression on the surface of CD3$^+$CD8$^+$ T cells reflects increased frequencies of p53-specific T cells in the circulation after vaccination, particularly between weeks 9 and 24. Culture conditions: NIL—medium alone; p53(96)—pool of peptides derived from wild type p53 sequence; pp65(138)—control peptides derived from pp65 CMV; MVA—wild type MVA vaccinia virus; p53MVA—recombinant MVA virus. Bar graphs (FIG. 8C-8F) show the frequency of CD8$^+$ T cell subsets quantified from multiplexed immunohistochemistry skin biopsy sections before and 9 weeks into the treatment. Total CD8$^+$ cell count decreased in the skin tissue at week 9 into the treatment (FIG. 8C). However, increased proportions of CD8$^+$CD137$^+$ (FIG. 8D) and CD8$^+$PD-1$^+$ (FIG. 8E) activated T cells as well as CD8$^+$CD103$^+$ tissue resident effector/memory T cells (FIG. 8F) in the skin tissue at week 9, compared to pre-treatment, suggest that these cells contribute to the elimination of cutaneous metastases in situ.

Immune monitoring studies. Combined therapy activated persistent p53-specific CD8$^+$ T cell responses in the peripheral blood which was associated with lymphocytic infiltration of the resolved dermal metastases (FIGS. 8A-8F). Upregulation of CD137 expression on the surface of CD8$^+$ and CD4$^+$ T cells upon stimulation with p53 peptides and p53MVA reflects increased frequencies of p53-specific T cells in the circulation after vaccination, particularly between weeks 9 and 24 (FIGS. 8A and B). Skin infiltrating CD8$^+$ T cells were visualized and quantified by multiplex immunohistochemistry analysis of tissue sections (FIGS. 8C-8F). All the immune cells, including CD8$^+$ T cells (FIG. 8C), were notably decreased in numbers compared to the pre-treatment tissue but percentages of CD137$^+$ (FIG. 8D) and PD-1$^+$ (FIG. 8E) CD8$^+$ activated T cells as well as tissue resident effector/memory CD8$^+$CD103$^+$ T cells (FIG. 8F) were increased. The presence of these critical subsets of CD8$^+$ T cells in situ suggests their role during the successful immune effector phase of therapy.

Figure 9A:
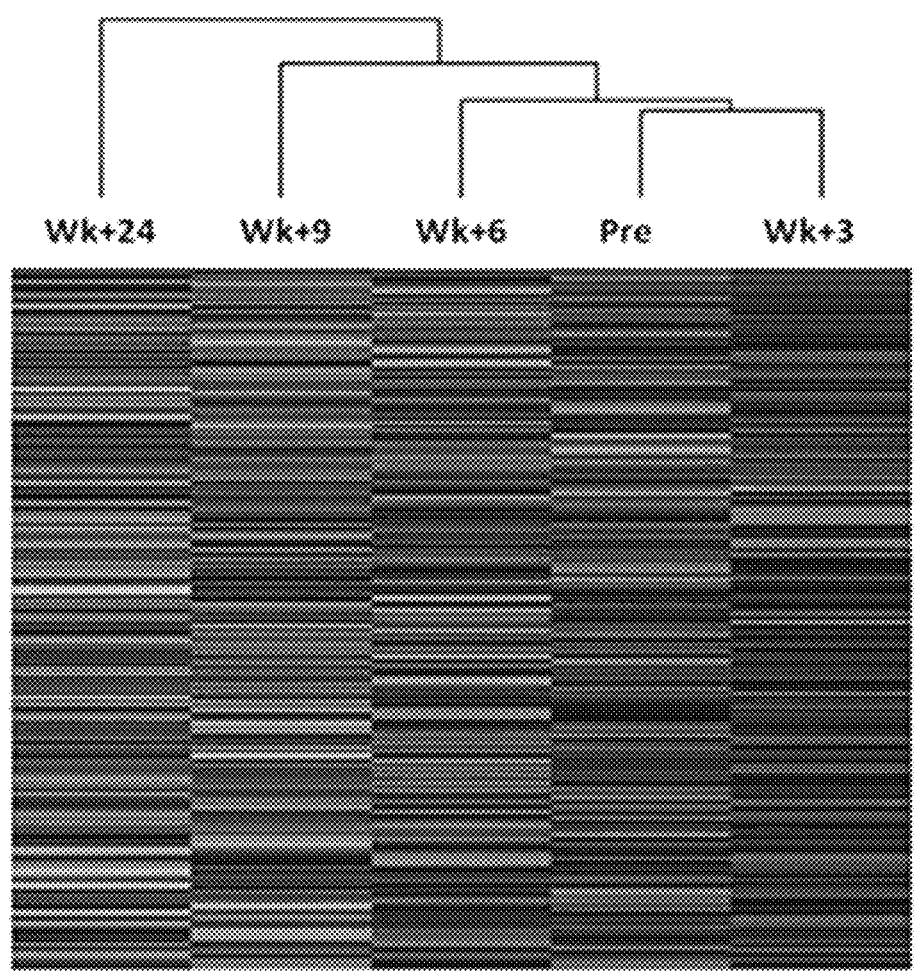
FIGS. 9A-9D. Multiplexed gene expression analysis of PBMC samples using nCounter PanCancer Immune Profiling Panel.
Figure 9B:
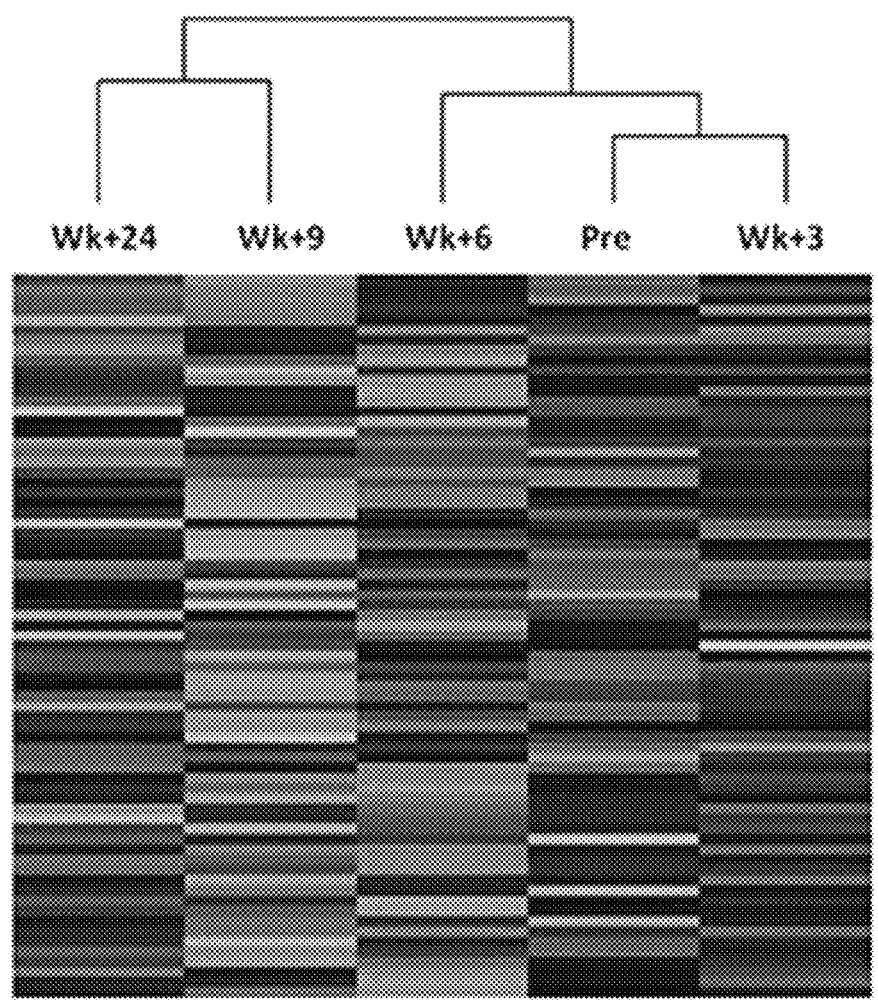
Figure 9C:
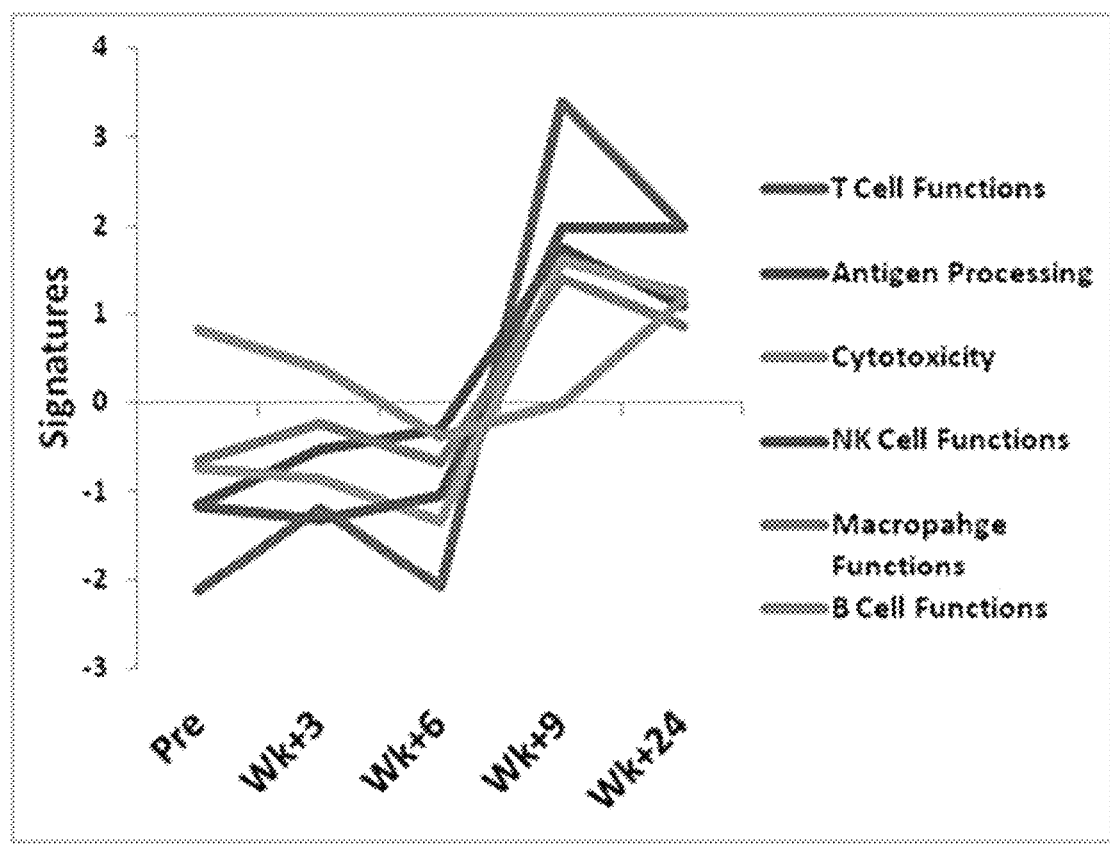
Figures 9D, 10:
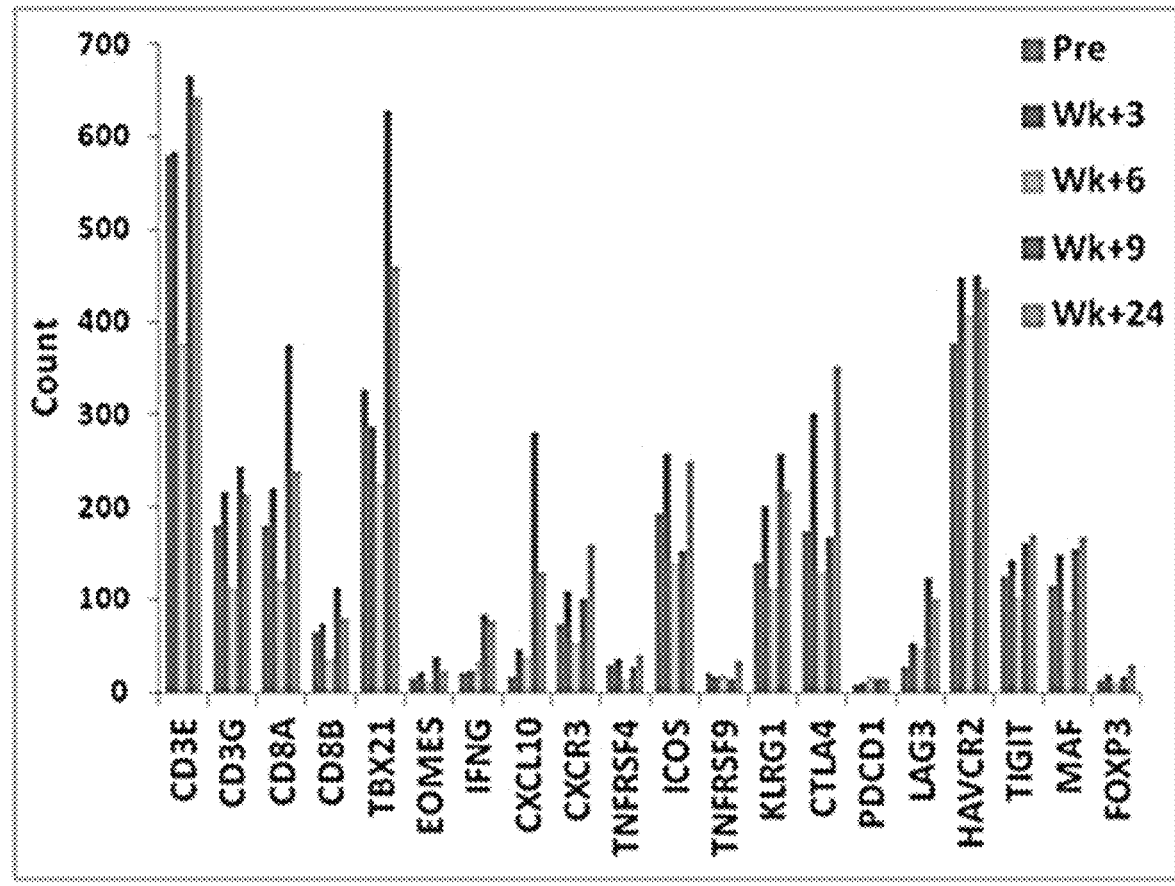
FIG. 10. Quality of RNA samples used for NanoString analysis with nCounter PanCancer Immune Profiling Panel.
Figure 10:
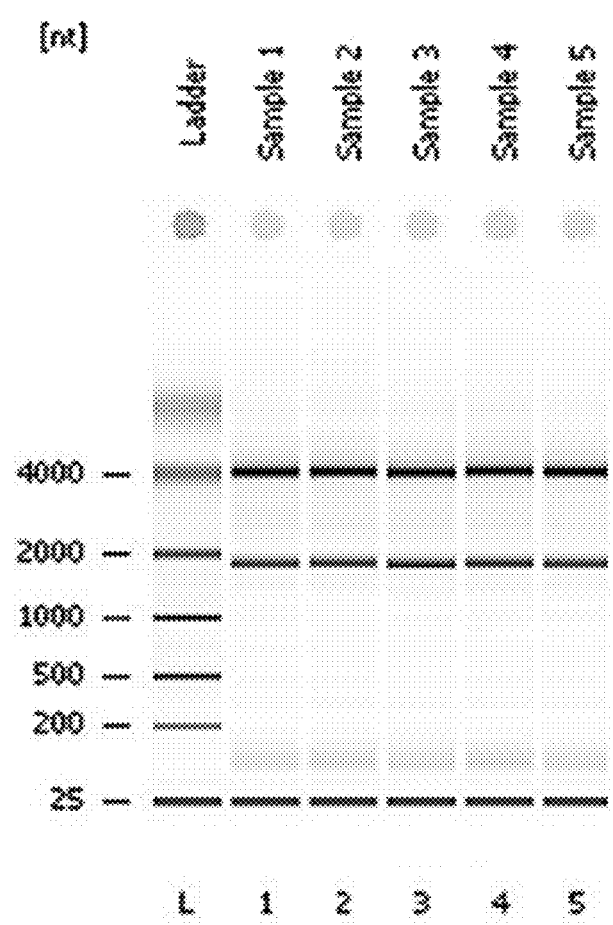
Figure 10:
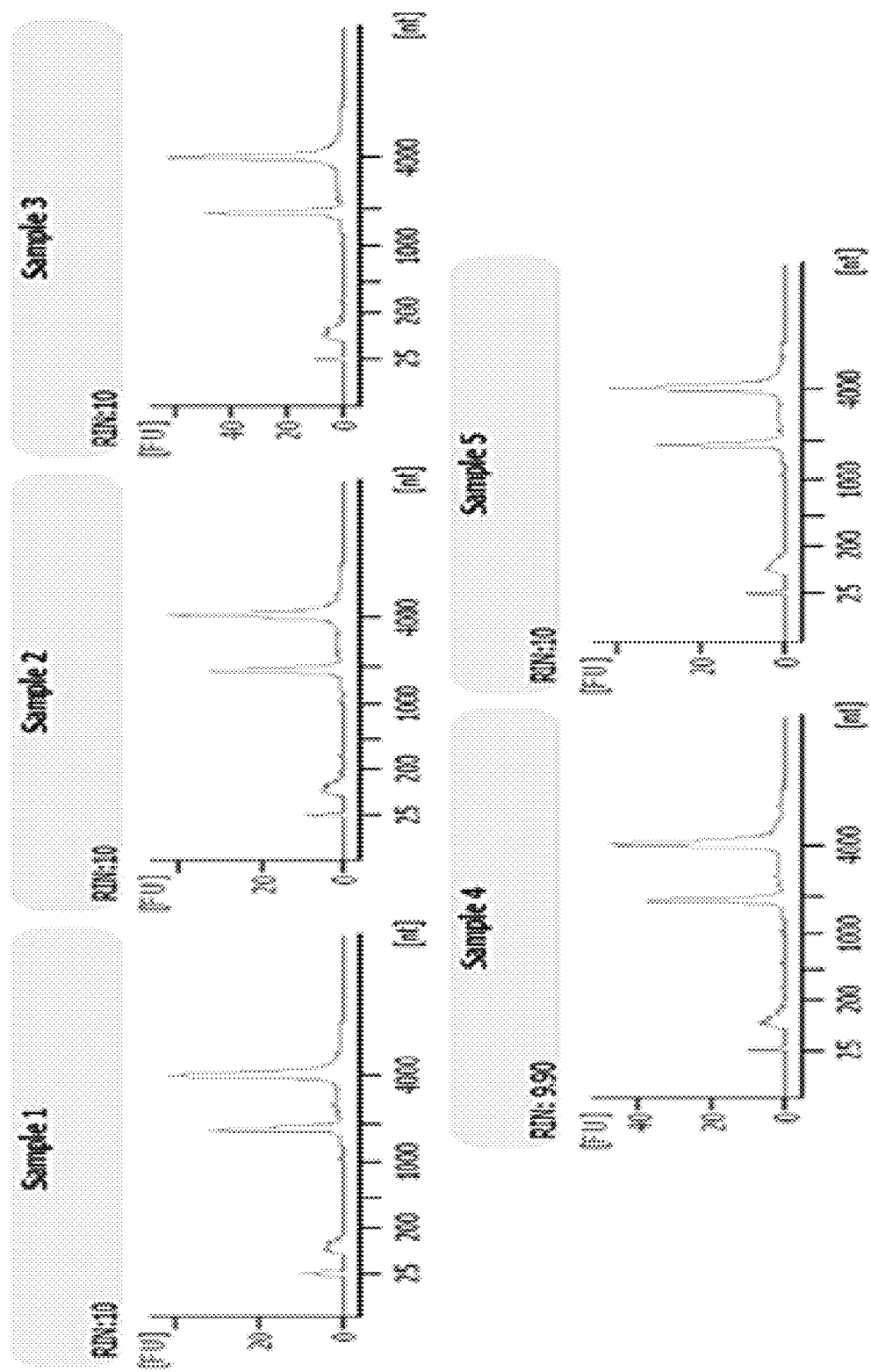
Figure 11:
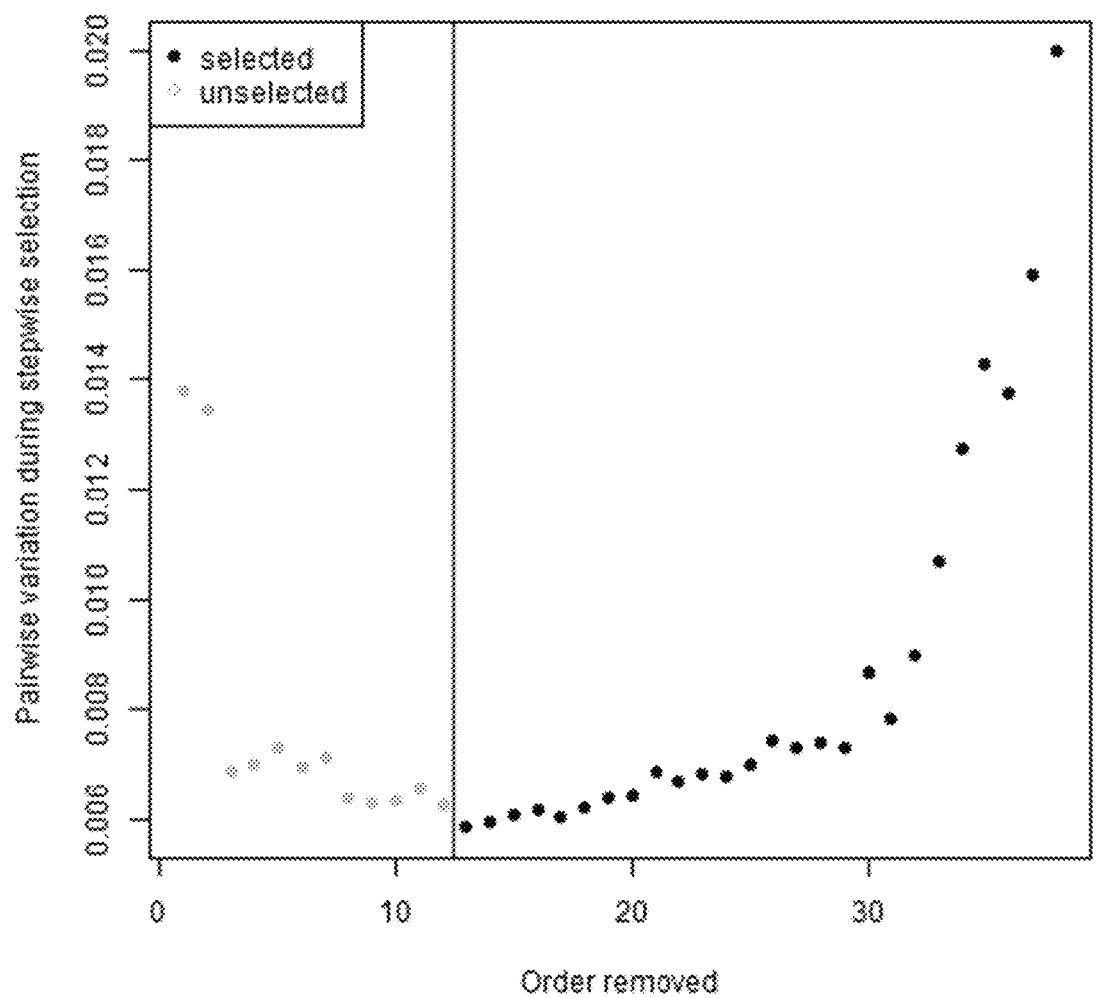
FIG. 11. Pairwise variance during housekeeping gene selection. The plot displays the geNorm pairwise variation statistic after successive genes are removed. This statistic cannot be computed for the final two genes, which are therefore not displayed. The ideal normalization gene set minimizes the pairwise variation statistic.

Multiplexed gene expression analysis of PBMC samples. Five PBMC samples were assessed for differential expression of immune profile and T cell function genes (FIGS. 9A-9D). As seen by the dendrograms on heat maps, PBMC samples collected 9 and 24 weeks after initiation of treatment showed visible segregation from the week 6, 3 and pre-treatment samples. The transcriptome of the T cell function data (FIG. 9B) with its peaks of activity at weeks 9 and 24 overlaps the heat map of all PBMC data (FIG. 9A), indicating a prominent role of T cell populations during the response to p53MVA vaccine and pembrolizumab. T cell gene expression and associated immune response categories such as antigen processing, cytotoxicity, macrophage and NK cell functions peaked at weeks 9 and 24 (FIG. 9C). Numerous markers of successful T cell stimulation were elevated post treatment, including durable upregulation of T-bet (TBX21), Eomes, OX40 (TNFRSF4), CXCR3, IFN-γ, CXCL10, and KLRG1 (FIG. 9D). At the same time, upregulation of genes associated with T cell inhibition or exhaustion were also seen, such as CTLA-4, LAG-3, TIM-3 (HAVCR2), TIGIT, and MAF (FIG. 9D). These molecules and their signaling properties may play a role in determining the balance between activation/duration and inhibition/exhaustion of T cell immune responses which may in turn critically influence the clinical outcome of the treatment.

Figure 8B:
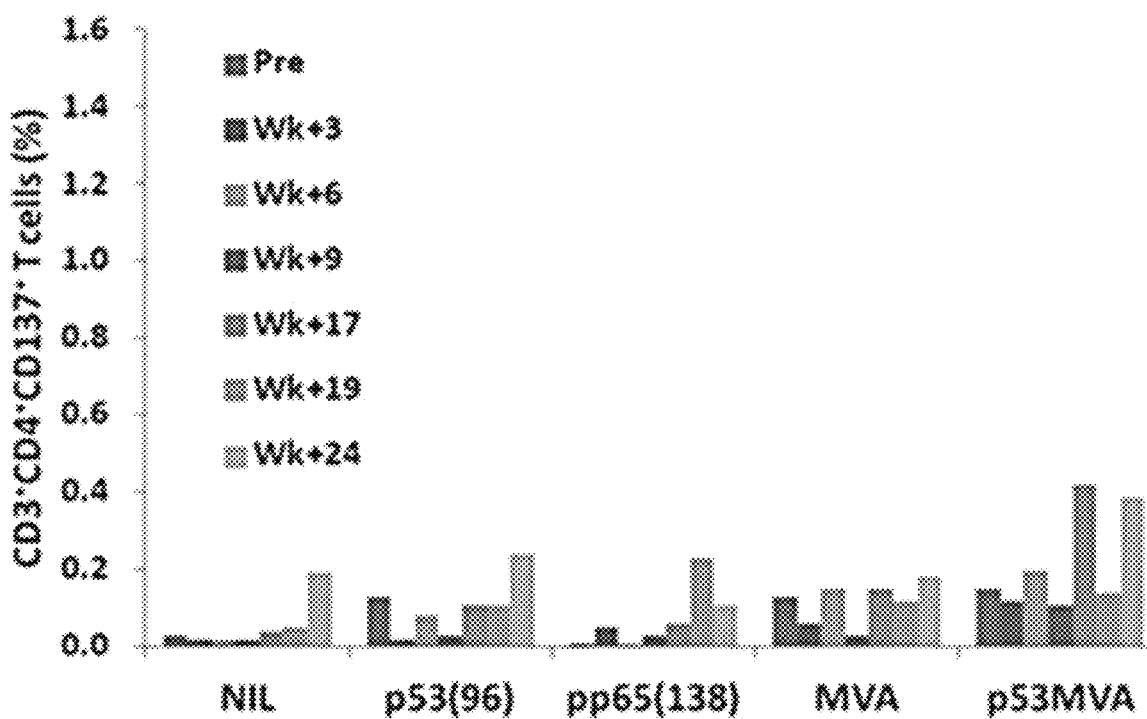
Figure 8C:
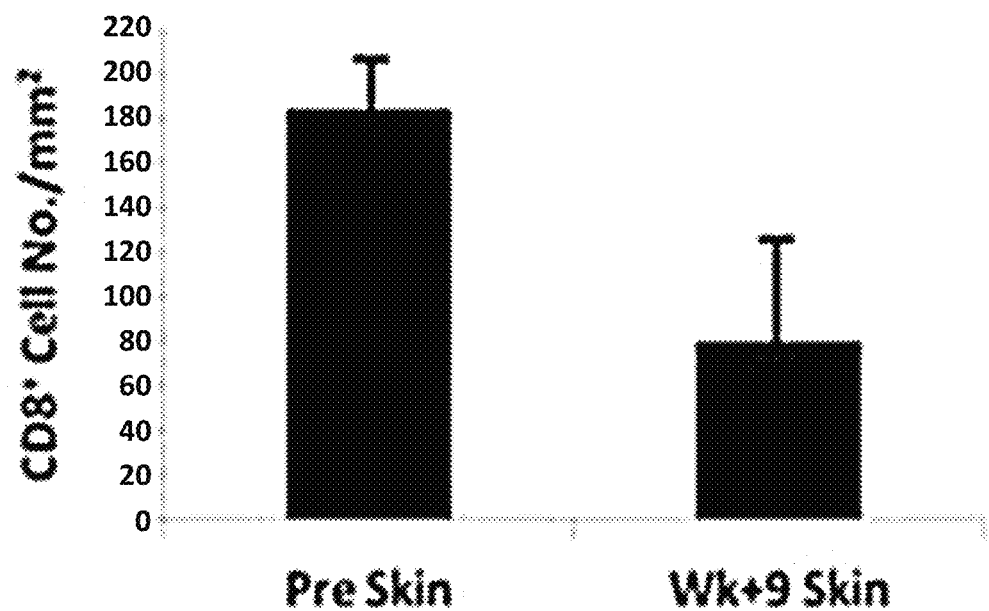
Figure 8D:
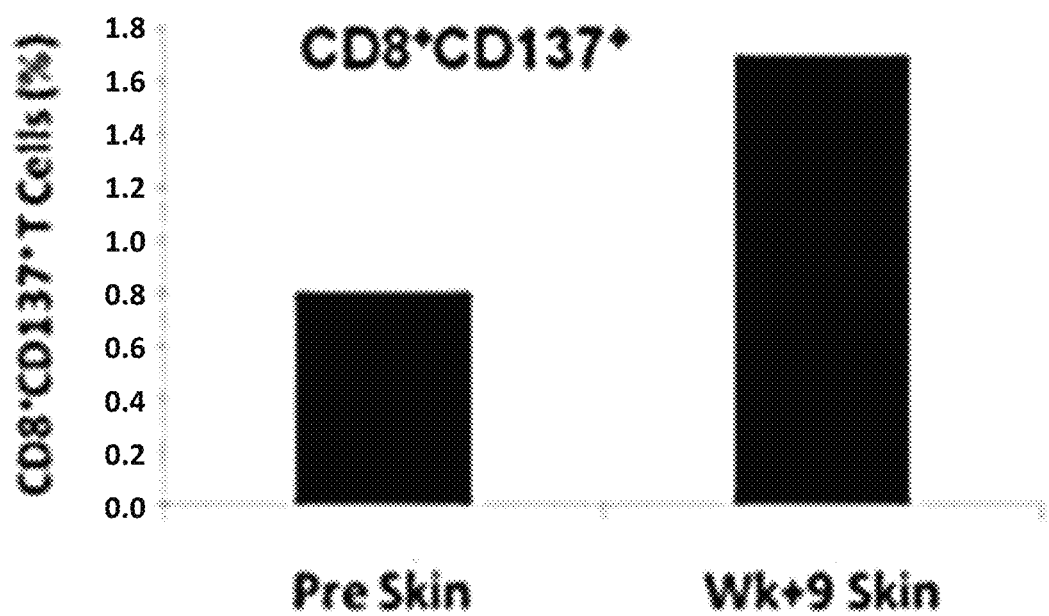
Figure 8E:
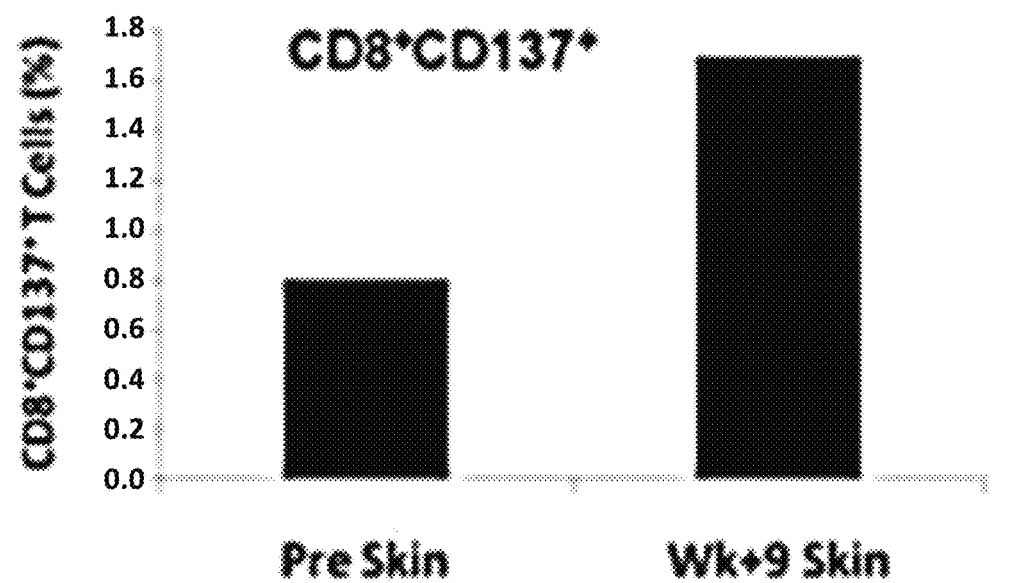
Figure 8F:
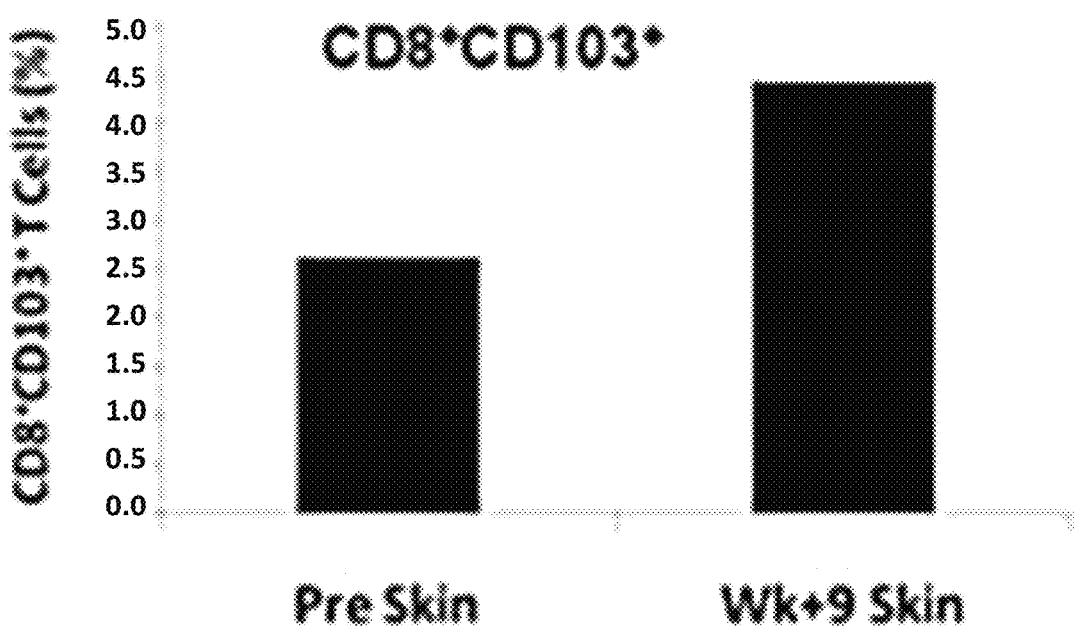

Discussion. This example describes a rapid clinical response after targeting of overexpressed tumoral p53 in combination with PD-1 blockade. This response was sustained for six months and led to a dramatic improvement in quality of life for the patient. While it is difficult to distinguish the relative effects of the vaccine and pembrolizumab, a specific anti-p53 response was stimulated by combined therapy and demonstrated by increased frequencies of p53-responsive T cells detected in vitro (FIGS. 8A and 8B). The clinical response was associated with upregulation of multiple immune response genes in peripheral blood cells most prominently those associated with T cell functions (FIGS. 9A-9D).

An interesting aspect of p53 as a target antigen for the immune system is its mutational status. The TP53 gene is mutated in over 80% of TNBC (as opposed to 25% of other breast cancers) patients providing an additional rationale for targeting the p53 protein in this novel approach for the treatment of TNBC. (15, 16). This high mutation rate and p53 protein overexpression have been associated with poor response to chemotherapy and reduced survival. The patient presented in this study responded successfully to the p53MVA/pembrolizumab administration with the generation of p53-specific T cell responses directed against wild type p53 epitopes (FIGS. 8A and 8B). However, there is a possibility that T cell responses were also directed against neoantigenic epitopes derived from mutated sequences of the p53, especially after activation of systemic and local immune responses with enhanced antigen presenting functions (FIG. 9C). TP53 genomic alterations identified in this patient included D281E missense and R209fs* deletion/frameshift mutations. While deletion or nonsense mutations lead to low or no expression of p53, missense mutations typically lead to the production of full-length altered p53 protein with a prolonged half-life. (17). Applicants have attempted to identify potential neoepitopes in the mutated sequence of the p53 using prediction algorithms of the Immune Epitope Database and Analysis Resource (world wide web iedb.org). Single amino acid substitution D281E did not produce any predicted epitopes that would bind to patient's HLA class I molecules with high, medium, or even low affinity. The best binder identified was a 10-mer CPGRERRTEE (SEQ ID NO:2) that would potentially bind to HLA-B*0702 with very low affinity (IC$_{50}$=2536 nM). In contrast, this analysis predicted 27 HLA class I epitopes in the wild type p53 sequence that would bind with high affinity at IC$_{50}$<50 nM (Table 6). The patient's class I HLA type is also shown in the box with the Table 6. Based on the results of this in silico analysis Applicants decided not to pursue any functional studies directed at identification of T cell clones specific for putative neoepitopes. p53MVA vaccine with the TP53 transgene that has no patient-specific mutated sequences, has the characteristics of a "universal" vaccine that can function across HLA restriction barriers to activate patient-specific anti-p53 immune responses.

A considerable hurdle to successful immunotherapy is the intrinsic and acquired immuno-suppression seen in cancer patients. This dramatic, complete dermal response showed that a cancer antigen-specific vaccine given in combination with PD-1 immune checkpoint blockade can stimulate an immune response that is associated with durable clinical benefit in heavily pretreated patients. Progressive loss of the ability to respond to TCR stimuli and upregulation of inhibitory coreceptors that desensitize T cells to tumor antigens are well described phenomena. This may be particularly relevant in older cancer patients with senescent immune systems, subjected to multiple rounds of immune suppressive anti-cancer treatments. The TCR stimulation by tumor antigens during the immune checkpoint blockade therapy acquires even greater significance in light of recent reports showing that tumor antigen-specific CD8$^+$ T cells targeted by anti-PD-1 therapies require CD28 costimulation to be rescued from exhaustion. (18,19). In this respect, the p53MVA vaccine offers an efficient way to naturally stimulate TCR/CD28 signaling by professional antigen-presenting cells and to benefit from its combination with PD-1 blockade.

There are currently several clinical studies examining cancer vaccines combined with PD-1 blockade (listed by ClinicalTrials.gov). However the majority of these studies employ cell and peptide based vaccines. Using a viral based vaccine to deliver a tumor antigen is a more physiological and potentially efficient way to generate a complete immune response involving innate and adaptive components and durable immune memory. This dramatic response, in a patient who had no further treatment options, justifies further exploration of this combination therapy. Moreover, in Applicants' ongoing phase I clinical trial of p53MVA and pembrolizumab (NCT02432963) Applicants have been monitoring elevated p53-specific T cell immunity in two patients showing stable metastatic disease for 7 months (TNBC patient) and 6 months (patient with head and neck squamous cell carcinoma).

Materials and Methods

Study patient and treatment regimen. City of Hope Institutional Review Board (IRB #15002) approved the study registered with ClinicalTrials.gov (NCT02432963). All patients provided written informed consent for participation in this study, including treatment, collection of blood, and data analysis in accordance with the ethical institutional standards and with the 1975 Helsinki Declaration. The primary objective is to establish safety and tolerability of the p53MVA vaccine in combination with pembrolizumab. The secondary objectives are to provide evidence of enhanced cellular immunity to p53 and evaluate the response rate and progression free survival. The treatment schedule for this study is shown in FIG. 7A. p53MVA and pembrolizumab are given concurrently for three doses, every three weeks. Pembrolizumab is administered first IV (200 mg), followed by IM injection of p53MVA ($5.6 \times 10^8$ pfu) at least 30 minutes later. This was followed by four doses of pembrolizumab alone every 3 weeks. The patient was assessed for toxicity and clinical response. Immunological assessments were performed on peripheral blood mononuclear cells (PBMC) and skin biopsy tissue. Adverse events were classified using the NCI Common Toxicity Criteria for Adverse Events (CTCAE) v4.3. Imaging was performed pre-study, and every two months according to standard of care. Histopathology examination of skin punch biopsies pre- and post-therapy by standard H&E staining was also performed.

Trial agents. p53MVA was manufactured using GMP-grade materials at the Center for Biomedicine and Genetics at City of Hope. The final product was diluted in PBS with 7.5% lactose at a concentration of $5.6 \times 10^8$ pfu/ml. Pembrolizumab (KEYTRUDA®, Merck & Co., Inc.) was provided through the clinical trial and continued with the compassionate use program from Merck upon completion of the trial.

Monitoring of T cell immune responses. Peripheral blood samples were obtained at study entry and at weeks 3, 6, 9 and 24 after initiation of therapy. PBMC prepared by ficoll gradient separation were cryopreserved until analysis. In the initial analysis PBMC were thawed and plated at $2 \times 10^5$ cells/0.2 ml/well in media (RPMI, FBS 10%, glutamine 2 mM, sodium pyruvate 1 mM, non-essential amino acids) with one of the following stimuli: media alone, p53MVA, MVA, pool of 96 15-mer overlapping peptides spanning the entire length of p53 (p53$_{96}$; 5 µg/ml; synthesized in-house), and a pool of 138 peptides derived from CMV pp65 protein epitopes (pp65$_{138}$; 2 µg/ml; BEI Resources, NIH, Bethesda). After 24 h of culture, the cells were stained with the following antibodies: CD3, CD4, CD8, CD137 (BD Biosciences, San Diego, Calif.) and analyzed by flow cytometry (BD FACSCelesta, BD Biosciences, San Jose, Calif.). Data acquired in FACSDiva (BD Bioscience) were analyzed in FlowJo (Flowjo LLC, Ashland, Oreg.).

Multiplexed immunohistochemistry analysis of skin punch biopsies. FFPE sample blocks were cut into 3-µm thick slides and labeled with combinations of the following antibodies: CD3, CD4, CD8, CD103, CD137, and PD-1 by using the multiplex IHC opal method. (20). Approximately 10-20 FOV (field-of-view: 0.70×0.52 mm) containing either tumor cells and/or immune cells were selected for image acquisition and cell counting using PerkinElmer Vectra automated quantitative pathology imaging system and inForm software analysis (PerkinElmer, Waltham, Mass.).

Profiling of immune function gene expression. Total RNA was isolated from patient PBMC samples using miRNeasy mini kit (Qiagen, Valencia, Calif.). RNA concentration was assessed with the Nanodrop spectrophotometer ND-1000 and Qubit 3.0 Fluorometer (Thermo Scientific, Waltham, Mass.). RNA fragmentation and quality control was determined by 2100 Bioanalyzer (Agilent, Santa Clara, Calif.) (FIG. 10). All samples were normalized to 20 ng/µL. RNA expression was analyzed by NanoString nCounter platform (NanoString Technologies, Seattle, Wash.) by digitally detecting and counting in a single reaction without amplification. nCounter PanCancer Immune Profiling Panel (Cat XT-CSO-HIP1-12) from NanoString was used. This 770-plex gene expression panel covers innate and adaptive immune responses, inflammation, adhesion molecules, chemokines, cytokines and pattern recognition receptors. Each assay included 6 positive and 6 negative RNA assay controls, plus 40 mRNA housekeeping controls. 100 ng of RNA was first hybridized with codeset from the gene panel at 65° C. for 16 hours. Post-hybridization probe-target mixture was quantified with nCounter Digital Analyzer and all data analyzed in nSolver software package (NanoString).

TABLE 5

List of genes that define immune function pathways presented in FIG. 9C.
HUGO Name

| T-Cell Functions | Antigen Processing | Cytototxicity | NK Cell Functions | Macrophage Functions | B Cell Functions |
|---|---|---|---|---|---|
| ADA | CD1E | GNLY | CCR1 | CD47 | ADA |
| AICDA | CD8A | GZMA | CD2 | CD80 | BLK |
| CCR1 | HLA-A | GZMB | CD7 | CD86 | CD10 |
| CCR4 | HLA-B | GZMH | CXCL11 | CSF2 | CD19 |
| CCR5 | HLA-C | GZMK | CXCR3 | DPP4 | CD27 |
| CD1C | HLA-DMA | GZMM | IFNG | F2RL1 | CD274 |

TABLE 5-continued

List of genes that define immune function pathways presented in FIG. 9C.
HUGO Name

| T-Cell Functions | Antigen Processing | Cytotoxicity | NK Cell Functions | Macrophage Functions | B Cell Functions |
|---|---|---|---|---|---|
| CD1D | HLA-DMB | HLA-A | IL12A | IFNG | CD38 |
| CD2 | HLA-DOB | HLA-B | IL12B | LBP | CD3E |
| CD27 | HLA-DPA1 | HLA-C | IL12RB1 | LCP1 | CD5 |
| CD274 | HLA-DPB1 | PRF1 | IL12RB2 | PRKCE | CD70 |
| CD38 | HLA-DQA1 | | IL18 | PSEN2 | CD79B |
| CD3E | HLA-DQB1 | | IL18R1 | SBNO2 | CD80 |
| CD3G | HLA-DRA | | IL18RAP | SLC11A | CD86 |
| CD47 | HLA-DRB3 | | IRF1 | SYK | CR2 |
| CD5 | HLA-DRB4 | | ITGA1 | TICAM1 | CTLA4 |
| CD7 | MR1 | | KIR_Activating_Subgroup_1 | | CXCR5 |
| CD70 | PSMB7 | | KIR_Activating_Subgroup_2 | | FAS |
| CD80 | PSMB9 | | KIR_Inhibiting_Subgroup_1 | | IL11 |
| CD86 | TAP1 | | KIR_Inhibiting_Subgroup_2 | | IRF4 |
| CD8A | TAP2 | | KIR3DL1 | | PTPRC |
| CD8B | TAPBP | | KIR3DL2 | | RAG1 |
| CTLA4 | THBS1 | | KLRB1 | | SOCS1 |
| CXCL10 | | | KLRC1 | | TNFRSF14 |
| CXCL11 | | | KLRC2 | | TNFSF18 |
| CXCL9 | | | KLRD1 | | |
| CXCR3 | | | KLRF1 | | |
| CXCR5 | | | KLRG1 | | |
| DPP4 | | | KLRK1 | | |
| EGR1 | | | LILRB1 | | |
| EOMES | | | NCR1 | | |
| F2RL1 | | | | | |
| FAS | | | | | |
| FOXP3 | | | | | |
| IDO1 | | | | | |
| IFNG | | | | | |
| IL11 | | | | | |
| IL12A | | | | | |
| IL12B | | | | | |
| IL12RB1 | | | | | |
| IL12RB2 | | | | | |
| IL13 | | | | | |
| IL13RA1 | | | | | |
| IL13RA2 | | | | | |
| IL18 | | | | | |
| IL18R1 | | | | | |
| IL18RAP | | | | | |
| IL2 | | | | | |
| IL3 | | | | | |
| IL4 | | | | | |
| IL4R | | | | | |
| IL5 | | | | | |
| IRF1 | | | | | |
| IRF4 | | | | | |
| ITGA1 | | | | | |
| LAG3 | | | | | |
| LCK | | | | | |
| LCP1 | | | | | |
| LILRB1 | | | | | |
| MAF | | | | | |
| MS4A1 | | | | | |
| PTPRC | | | | | |
| RAG1 | | | | | |
| SOCS1 | | | | | |
| STAT4 | | | | | |
| STAT6 | | | | | |
| TBX21 | | | | | |
| TIGIT | | | | | |
| TNFRSF14 | | | | | |
| TNFSF14 | | | | | |
| TNFSF18 | | | | | |
| TP53 | | | | | |

TABLE 6

Examples of predicted HLA class I high affinity binding epitopes derived from wild type p53 sequence. The patient's class I HLA type is shown in the box at right-hand side.

| Allele | Peptide | IC$_{50}$ [nM] | Percentile Rank |
|---|---|---|---|
| HLA-A*03:01 | AKSVTCTYSPALNK | 17.84 | 0.10 |
| HLA-A*02:01 | NKMFCQLAKTCPV | 41.95 | 0.10 |
| HLA-A*03:01 | KSVTCTYSPALNK | 15.73 | 0.10 |
| HLA-A*03:01 | SVTCTYSPALNK | 27.64 | 0.10 |
| HLA-A*02:01 | KMFCQLAKTCPV | 29.79 | 0.10 |
| HLA-B*07:02 | APAPAPSWPL | 22.81 | 0.15 |
| HLA-A*03:01 | CTYSPALNK | 6.71 | 0.15 |
| HLA-A*03:01 | VTCTYSPALNK | 32.16 | 0.15 |
| HLA-A*03:01 | KSVTCTYSPALNKM | 31.64 | 0.20 |
| HLA-B*07:02 | SPLPSQAM | 40.96 | 0.20 |
| HLA-B*07:02 | APRVAPAPAA | 27.01 | 0.20 |
| HLA-B*07:02 | APRVAPAPA | 9.29 | 0.20 |
| HLA-B*07:02 | APAAPTPAA | 15.7 | 0.20 |
| HLA-B*07:02 | RPILTIITL | 31.53 | 0.20 |
| HLA-A*03:01 | RVRAMAIYK | 12.32 | 0.20 |
| HLA-B*07:02 | LPENNVLSPL | 44.27 | 0.30 |
| HLA-B*07:02 | SPQPKKKPL | 8.14 | 0.30 |
| HLA-C*05:01 | YLDDRNTFR | 25.02 | 0.35 |
| HLA-B*07:02 | LPPGSTKRAL | 47.12 | 0.35 |
| HLA-C*07:02 | FRHSVVVPY | 30.95 | 0.35 |
| HLA-A*03:01 | GSRAHSSHLK | 48.93 | 0.45 |
| HLA-A*03:01 | TSRHKKLMFK | 25.32 | 0.45 |
| HLA-A*02:01 | NLLGRNSFEV | 37.12 | 0.50 |
| HLA-B*07:02 | APSWPLSSSV | 45.96 | 0.55 |
| HLA-A*02:01 | FLHSGTAKSV | 17.47 | 0.55 |
| HLA-A*02:01 | LLGRNSFEV | 24.2 | 0.60 |
| HLA-A*03:01 | KTYQGSYGFR | 30.76 | 0.75 |

HLA-A*0201
HLA-A*0301
HLA-B*0702
HLA-B*4402
HLA-C*0501
HLA-C*0702

IC$_{50}$ = half maximal inhibitory concentration.
Low percentile rank = good binders
(Immune Epitope Database and Analysis Resource: world wide web iedb.org)

REFERENCES FOR EXAMPLE 8

1. Bianchini et al, Nature Rev Clin Oncol 2016; 13(11):674-90; PMID:27184417.
2. Masuda et al, Clin Cancer Res 2013; 19(19):5533-40; PMID:23948975.
3. Arpino et al, Breast 2013; 22(2):109-20; PMID: 23462680.
4. Olivier et al, Cold Spring Harb Perspect Biol 2010; 2(1):a001008; PMID:20182602.
5. Bueter et al, Int J Oncol 2006; 28(2):519-25; PMID: 16391808.
6. Song et al, Cancer Immunol Immunother 2007; 56(8): 1193-205; PMID: 17219151.
7. Song et al, Cancer Invest 2011; 29(8):501-10; PMID: 21843052.
8. Liu et al, Cancer Res 2000; 60(3); 693-701; PMID: 10676655.
9. Hardwick et al, Clin Cancer Res 2014; 20(17):4459-70; PMID:24987057.
10. Mittendorf et al, Cancer Immunol Res 2014; 2(4):361-70; PMID:24764583.
11. Nanda et al, J Clin Oncol 2016; 34(21):2460-7; PMID: 27138582.
12. Hartkopf et al, Breast Care 2016; 11(6):385-90; PMID: 28228704.
13. Hardwick et al, Oncoimmunology 2014; 3(10):e958949; PMID:25941580.
14. Topalian et al, Nat Rev Cancer 2016; 16(5):275-87; PMID:27079802.
15. Shah et al, Nature 2012; 486(7403):395-9; PMID: 22495314.
16. Cancer Genome Atlas Network. Nature 2012; 490 (7418):61-70; PMID:23000897.
17. Freed-Pastor et al, Genes Dev 2012; 26(12):1268-86; PMID:22713868.
18. Kamphorst et al, Science 2017; 355(6332):1423-7; PMID:28280249.
19. Hui et al, Science 2017; 355(6332):1428-33; PMID: 28280247.
20. Stack et al, Methods 2024; 70(1):46-58; PMID: 25242720.

Yuan et al, Complete regression of cutaneous metastases with systemic immune response in a patient with triple negative breast cancer receiving p53MVA vaccine with pembrolizumab, OncoImmunology, Volume 6, Issue 12, published on line Aug. 11, 2017.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The detailed description of the disclosure is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

What is claimed is:

1. A method of treating a cutaneous metastasis in a human having triple negative breast cancer in need thereof, the method comprising administering to the human an effective amount of a modified vaccinia Ankara p53-targeting vaccine that expresses a nucleic acid sequence having at least 90% sequence identity to SEQ ID NO:1 and an effective amount of pembrolizumab.

2. The method of claim 1, wherein the cancer overexpresses p53, expresses a p53 mutant protein, or a combination thereof.

3. The method of claim 1, wherein the effective amount of pembrolizumab is from about 100 mg to about 300 mg.

4. The method of claim 1, wherein the modified vaccinia Ankara p53-targeting vaccine expresses a nucleic acid sequence comprising SEQ ID NO:1.

5. The method of claim 1, wherein the effective amount of the modified vaccinia Ankara p53-targeting vaccine is from about $1.9 \times 10^8$ pfu to about $6.5 \times 10^8$ pfu.

6. The method of claim 5, wherein the effective amount of the modified vaccinia Ankara p53-targeting vaccine is from about $1.9 \times 10^8$ pfu to about $3.7 \times 10^8$ pfu.

7. The method of claim 5, wherein the effective amount of the modified vaccinia Ankara p53-targeting vaccine is from about $4.7 \times 10^8$ pfu to about $6.5 \times 10^8$ pfu.

8. A method of treating a cutaneous metastasis in a human having triple negative breast cancer in need thereof, the method comprising administering to the human:
- from about $1.9 \times 10^8$ pfu to about $6.5 \times 10^8$ pfu of a modified vaccinia Ankara p53-targeting vaccine that expresses a nucleic acid sequence having at least 95% sequence identity to SEQ ID NO:1; and
- (ii) from about 100 mg to about 300 mg of pembrolizumab;

wherein the triple negative breast cancer overexpresses p53, expresses a p53 mutant protein, or a combination thereof.

9. The method of claim 8, comprising administering to the human from about $1.9 \times 10^8$ pfu to about $3.7 \times 10^8$ pfu of the modified vaccinia Ankara p53-targeting vaccine.

10. The method of claim 8, comprising administering to the human from about $4.7 \times 10^8$ pfu to about $6.5 \times 10^8$ pfu of the modified vaccinia Ankara p53-targeting vaccine.

11. The method of claim 8, wherein the modified vaccinia Ankara p53-targeting vaccine expresses a nucleic acid sequence comprising SEQ ID NO:1.

12. The method of claim 8, wherein both the modified vaccinia Ankara p53-targeting vaccine and pembrolizumab are administered to the subject once every three weeks for a total of 3 administrations, and thereafter only the pembrolizumab is administered to the subject once every three weeks.

13. The method of claim 1, wherein both the modified vaccinia Ankara p53-targeting vaccine and pembrolizumab are administered to the subject once every three weeks for a total of 3 administrations, and thereafter only the pembrolizumab is administered to the subject once every three weeks.

* * * * *

SEQUENCE LISTING

<160> NUMBER OF SEQ ID NOS: 2

<210> SEQ ID NO 1
<211> LENGTH: 1182
<212> TYPE: DNA
<213> ORGANISM: Homo sapiens

<400> SEQUENCE: 1

```
atggaggagc cgcagtcaga tcctagcgtc gagcccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca    180
gatgaagctc ccagaatgcc agaggctgct ccccgcgtgg ccctgcacc agcagctcct     240 acaccggcgg ccctgcacc agcccctcc tggcccctgt catcttctgt cccttcccag      300
aaaacctacc agggcagcta cggtttccgt ctgggcttct tgcattctgg gacagccaag    360
tctgtgactt gcacgtactc ccctgccctc aacaagatgt tttgccaact ggccaagacc    420
tgccctgtgc agctgtgggt tgattccaca ccccgcccg gcacccgcgt ccgcgccatg     480
gccatctaca agcagtcaca gcacatgacg gaggttgtga ggcgctgccc ccaccatgag    540
cgctgctcag atagcgatgg tctggcccct cctcagcatc ttatccgagt ggaaggaaat    600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg aacagctttt gaggtgcatg tttgtgcctg tcctgggaga    840
gaccggcgca cagaggaaga gaatctccgc aagaaagggg agcctcacca cgagctgccc    900
ccagggagca ctaagcgagc actgtccaac aacaccagct cctctcccca gccaaagaag    960
aaaccactgg atggagaata tttcacccctt cagatccgtg ggcgtgagcg cttcgagatg   1020
ttccgagagc tgaatgaggc cttggaactc aaggatgccc aggctgggaa ggagccaggg   1080
gggagcaggg ctcactccag ccacctgaag tccaaaaagg gtcagtctac ctcccgccat   1140
aaaaaactca tgttcaagac agaagggcct gactcagact ga                       1182
```

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

```
Cys Pro Gly Arg Glu Arg Arg Thr Glu Glu
1               5                   10
```